US009949965B2

(12) United States Patent
Lee et al.

(10) Patent No.: US 9,949,965 B2
(45) Date of Patent: Apr. 24, 2018

(54) TRICYCLIC INDOLE MCL-1 INHIBITORS AND USES THEREOF

(71) Applicant: Vanderbilt University, Nashville, TN (US)

(72) Inventors: Taekyu Lee, Brentwood, TN (US); Jason P. Burke, Houston, TX (US); Edward T. Olejniczak, Nashville, TN (US); Johannes Belmar, Nashville, TN (US); Zhiguo Bian, Nashville, TN (US); Stephen W. Fesik, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/885,181

(22) Filed: Oct. 16, 2015

(65) Prior Publication Data

US 2016/0106731 A1 Apr. 21, 2016

Related U.S. Application Data

(60) Provisional application No. 62/065,271, filed on Oct. 17, 2014.

(51) Int. Cl.
| | |
|---|---|
| *A61K 31/554* | (2006.01) |
| *A61K 31/542* | (2006.01) |
| *A61K 31/4745* | (2006.01) |
| *C07D 513/06* | (2006.01) |
| *C07D 471/08* | (2006.01) |
| *C07D 498/06* | (2006.01) |
| *A61K 31/5383* | (2006.01) |
| *A61K 45/06* | (2006.01) |

(52) U.S. Cl.
CPC ...... *A61K 31/4745* (2013.01); *A61K 31/5383* (2013.01); *A61K 31/542* (2013.01); *A61K 31/554* (2013.01); *A61K 45/06* (2013.01); *C07D 471/08* (2013.01); *C07D 498/06* (2013.01); *C07D 513/06* (2013.01)

(58) Field of Classification Search
CPC ............................ A61K 31/554; A61K 31/542
USPC ....................................................... 514/434
See application file for complete search history.

(56) References Cited

U.S. PATENT DOCUMENTS

| | | | |
|---|---|---|---|
| 4,703,053 A | 10/1987 | Connor et al. | |
| 5,324,725 A * | 6/1994 | Jasserand ............. | C07D 471/06 514/214.01 |
| 6,787,651 B2 | 9/2004 | Stolle et al. | |
| 2003/0109533 A1 | 6/2003 | Lavielle et al. | |
| 2005/0124675 A1 | 6/2005 | Hsich et al. | |
| 2009/0054402 A1 | 2/2009 | Wang et al. | |
| 2009/0270497 A1 | 10/2009 | Buggy | |
| 2010/0009986 A1 | 1/2010 | Zemolka et al. | |
| 2010/0009991 A1 | 1/2010 | Terasaka et al. | |
| 2011/0263599 A1 | 10/2011 | Song et al. | |
| 2012/0172285 A1 | 7/2012 | Walensky et al. | |
| 2015/0336925 A1 | 11/2015 | Lee et al. | |

FOREIGN PATENT DOCUMENTS

| | | |
|---|---|---|
| EP | 639573 | 2/1995 |
| EP | 2161266 | 3/2010 |
| FR | 2761070 | 9/1998 |
| JP | 3739432 | 1/2006 |
| WO | 9742188 | 11/1997 |
| WO | 9810778 | 3/1998 |
| WO | 2007112322 | 10/2007 |
| WO | 2010123507 | 10/2010 |
| WO | 2011157668 | 12/2011 |
| WO | 2013112878 | 8/2013 |
| WO | 2014047427 | 3/2014 |
| WO | 2015031608 | 3/2015 |
| WO | 2015148854 | 10/2015 |

OTHER PUBLICATIONS

PCT/US2013/060881 International Search Report and Written Opinion dated May 5, 2014 (11 pages).
PCT/US2014/053148 International Search Report and Written Opinion dated Jan. 27, 2015 (12 pages).
PCT/US2014/053148 International Preliminary Report on Patentability dated Mar. 1, 2016 (2 pages).
PCT/US2015/022841 International Search Report and Written Opinion dated Jun. 29, 2015 (12 pages).
Friberg, "Discovery of Potent Myeloid Cell Leukemia 1 (Mcl 1) Inhibitors Using Fragment Based Methods and Structure Based Design," manuscript (2014) pp. 1-38, National Institutes of Health.
Hung et al, "Document No. 152:66468, Caplus," retrieved from STN; Oct. 28, 2009.
Jansen et al., "Document No. 140:111233, Caplus," retrieved from STN; Oct. 22, 2009.
Chan et al., "Document No. 150:563639, Caplus," retrieved from STN; May 22, 2009.
PCT/US2017/020699 International Search Report and Written Opinion dated May 23, 2017 (9 pages).
EP14839887.8 Extended European Search Report dated May 30, 2017 (13 pages).
EP15768818.5 Extended European Search Report dated Jul. 28, 2107 (16 pages).
Tanaka et al., "Discovery of Potewnt Mcl-1/Bcl-xL dual Inhibitors by Using a Hybridization Strategy Based n Structural Analysis of Target Proteins," article (2013) ACS Publicatons, J. Med. Chem 56, pp. 9635-9645.
Zhao et al., "Structure of a Myeloid cell leukemia-1 (Mcl-1) inhibitor bound to drug site 3 of Human Serum Albumin," article (2017) Bio-Organic & Medicinal Chemistry, vol. 25, No. 12, pp. 3087-3092.
Lee et al., "Discovery and biological characterizaton of potent myeloid cell leukemia-1 inhibitors," article (2016) Febs Letters, vol. 591, No. 1, pp. 240-251.
Wahyuningsih, et al. Document No. 147:235137, retrieved from STN; entered in STN on Jun. 11, 2007.

\* cited by examiner

*Primary Examiner* — Kathrien Cruz
*Assistant Examiner* — Janet L Coppins
(74) *Attorney, Agent, or Firm* — Michael Best & Friedrich LLP

(57) ABSTRACT

The present invention provides for compounds that inhibit the activity of an anti-apoptotic Bcl-2 family member Myeloid cell leukemia-1 (Mcl-1) protein. The present invention also provides for pharmaceutical compositions as well as methods for using compounds for treatment of diseases and conditions (e.g., cancer) characterized by the overexpression or dysregulation of Mcl-1 protein.

19 Claims, No Drawings

TRICYCLIC INDOLE MCL-1 INHIBITORS AND USES THEREOF

CROSS-REFERENCE TO RELATED APPLICATION

This claims priority to U.S. Provisional Patent Application No. 62/065,271, filed on Oct. 17, 2014, the contents of which are fully incorporated herein by reference.

SEQUENCE LISTING

Incorporated by reference in its entirety herein is a computer-readable nucleotide/amino acid sequence listing identified as follows: One 532 byte text file named "093386-9134-US01 As Filed Sequence Listing," created on Nov. 6, 2015.

STATEMENT REGARDING FEDERALLY SPONSORED RESEARCH OR DEVELOPMENT

This invention was made with government support under CA098131 and CA174419 awarded by the National Institutes of Health. The Government has certain rights to the invention.

FIELD OF THE INVENTION

The present invention pertains to compounds that inhibit the activity of an anti-apoptotic Bcl-2 family member Myeloid cell leukemia-1 (Mcl-1) protein, compositions containing the compounds, and methods of treating cancer involving over-expressed or dysregulated Mcl-1 protein.

BACKGROUND OF THE INVENTION

Abnormal regulation of apoptosis is now recognized to play an important role in the development of cancer. The apoptosis pathway can be initiated by various extracellular and intracellular stresses, including growth factor deprivation, DNA damage, oncogene induction, and cytotoxic drugs (Danial, N. N. and Korsmeyer, S J. *Cell* (2004) 116, 205-219). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. Recent data suggests that the anti-apoptotic Bcl-2 proteins function to protect the cell from apoptotic insults, primarily by preventing disruption of mitochondrial outer membrane integrity by binding to the pro-apoptotic proteins as described in Adams, J. M. and Cory S. *Oncogene* (2007) 26, 1324-1337; Willis, S. N. et al. *Science* (2007) 315, 856-859. Because tumor cells are under stress, alterations in their apoptotic signaling pathways are believed to be crucial for survival. Recent data implicates down-regulated apoptosis in the onset of cancer. Research has shown, for example, that anti-apoptotic proteins, are over-expressed in many cancer cell types as described in Beroukhim, R. et al. *Nature* (2010) 463, 899-905; Zhang J. Y., *Nature Reviews Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy which is a major cause of treatment failure and poor prognosis in many cancers can be caused by the upregulation of anti-apoptotic Bcl-2 family proteins.

An important anti-apoptotic member of the Bcl-2 family is Myeloid cell leukemia-1 (Mcl-1). Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) (Beroukhim et al. *Nature* (2010) 463, 899-905). Moreover, its overexpression is implicated as a resistance factor for multiple therapies including widely prescribed microtubule-targeted agents for breast cancers, such as paclitaxel and vincristine as well as Gemcitabine, a first-line treatment option for pancreatic cancer (Wei et al. *Cancer Chemother Pharmacol* (2008) 62, 1055-1064 and Wertz et al. *Nature* (2011) 471, 110-114). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 proteins. A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

SUMMARY OF THE INVENTION

In some embodiments, the present invention provides compounds, and pharmaceutically acceptable compositions thereof, that are effective as inhibitors of Mcl-1. Such compounds have the general formula I:

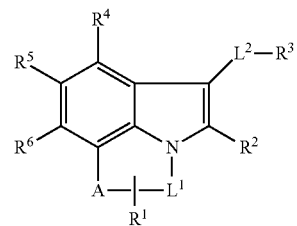

or a pharmaceutically acceptable salt thereof, wherein each of $R^1$, $R^2$, $R^3$, $R^4$, $R^5$, $R^6$, A, $L^1$ and $L^2$ is as defined and described in embodiments herein.

Compounds of the present invention, and pharmaceutically acceptable compositions thereof, are useful for treating a variety of diseases, disorders or conditions, associated with Mcl-1. Such diseases, disorders, or conditions include those described herein.

Compounds provided by this invention are also useful for the study of Mcl-1 in biological and pathological phenomena and the comparative evaluation of new Mcl-1 inhibitors in vitro or in vivo.

DETAILED DESCRIPTION OF CERTAIN EMBODIMENTS OF THE INVENTION

1. General Description of Compounds of the Invention

In certain embodiments, the present invention provides inhibitors of Mcl-1. In some embodiments, such compounds include those of formula I:

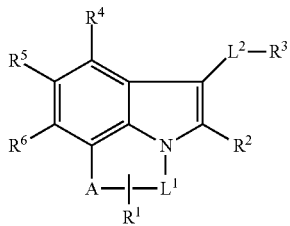

or a pharmaceutically acceptable salt thereof, wherein:

$L^1$ is selected from a covalent bond or an optionally substituted bivalent straight or branched $C_{1-6}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

A is —O—, —S—, —S(O)—, —S(O)$_2$—, —N(R')—, or optionally substituted —CH$_2$—;

$R^1$ is hydrogen, —R, —OR, —SR, —S(O)R, —S(O)$_2$R, —S(O)$_2$N(R)$_2$, —N(R)$_2$, —C(O)N(R)$_2$, —C(O)R, —C(O)OR, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

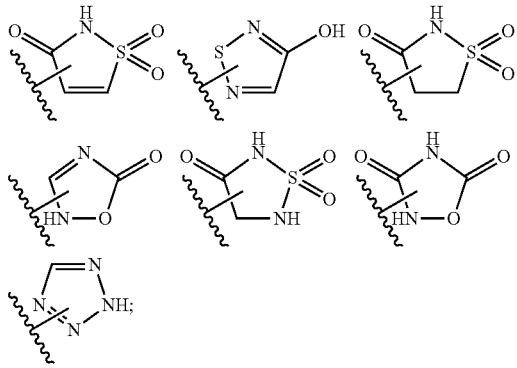

$R^2$ is selected from R, halo, —NH$_2$, —CN, —NO$_2$, —CF$_3$—C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$;

$L^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

$R^z$ is hydrogen, R, —OR, —SR, —S(O)R, —S(O)$_2$R, —S(O)$_2$N(R)$_2$, —N(R)$_2$, —C(O)N(R)$_2$, —C(O)R, —C(O)OR, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

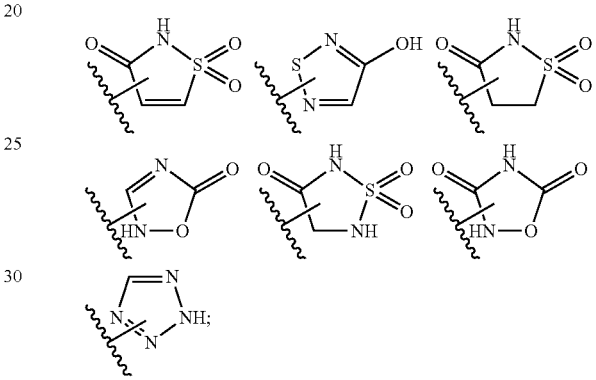

$R^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

$R^y$ is selected from —N(R)C(O)CF$_3$, —N(R)C(O)R, or —N(R)C(O)N(R)$_2$;

each R is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;

$L^2$ is an optionally substituted bivalent straight or branched $C_{3-6}$ hydrocarbon chain wherein one or two methylene units of $L^2$ are optionally and independently replaced with —O—, —S—, or —N(R')—, and wherein two substituents of $L^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted C$_{1-4}$ alkyl;

R$^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of R$^4$, R$^5$, and R$^6$ is independently selected from R, halogen, —CN, —NO$_2$, —CF$_3$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$ R', —N(R')C(O)OR', and —N(R')S(O)$_2$R'; and optionally R$^2$ and -A-L$^1$-, R$^2$ and -L$^2$-R$^3$, R$^4$ and R$^5$, R$^5$ and R$^6$ and/or R$^6$ and -A-L$^1$- are independently taken together with their intervening atoms to form an optionally substituted ring selected from a 4-8 membered saturated or partially unsaturated carbocyclic ring, phenyl, a 4-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic or polycyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a C1-4 straight or branched alkyl group. Exemplary lower alkyl groups are methyl, ethyl, propyl, isopropyl, butyl, isobutyl, and tert-butyl.

The term "lower haloalkyl" refers to a C1-4 straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen; or a substitutable nitrogen of a heterocyclic ring, for example N (as in 3,4-dihydro-2H-pyrrolyl), NH (as in pyrrolidinyl) or NR+ (as in N-substituted pyrrolidinyl)).

The term "unsaturated," as used herein, means that a moiety has one or more units of unsaturation.

As used herein, the term "bivalent C1-8 (or C1-6) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)n-, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, naphthyl, anthracyl and the like, which may be optionally substituted. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $-(CH_2)_{0-4}SC(O)R^\circ$; $-(CH_2)_{0-4}C(O)NR^\circ_2$; $-(CH_2)_{0-4}C(O)N(R^\circ)S(O)_2R^\circ$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)R^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-S(O)_2N(R^\circ)C(O)R^\circ$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $-SiR^\circ_3$; $-(C1-4$ straight or branched alkylene$)O-N(R^\circ)_2$; or $-(C1-4$ straight or branched alkylene$)C(O)O-N(R^\circ)_2$, wherein each $R^\circ$ may be substituted as defined below and is independently hydrogen, C1-6 aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}S(O)R^\bullet$, $-(CH_2)_{0-2}S(O)_2R^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene$)C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a suitable carbon atom of an "optionally substituted" group include the following: $=O$, $=S$, $=NNR^*_2$, $=NNHC(O)R^*$, $=NNHC(O)OR^*$, =NNHS(O)₂R*, =NR*, =NOR*, —O(C(R*₂))₂₋₃O—, or —S(C(R*₂))₂₋₃S—, wherein each independent occurrence of R* is selected from hydrogen, C₁₋₆aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₃O—, wherein each independent occurrence of R* is selected from hydrogen, C₁₋₆aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)R●, —C(O)OH, —C(O)OR●, —C(O)NR●₂, —SR●, —S(O)R●, —S(O)₂R●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of Rt are independently halogen, —R●, -(haloR●), —OH, —OR●, —O(haloR●), —CN, —C(O)OH, —C(O)OR●, —C(O)NR●₂, —SR●, —S(O)R●, —S(O)₂R●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N+(C1-4alkyl)₄ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a 13C- or 14C-enriched carbon are within the scope of this invention. Such compounds are useful, for example, as analytical tools, as probes in biological assays, or as therapeutic agents in accordance with the present invention.

3. Description of Exemplary Embodiments

In some embodiments, the present invention provides a compound of formula I:

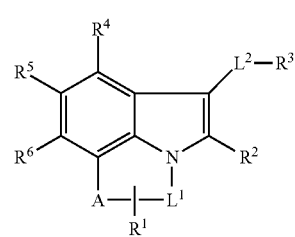

or a pharmaceutically acceptable salt thereof, wherein:
L¹ is selected from a covalent bond or an optionally substituted bivalent straight or branched C₁₋₆ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

A is —O—, —S—, —S(O)—, —S(O)$_2$—, —N(R')—, or optionally substituted —CH$_2$—;

R$^1$ is hydrogen, —R, —OR, —SR, —S(O)R, —S(O)$_2$R, —S(O)$_2$N(R)$_2$, —N(R)$_2$, —C(O)N(R)$_2$, —C(O)R, —C(O)OR, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

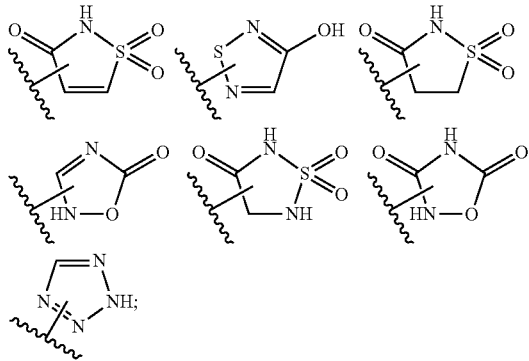

R$^2$ is selected from R, halo, —NH$_2$, —CN, —NO$_2$, —CF$_3$, —C(O)-L$^3$-R$^z$, —C(O)N(R)-L$^3$-R$^z$, —C(O)N(R)—C(R)$_2$-L$^3$-R$^z$, —C(O)O-L$^3$-R$^z$ or —C(O)S-L$^3$-R$^z$;

L$^3$ is selected from a covalent bond or an optionally substituted bivalent straight or branched C$_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

R$^z$ is hydrogen, R, —OR, —SR, —S(O)R, —S(O)$_2$R, —S(O)$_2$N(R)$_2$, —N(R)$_2$, —C(O)N(R)$_2$, —C(O)R, —C(O)OR, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^y$, or is selected from:

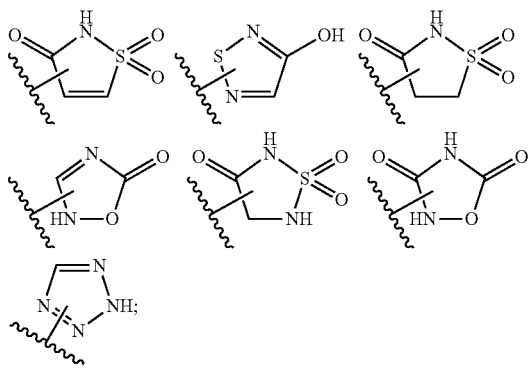

R$^x$ is selected from —C(O)OR, —N(R)S(O)$_2$CF$_3$, —N(R)C(O)R, —N(R)C(O)OR, —N(R)C(O)N(R)$_2$, or —N(R)S(O)$_2$R;

R$^y$ is selected from —N(R)C(O)CF$_3$, —N(R)C(O)R, or —N(R)C(O)N(R)$_2$;

each R is independently selected from hydrogen or an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur;

L$^2$ is an optionally substituted bivalent straight or branched C$_{3-6}$ hydrocarbon chain wherein one or two methylene units of L$^2$ are optionally and independently replaced with —O—, —S—, or —N(R')—, and wherein two substituents of L$^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur;

each R' is independently hydrogen or optionally substituted C$_{1-4}$ alkyl;

R$^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each of R$^4$, R$^5$, and R$^6$ is independently selected from R, halogen, —CN, —NO$_2$, —CF$_3$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'; and optionally R$^2$ and -A-L$^1$-, R$^2$ and -L$^2$-R$^3$, R$^4$ and R$^5$, R$^5$ and R$^6$ and/or R$^6$ and -A-L$^1$- are independently taken together with their intervening atoms to form an optionally substituted ring selected from a 4-8 membered saturated or partially unsaturated carbocyclic ring, phenyl, a 4-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

As generally defined above, L$^1$ of formula I is selected from a covalent bond or an optionally substituted bivalent straight or branched C$_{1-6}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, L$^1$ is a covalent bond. In some embodiments, L$^1$ is an optionally substituted bivalent straight or branched C$_{1-6}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_{1-6}$ hydrocarbon chain. In some embodiments, $L^1$ is an optionally substituted bivalent straight or branched C1-6 hydrocarbon chain wherein one or more methylene units are independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, $L^1$ is an optionally substituted bivalent straight or branched $C_{2-6}$ hydrocarbon chain. In some embodiments, $L^1$ is an optionally substituted bivalent straight or branched $C_{3-6}$ hydrocarbon chain. In some embodiments, $L^1$ is an optionally substituted bivalent straight or branched $C_{4-6}$ hydrocarbon chain. In some embodiments, $L^1$ is an optionally substituted bivalent straight or branched $C_{5-6}$ hydrocarbon chain. In some embodiments, $L^1$ is an optionally substituted methylene group. In some embodiments, $L^1$ is an optionally substituted bivalent $C_2$ hydrocarbon chain. In some embodiments, $L^1$ is an optionally substituted bivalent straight or branched $C_3$ hydrocarbon chain. In some embodiments, $L^1$ is an optionally substituted bivalent straight or branched $C_4$ hydrocarbon chain. In some embodiments, $L^1$ is an optionally substituted bivalent straight or branched $C_5$ hydrocarbon chain. In some embodiments, $L^1$ is an optionally substituted bivalent straight or branched $C_6$ hydrocarbon chain.

In some embodiments, $L^1$ is an unsubstituted bivalent $C_{1-6}$ hydrocarbon chain. In some embodiments, $L^1$ is an unsubstituted bivalent $C_{2-6}$ hydrocarbon chain. In some embodiments, $L^1$ is an unsubstituted bivalent $C_{3-6}$ hydrocarbon chain. In some embodiments, $L^1$ is an unsubstituted bivalent $C_{4-6}$ hydrocarbon chain. In some embodiments, $L^1$ is an unsubstituted bivalent $C_{5-6}$ hydrocarbon chain. In some embodiments, $L^1$ is an unsubstituted methylene group. In some embodiments, $L^1$ is an unsubstituted bivalent $C_2$ hydrocarbon chain. In some embodiments, $L^1$ is an unsubstituted bivalent $C_3$ hydrocarbon chain. In some embodiments, $L^1$ is an unsubstituted bivalent $C_4$ hydrocarbon chain. In some embodiments, $L^1$ is an unsubstituted bivalent $C_5$ hydrocarbon chain. In some embodiments, $L^1$ is an unsubstituted bivalent $C_6$ hydrocarbon chain.

In some embodiments, $L^1$ is a substituted bivalent $C_{1-6}$ hydrocarbon chain. In some embodiments, $L^1$ is a substituted bivalent $C_{2-6}$ hydrocarbon chain. In some embodiments, $L^1$ is a substituted bivalent $C_{3-6}$ hydrocarbon chain. In some embodiments, $L^1$ is a substituted bivalent $C_{4-6}$ hydrocarbon chain. In some embodiments, $L^1$ is a substituted bivalent $C_{5-6}$ hydrocarbon chain. In some embodiments, $L^1$ is a substituted methylene group. In some embodiments, $L^1$ is a substituted bivalent $C_2$ hydrocarbon chain. In some embodiments, $L^1$ is a substituted bivalent $C_3$ hydrocarbon chain. In some embodiments, $L^1$ is a substituted bivalent $C_4$ hydrocarbon chain. In some embodiments, $L^1$ is a substituted bivalent $C_5$ hydrocarbon chain. In some embodiments, $L^1$ is a substituted bivalent $C_6$ hydrocarbon chain.

In some embodiments, $L^1$ is optionally substituted methylene. In some embodiments, $L^1$ is —CH$_2$—. In some embodiments, $L^1$ is optionally substituted —CH$_2$CH$_2$—. In some embodiments, $L^1$ is —CH$_2$CH$_2$—. In some embodiments, $L^1$ is —CH(CH$_3$)—. In some embodiments, $L^1$ is —CH(CH$_2$CH$_3$)—. In some embodiments, $L^1$ is —CH(Ph)-. In some embodiments, $L^1$ is —CH(CH$_3$)CH$_2$—. In some embodiments, $L^1$ is —CH(Ph)CH$_2$—.

In some embodiments, $L^1$ is partially unsaturated. In some embodiments, $L^1$ comprises one or more double bonds. In some embodiments, $L^1$ is —CH=CH—. In some embodiments, $L^1$ comprises one or more triple bonds.

In some embodiments, $L^1$ is an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted methylene group or -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_2$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_3$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_4$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_5$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_6$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_7$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^1$ is an optionally substituted bivalent straight or branched $C_8$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, $L^1$ is an optionally substituted bivalent straight or branched $C_{1-8}$ hydrocarbon chain wherein one or more methylene units are independently replaced with -Cy-, —O—, —S—, —N(R)—, —N(R)C(O)—, —C(O)—, —C(O)N(R)—, or —S(O)—. In some embodiments, L is an optionally substituted bivalent straight or branched $C_{1-8}$ hydrocarbon chain wherein one or more methylene units are independently replaced with -Cy-, —O—, —N(R)—, —N(R)C(O)—, —C(O)—, or —C(O)N(R)—. In some embodiments, $L^1$ is an optionally substituted bivalent straight or branched $C_{1-8}$ hydrocarbon chain wherein one or more methylene units are independently replaced with -Cy- or —O—.

In some embodiments, one or more methylene units are replaced with -Cy-. In some embodiments, one or more methylene units are replaced with —O—. In some embodiments, one or more methylene units are replaced with —S—. In some embodiments, one or more methylene units are replaced with —N(R)—. In some embodiments, one or more methylene units are replaced with —N(R)C(O)—. In some embodiments, one or more methylene units are replaced with —N(R)S(O)$_2$—. In some embodiments, one or more methylene units are replaced with —C(O)—. In some embodiments, one or more methylene units are replaced with —C(O)N(R)—. In some embodiments, one or more methylene units are replaced with —S(O)—. In some embodiments, one or more methylene units are replaced with —S(O)$_2$—. In some embodiments, one or more methylene units are replaced with —S(O)$_2$N(R)—.

As defined generally above, -Cy- of formula I is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur.

In some embodiments, -Cy- is optionally substituted phenylene. In some embodiments, -Cy- is substituted phenylene. In some embodiments, -Cy- is unsubstituted phenylene. In some embodiments, -Cy- is

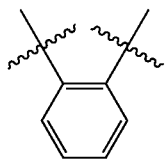

In some embodiments, -Cy- is

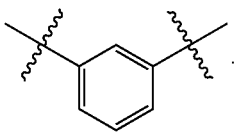 [SMILES: *c1cccc(*)c1]

In some embodiments, -Cy- is

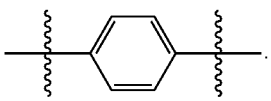

In some embodiments, -Cy- is optionally substituted bivalent 3-8 membered saturated or partially unsaturated carbocyclylene. In certain embodiments, -Cy- is optionally substituted bivalent 3-8 membered saturated carbocyclylene. In certain embodiments, -Cy- is optionally substituted bivalent 3-6 membered saturated carbocyclylene. In certain embodiments, -Cy- is optionally substituted bivalent 3-membered saturated carbocyclylene. In certain embodiments, -Cy- is optionally substituted bivalent 4-membered saturated carbocyclylene. In certain embodiments, -Cy- is optionally substituted bivalent 5-membered saturated carbocyclylene. In certain embodiments, -Cy- is optionally substituted bivalent 6-membered saturated carbocyclylene.

In some embodiments, -Cy- is optionally substituted bivalent 5-6 membered heteroarylene having 1-4 heteroatoms independently selected from nitrogen, oxygen, or sulfur. In certain embodiments, -Cy- is optionally substituted bivalent 5-membered heteroarylene having 1-4 heteroatoms independently selected from nitrogen, oxygen, or sulfur. In certain embodiments, -Cy- is optionally substituted bivalent 5-membered heteroarylene having 1-2 heteroatoms independently selected from nitrogen, oxygen, or sulfur. In certain embodiments, -Cy- is optionally substituted bivalent 5-membered heteroarylene having one heteroatom independently selected from nitrogen, oxygen, or sulfur. In some embodiments, -Cy- is

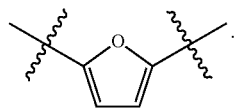 [SMILES: *c1ccc(*)o1]

In certain embodiments, -Cy- is optionally substituted bivalent 6-membered heteroarylene having 1-4 heteroatoms independently selected from nitrogen, oxygen, or sulfur. In certain embodiments, -Cy- is optionally substituted bivalent 6-membered heteroarylene having 1-2 heteroatoms independently selected from nitrogen, oxygen, or sulfur.

In some embodiments, -Cy- is optionally substituted bivalent 3-8 membered saturated or partially unsaturated heterocyclylene having 1-4 heteroatoms independently selected from nitrogen, oxygen, or sulfur. In certain embodiments, -Cy- is optionally substituted bivalent 3-8 membered saturated heterocyclylene having 1-4 heteroatoms independently selected from nitrogen, oxygen, or sulfur. In certain embodiments, -Cy- is optionally substituted bivalent 3-8 membered saturated heterocyclylene having 1-2 heteroatoms independently selected from nitrogen, oxygen, or sulfur. In certain embodiments, -Cy- is optionally substituted bivalent 5-6 membered saturated heterocyclylene having 1-4 heteroatoms independently selected from nitrogen, oxygen, or sulfur. In certain embodiments, -Cy- is optionally substituted bivalent 5-6 membered saturated heterocyclylene having 1-2 heteroatoms independently selected from nitrogen, oxygen, or sulfur. In certain embodiments, -Cy- is optionally substituted bivalent 5-membered saturated heterocyclylene having 1-2 heteroatoms independently selected from nitrogen, oxygen, or sulfur. In certain embodiments, -Cy- is optionally substituted bivalent 6-membered saturated heterocyclylene having 1-2 heteroatoms independently selected from nitrogen, oxygen, or sulfur.

As defined generally above, $R^1$ of formula I is hydrogen, —R, —OR, —SR, —S(O)R, —S(O)$_2$R, —S(O)$_2$N(R)$_2$, —N(R)$_2$, —C(O)N(R)$_2$, —C(O)R, —C(O)OR, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

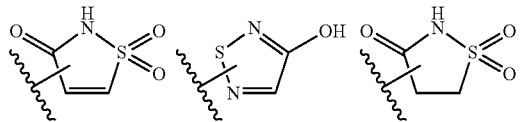

-continued

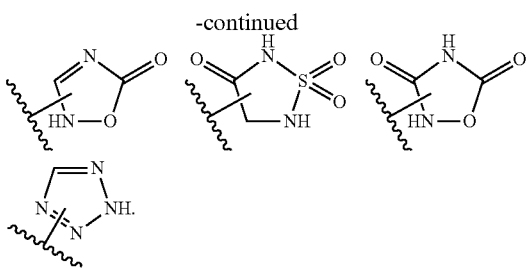

In some embodiments, $R^1$ is hydrogen. In some embodiments, $R^1$ is not hydrogen. In some embodiments, $R^1$ is —R, —OR, —SR, —S(O)R, —S(O)$_2$R, —S(O)$_2$N(R)$_2$, —N(R)$_2$, —C(O)N(R)$_2$, —C(O)R, —C(O)OR, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$.

In some embodiments, $R^1$ is —R. In some embodiments, $R^1$ is —OR. In some embodiments, $R^1$—SR. In some embodiments, $R^1$ is —S(O)R. In some embodiments, $R^1$ is —S(O)$_2$R. In some embodiments, $R^1$ is —S(O)$_2$N(R)$_2$. In some embodiments, $R^1$ is —N(R)$_2$. In some embodiments, $R^1$ is —C(O)N(R)$_2$. In some embodiments, $R^1$ is —C(O)R. In some embodiments, $R^1$ is —C(O)OR. In some embodiments, $R^1$ is —N(R)C(O)R. In some embodiments, $R^1$ is —N(R)C(O)OR. In some embodiments, $R^1$ is —N(R)C(O)N(R)$_2$. In some embodiments, $R^1$ is —N(R)S(O)$_2$R. In some embodiments, $R^1$ is —N(R)S(O)$_2$N(R)$_2$. In some embodiments, $R^1$ is —C(O)OH. In some embodiments, $R^1$ is —C(O)R$^x$. In some embodiments, $R^1$ is —S(O)$_2$OH. In some embodiments, $R^1$ is —S(O)$_2$R$^y$.

As defined generally above, $R^x$ of formula I is selected from —C(O)OR, —N(R)S(O)$_2$CF$_3$, —N(R)C(O)R, —N(R)C(O)OR, —N(R)C(O)N(R)$_2$, or —N(R)S(O)$_2$R. In some embodiments, $R^x$ is —C(O)OR. In some embodiments, $R^x$ is —N(R)S(O)$_2$CF$_3$. In some embodiments, $R^x$ is —N(R)C(O)R. In some embodiments, $R^x$ is —NHC(O)R. In some embodiments, $R^x$ is —NHC(O)R, wherein R is not hydrogen. In some embodiments, $R^x$ is —N(R)C(O)OR. In some embodiments, $R^x$ is —NHC(O)OR. In some embodiments, $R^x$ is —NHC(O)OR, wherein R is not hydrogen. In some embodiments, $R^x$ is —N(R)C(O)N(R)$_2$. In some embodiments, $R^x$ is —NHC(O)N(R)$_2$. In some embodiments, $R^x$ is —NHC(O)N(R)$_2$, wherein at least one R is not hydrogen. In some embodiments, $R^x$ is —N(R)S(O)$_2$R. In some embodiments, $R^x$ is —NHS(O)$_2$R. In some embodiments, $R^x$ is —NHS(O)$_2$R, wherein R is not hydrogen.

As defined generally above, $R^y$ of formula I is selected from —N(R)C(O)CF$_3$, —N(R)C(O)R, or —N(R)C(O)N(R)$_2$. In some embodiments, $R^y$ is —N(R)C(O)CF$_3$. In some embodiments, $R^y$ is —NHC(O)CF$_3$. In some embodiments, $R^y$ is —N(R)C(O)R. In some embodiments, $R^y$ is —NHC(O)R. In some embodiments, $R^y$ is —NHC(O)R, wherein R is not hydrogen. In some embodiments, $R^y$ is —N(R)C(O)N(R)$_2$. In some embodiments, $R^y$ is —NHC(O)N(R)$_2$. In some embodiments, $R^y$ is —NHC(O)N(R)$_2$, wherein at least one R is not hydrogen.

As defined generally above, each R of formula I is independently selected from hydrogen or an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, each R is independently selected from hydrogen or an optionally substituted group selected from $C_{1-6}$ aliphatic or a ring selected from a 3-10 membered saturated or partially unsaturated carbocyclic ring, phenyl, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

In some embodiments, R is hydrogen.

In some embodiments, R is an optionally substituted group selected from $C_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, or sulfur, a 5-6 membered heteroaryl ring having 1-4 heteroatoms independently selected from nitrogen, oxygen, or sulfur, a 7-10 membered bicyclic saturated or partially unsaturated heterocyclic ring having 1-5 heteroatoms independently selected from nitrogen, oxygen or sulfur, or an 8-10 membered bicyclic heteroaryl ring having 1-5 heteroatoms independently selected from nitrogen, oxygen or sulfur. In some embodiments, R is an optionally substituted group selected from $C_{1-6}$ aliphatic or a ring selected from a 3-10 membered saturated or partially unsaturated carbocyclic ring, phenyl, a 3-8 membered saturated or partially unsaturated heterocyclic ring having 1-2 heteroatoms independently selected from nitrogen, oxygen, or sulfur, or a 5-6 membered heteroaryl ring having 1-4 heteroatoms independently selected from nitrogen, oxygen, or sulfur.

In some embodiments, R is substituted. In some embodiments, R is unsubstituted.

In some embodiments, R is optionally substituted $C_{1-12}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is optionally substituted adamantyl. In some embodiments, R is

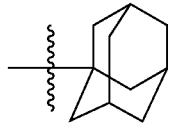

In some embodiments, R is

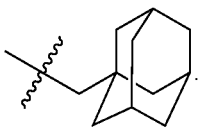 [SMILES: *CC12CC3CC(CC(C3)C1)C2]

In some embodiments, R is an optionally substituted 3-10 membered saturated or partially unsaturated carbocyclic ring. In some embodiments, R is an optionally substituted 3-10 membered saturated or partially unsaturated monocyclic, bicyclic or polycyclic carbocyclic ring. In some embodiments, R is an optionally substituted 3-10 membered saturated or partially unsaturated monocyclic, bicyclic or tricyclic carbocyclic ring. In some embodiments, R is an optionally substituted 3-10 membered saturated or partially unsaturated monocyclic or bicyclic carbocyclic ring. In some embodiments, R is an optionally substituted 3-10 membered saturated or partially unsaturated monocyclic carbocyclic ring. In some embodiments, R is an optionally substituted 4-10 membered saturated or partially unsaturated bicyclic carbocyclic ring. In some embodiments, R is an optionally substituted 4-10 membered saturated or partially unsaturated polycyclic carbocyclic ring. In some embodiments, R is an optionally substituted 3-10 membered saturated or partially unsaturated tricyclic carbocyclic ring. In some embodiments, R is an optionally substituted 3-membered saturated or partially unsaturated monocyclic carbocyclic ring. In some embodiments, R is an optionally substituted 4-membered saturated or partially unsaturated monocyclic carbocyclic ring. In some embodiments, R is an optionally substituted 5-membered saturated or partially unsaturated monocyclic carbocyclic ring. In some embodiments, R is an optionally substituted 6-membered saturated or partially unsaturated monocyclic carbocyclic ring. In some embodiments, R is an optionally substituted 6-membered saturated or partially unsaturated bicyclic carbocyclic ring. In some embodiments, R is an optionally substituted 7-membered saturated or partially unsaturated monocyclic carbocyclic ring. In some embodiments, R is an optionally substituted 7-membered saturated or partially unsaturated bicyclic carbocyclic ring. In some embodiments, R is an optionally substituted 8-membered saturated or partially unsaturated monocyclic carbocyclic ring. In some embodiments, R is an optionally substituted 8-membered saturated or partially unsaturated bicyclic carbocyclic ring. In some embodiments, R is an optionally substituted 10-membered saturated or partially unsaturated monocyclic carbocyclic ring. In some embodiments, R is an optionally substituted 10-membered saturated or partially unsaturated bicyclic carbocyclic ring. In some embodiments, R is an optionally substituted 10-membered saturated or partially unsaturated tricyclic carbocyclic ring.

In some embodiments, R is an optionally substituted 3-8 membered saturated monocyclic carbocyclic ring. In some embodiments, R is an optionally substituted cycloheptyl. In some embodiments, R is an optionally substituted cyclohexyl. In some embodiments, R is an optionally substituted cyclopentyl. In some embodiments, R is an optionally substituted cyclobutyl. In some embodiments, R is an optionally substituted cyclopropyl.

In some embodiments, R is an optionally substituted 3-8 membered unsaturated monocyclic carbocyclic ring. In some embodiments, R is an optionally substituted cycloheptenyl. In some embodiments, R is an optionally substituted cyclohexenyl. In some embodiments, R is an optionally substituted cyclopentenyl. In some embodiments, R is an optionally substituted cyclobutenyl. In some embodiments, R is an optionally substituted cyclopropenyl.

In some embodiments, R is optionally substituted phenyl. In some embodiments, R is unsubstituted phenyl. In some embodiments, R is substituted phenyl. In some embodiments, R is 4-bromophenyl. In some embodiments, R is 2-trifuoromethylphenyl. In some embodiments, R is 4-trifuoromethylphenyl. In some embodiments, R is 2-cyanophenyl. In some embodiments, R is 3-cyanophenyl. In some embodiments, R is 4-cyanophenyl. In some embodiments, R is 2-nitrophenyl. In some embodiments, R is 3-nitrophenyl. In some embodiments, R is 4-nitrophenyl.

In some embodiments, R is a 6-10 membered bicyclic saturated, partially unsaturated or aryl ring. In some embodiments, R is a 6-10 membered bicyclic saturated ring. In some embodiments, R is an 8-10 membered bicyclic partially unsaturated ring. In some embodiments, R is an 8-10 membered bicyclic aryl ring. In some embodiments, R is optionally substituted naphthyl. In some embodiments, R is

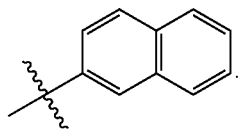 [SMILES: *c1ccc2ccccc2c1]

In some embodiments, R is an optionally substituted 3-8 membered saturated or partially unsaturated heterocyclic ring having 1-2 heteroatoms independently selected from nitrogen, oxygen or sulfur. In some embodiments, R is a substituted 3-8 membered saturated or partially unsaturated heterocyclic ring having 1-2 heteroatoms independently selected from nitrogen, oxygen or sulfur. In some embodiments, R is an unsubstituted 3-8 membered saturated or partially unsaturated heterocyclic ring having 1-2 heteroatoms independently selected from nitrogen, oxygen or sulfur.

In some embodiments, R is an optionally substituted 3-8 membered saturated heterocyclic ring having 1-2 heteroatoms independently selected from nitrogen, oxygen or sulfur. In some embodiments, R is a substituted 3-8 membered saturated heterocyclic ring having 1-2 heteroatoms independently selected from nitrogen, oxygen or sulfur. In some embodiments, R is an unsubstituted 3-8 membered saturated heterocyclic ring having 1-2 heteroatoms independently selected from nitrogen, oxygen or sulfur.

In some embodiments, R is an optionally substituted 3-membered saturated heterocyclic ring having one heteroatom selected from nitrogen, oxygen or sulfur. Exemplary R groups include but are not limited to optionally substituted aziridinyl, thiiranyl or oxiranyl. In some embodiments, R is a substituted 3-membered saturated heterocyclic ring having one heteroatom selected from nitrogen, oxygen or sulfur. In some embodiments, R is an unsubstituted saturated 3-membered heterocyclic ring having one heteroatom selected from nitrogen, oxygen or sulfur.

In some embodiments, R is an optionally substituted 4-membered saturated heterocyclic ring having 1-2 heteroatoms independently selected from nitrogen, oxygen, or sulfur. Exemplary R groups include but are not limited to optionally substituted azetidinyl, oxetanyl, thietanyl, oxazetidinyl, thiazetidinyl, or diazetidinyl. In some embodiments, R is a substituted 4-membered saturated heterocyclic ring having 1-2 heteroatoms independently selected from nitrogen, oxygen, or sulfur. In some embodiments, R is an unsubstituted 4-membered saturated heterocyclic ring having 1-2 heteroatoms independently selected from nitrogen, oxygen, or sulfur.

In some embodiments, R is an optionally substituted 5-membered saturated heterocyclic ring having 1-2 heteroatoms independently selected from nitrogen, oxygen, or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, or thiazolidinyl. In some embodiments, R is a substituted 5-membered saturated heterocyclic ring having 1-2 heteroatoms independently selected from nitrogen, oxygen, or sulfur. In some embodiments, R is an unsubstituted 5-membered saturated heterocyclic ring having 1-2 heteroatoms independently selected from nitrogen, oxygen, or sulfur.

In some embodiments, R is an optionally substituted 6-membered saturated heterocyclic ring having 1-2 heteroatoms independently selected from nitrogen, oxygen, or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, and oxathianyl. In some embodiments, R is a substituted 6-membered saturated heterocyclic ring having 1-2 heteroatoms independently selected from nitrogen, oxygen, or sulfur. In some embodiments, R is an unsubstituted 6-membered saturated heterocyclic ring having 1-2 heteroatoms independently selected from nitrogen, oxygen, or sulfur.

In some embodiments, R is optionally substituted 7-membered saturated heterocyclic ring having 1-2 heteroatoms independently selected from nitrogen, oxygen, or sulfur. Exemplary R groups include but are not limited to optionally substituted azepanyl, oxepanyl, thiepanyl, diazepanyl, oxazepanyl, thiazepanyl, dioxepanyl, oxathiepanyl, or dithiepanyl. In some embodiments, R is a substituted 7-membered saturated heterocyclic ring having 1-2 heteroatoms independently selected from nitrogen, oxygen, or sulfur. In some embodiments, R is an unsubstituted 7-membered saturated heterocyclic ring having 1-2 heteroatoms independently selected from nitrogen, oxygen, or sulfur.

In some embodiments, R is optionally substituted 8-membered saturated heterocyclic ring having 1-2 heteroatoms independently selected from nitrogen, oxygen, or sulfur. In some embodiments, R is a substituted 8-membered saturated heterocyclic ring having 1-2 heteroatoms independently selected from nitrogen, oxygen, or sulfur. In some embodiments, R is an unsubstituted 8-membered saturated heterocyclic ring having 1-2 heteroatoms independently selected from nitrogen, oxygen, or sulfur.

In some embodiments, R is an optionally substituted 3-8 membered partially unsaturated heterocyclic ring having 1-2 heteroatoms independently selected from nitrogen, oxygen or sulfur. In certain embodiments, R is an optionally substituted 5-7 membered partially unsaturated ring having 1-2 heteroatoms independently selected from nitrogen, oxygen, or sulfur. In certain embodiments, R is an optionally substituted 5-6 membered partially unsaturated ring having 1-2 heteroatoms independently selected from nitrogen, oxygen, or sulfur.

In certain embodiments, R is an optionally substituted 5-membered partially unsaturated ring having 1-2 heteroatoms independently selected from nitrogen, oxygen, or sulfur. Exemplary R groups include but are not limited to optionally substituted dihydroimidazolyl, dihydrothiazolyl, dihydrooxazolyl, or oxazolinyl.

In certain embodiments, R is an optionally substituted 6-membered partially unsaturated ring having 1-2 heteroatoms independently selected from nitrogen, oxygen, or sulfur. Exemplary R groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl.

In certain embodiments, R is an optionally substituted 7-membered partially unsaturated ring having 1-2 heteroatoms independently selected from nitrogen, oxygen, or sulfur. Exemplary R groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, tetrahydroazepinyl, tetrahydrooxepinyl, tetrahydrothiepinyl, tetrahydrodiazepinyl, tetrahydrooxazepinyl or tetrahydrothiazepinyl.

In some embodiments, R is an optionally substituted 8-membered partially unsaturated ring having 1-2 heteroatoms independently selected from nitrogen, oxygen or sulfur.

In some embodiments, R is an optionally substituted 5-6 membered heteroaryl ring having 1-4 heteroatoms independently selected from nitrogen, oxygen, or sulfur. In some embodiments, R is a substituted 5-6 membered heteroaryl ring having 1-4 heteroatoms independently selected from nitrogen, oxygen, or sulfur. In some embodiments, R is an unsubstituted 5-6 membered heteroaryl ring having 1-4 heteroatoms independently selected from nitrogen, oxygen, or sulfur.

In some embodiments, R is an optionally substituted 5-membered heteroaryl ring having 1-4 heteroatoms independently selected from nitrogen, oxygen or sulfur. In some embodiments, R is a substituted 5-membered heteroaryl ring having 1-4 heteroatoms independently selected from nitrogen, oxygen or sulfur. In some embodiments, R is an unsubstituted 5-membered heteroaryl ring having 1-4 heteroatoms independently selected from nitrogen, oxygen or sulfur. In some embodiments, R is an optionally substituted 6-membered heteroaryl ring having 1-4 heteroatoms independently selected from nitrogen, oxygen, or sulfur. In some embodiments, R is a substituted 6-membered heteroaryl ring having 1-4 heteroatoms independently selected from nitrogen, oxygen, or sulfur. In some embodiments, R is an unsubstituted 6-membered heteroaryl ring having 1-4 heteroatoms independently selected from nitrogen, oxygen, or sulfur.

In some embodiments, R is an optionally substituted 5-membered heteroaryl ring having one heteroatom selected from nitrogen, oxygen, or sulfur. In some embodiments, R is selected from optionally substituted pyrrolyl, furanyl, or thienyl. In some embodiments, R is optionally substituted pyrrolyl. In some embodiments, R is optionally substituted furanyl. In some embodiments, R is optionally substituted thienyl.

In some embodiments, R is an optionally substituted 5-membered heteroaryl ring having two heteroatoms independently selected from nitrogen, oxygen, or sulfur. In certain embodiments, R is an optionally substituted 5-membered heteroaryl ring having one nitrogen atom, and an additional heteroatom selected from sulfur or oxygen.

Exemplary R groups include but are not limited to optionally substituted pyrazolyl, imidazolyl, thiazolyl, isothiazolyl, oxazolyl or isoxazolyl. In some embodiments, R is optionally substituted pyrazolyl.

In some embodiments, R is an optionally substituted 5-membered heteroaryl ring having three heteroatoms independently selected from nitrogen, oxygen, or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, or sulfur. Exemplary R groups include but are not limited to optionally substituted tetrazolyl, oxatriazolyl and thiatriazolyl.

In some embodiments, R is a 6-membered heteroaryl ring having 1-4 nitrogen atoms. In some embodiments, R is a 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl. In some embodiments, R is optionally substituted pyridinyl. In some embodiments, R is pyridinyl. In some embodiments, R is

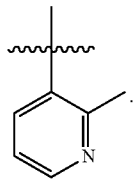

In some embodiments, R is a 7-10 membered bicyclic saturated or partially unsaturated heterocyclic ring having 1-5 heteroatoms independently selected from nitrogen, oxygen or sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an 8-10 membered bicyclic heteroaryl ring having 1-5 heteroatoms independently selected from nitrogen, oxygen or sulfur.

In some embodiments, R is an optionally substituted 5,6-fused heteroaryl ring having 1-5 heteroatoms independently selected from nitrogen, oxygen or sulfur. In some embodiments, R is an optionally substituted 5,6-fused heteroaryl ring having 1-4 heteroatoms independently selected from nitrogen, oxygen or sulfur. In some embodiments, R is an optionally substituted 5,6-fused heteroaryl ring having 1-3 heteroatoms independently selected from nitrogen, oxygen or sulfur. In some embodiments, R is an optionally substituted 5,6-fused heteroaryl ring having two heteroatoms independently selected from nitrogen, oxygen or sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen or sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen or sulfur. In some embodiments, R is an optionally substituted 5,6-fused heteroaryl ring having five heteroatoms independently selected from nitrogen, oxygen or sulfur.

In some embodiments, R is an optionally substituted 5,6-fused heteroaryl ring having 1-5 heteroatoms independently selected from nitrogen, oxygen or sulfur. In other embodiments, R is an optionally substituted 5,6-fused heteroaryl ring having 1-2 heteroatoms independently selected from nitrogen, oxygen or sulfur. In certain embodiments, R is an optionally substituted 5,6-fused heteroaryl ring having one heteroatom independently selected from nitrogen, oxygen or sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen or sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen or sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen or sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen or sulfur.

In certain embodiments, R is an optionally substituted 6,6-fused heteroaryl ring having 1-5 heteroatoms independently selected from nitrogen, oxygen or sulfur. In some embodiments, R is an optionally substituted 6,6-fused heteroaryl ring having 1-2 heteroatoms independently selected from nitrogen, oxygen or sulfur. In other embodiments, R is an optionally substituted 6,6-fused heteroaryl ring having one heteroatom selected from nitrogen, oxygen or sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen or sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen or sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen or sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen or sulfur.

As defined generally above, $R^2$ of formula I is R, halo, —$NH_2$, —CN, —$NO_2$, —$CF_3$, —C(O)-$L^3$-$R^z$, —C(O)N(R)-$L^3$-$R^z$, —C(O)N(R)—C(R)$_2$-$L^3$-$R^z$, —C(O)O-$L^3$-$R^z$ or —C(O)S-$L^3$-$R^z$.

In some embodiments, $R^2$ is any of the embodiments for R as described herein. In some embodiments, $R^2$ is halogen. In some embodiments, $R^2$ is —F. In some embodiments, $R^2$ is —Cl. In some embodiments, $R^2$ is —Br. In some embodiments, $R^2$ is —I. In some embodiments, $R^2$ is —$NH_2$. In some embodiments, $R^2$ is —CN. In some embodiments, $R^2$ is —$NO_2$. In some embodiments, $R^2$ is —$CF_3$.

In some embodiments, $R^2$ is —C(O)N(R)-$L^3$-$R^z$ or —C(O)N(R)—C(R)$_2$-$L^3$-$R^z$, wherein the R group attached to the nitrogen atom and $R^1$ are optionally taken together with their intervening atoms to form an optionally substituted 4-8 membered saturated, partially unsaturated or aryl ring having 2-4 heteroatoms independently selected from nitrogen, oxygen, or sulfur. In some embodiments, $R^2$ is —C(O)N(R)-$L^3$-$R^z$, wherein the R group attached to the nitrogen atom and $R^1$ are optionally taken together with their intervening atoms to form an optionally substituted 4-8 membered saturated, partially unsaturated or aryl ring having 2-4 heteroatoms independently selected from nitrogen, oxygen, or sulfur. In some embodiments, $R^2$ is —C(O)N(R)—C(R)$_2$-$L^3$-$R^z$, wherein the R group attached to the nitrogen atom and $R^1$ are optionally taken together with their intervening atoms to form an optionally substituted 4-8 membered saturated, partially unsaturated or aryl ring having 2-4 heteroatoms independently selected from nitrogen, oxygen, or sulfur.

In some embodiments, $R^2$ is —C(O)-$L^3$-$R^z$. In some embodiments, $R^2$ is —C(O)N(R)-$L^3$-$R^z$. In some embodiments, $R^2$ is —C(O)N(R)—C(R)$_2$-$L^3$-$R^z$. In some embodiments, $R^2$ is —C(O)O-$L^3$-$R^z$. In some embodiments, $R^2$ is —C(O)S-$L^3$-$R^z$.

As generally defined above, $L^3$ of formula I is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is selected from a covalent bond or an optionally substituted bivalent straight or branched $C_{1-8}$ hydrocarbon chain wherein one or more methylene units are optionally and independently replaced with -Cy-, —O—, —S—, —N(R)—, —N(R)C(O)—, —C(O)—, —C(O)N(R)—, or —S(O)—. In some embodiments, $L^3$ is selected from a covalent bond or an optionally substituted bivalent straight or branched $C_{1-8}$ hydrocarbon chain wherein one or more methylene units are optionally and independently replaced with -Cy-, —O—, —N(R)—, —N(R)C(O)—, —C(O)—, or —C(O)N(R)—. $L^3$ is selected from a covalent bond or an optionally substituted bivalent straight or branched $C_{1-8}$ hydrocarbon chain wherein one or more methylene units are optionally and independently replaced with -Cy- or —O—.

In some embodiments, $L^3$ is a covalent bond. In some embodiments, $L^3$ is an optionally substituted bivalent straight or branched $C_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted methylene group or -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_2$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_3$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_4$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_5$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_6$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_7$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_8$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—.

In some embodiments, $L^3$ is an optionally substituted bivalent straight or branched $C_{1-8}$ hydrocarbon chain wherein one or more methylene units are independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, $L^3$ is an optionally substituted bivalent straight or branched $C_{1-8}$ hydrocarbon chain wherein one or more methylene units are independently replaced with -Cy-, —O—, —S—, —N(R)—, —N(R)C(O)—, —C(O)—, —C(O)N(R)—, or —S(O)—. In some embodiments, $L^3$ is an optionally substituted bivalent straight or branched $C_{1-8}$ hydrocarbon chain wherein one or more methylene units are independently replaced with -Cy-, —O—, —N(R)—, —N(R)C(O)—, —C(O)—, or —C(O)N(R)—. In some embodiments, $L^3$ is an optionally substituted bivalent straight or branched $C_{1-8}$ hydrocarbon chain wherein one or more methylene units are independently replaced with -Cy- or —O—.

In some embodiments, $L^3$ is an optionally substituted bivalent straight or branched $C_{1-8}$ hydrocarbon chain. In some embodiments, $L^3$ is a bivalent straight or branched $C_{1-8}$ hydrocarbon chain. In some embodiments, $L^3$ is a bivalent straight $C_{1-8}$ hydrocarbon chain.

In some embodiments, one or more methylene units of $L^3$ are optionally and independently replaced with -Cy-, —O—, —S—, —N(R)—, —N(R)C(O)—, —C(O)—, —C(O)N(R)—, or —S(O)—.

In some embodiments, $R^2$ is —C(O)-$L^3$-$R^z$, —C(O)N(R)-$L^3$-$R^z$, —C(O)N(R)—C(R)$_2$-$L^3$-$R^z$, —C(O)O-$L^3$-$R^z$ or —C(O)S-$L^3$-$R^z$, wherein the methylene unit of $L^3$ that is directly bonded to said —C(O)—, —C(O)N(R)—, —C(O)N(R)—C(R)$_2$—, —C(O)O— or —C(O)S— moiety is optionally and independently replaced by -Cy-, —O—, —S—, —N(R)—, —N(R)C(O)—, —C(O)—, —C(O)N(R)—, or —S(O)—. In some embodiments, one or more methylene units of $L^3$ are optionally and independently replaced with -Cy-, —O—, —N(R)—, —N(R)C(O)—, —C(O)—, or —C(O)N(R)—. In some embodiments, $R^2$ is —C(O)-$L^3$-$R^z$, —C(O)N(R)-$L^3$-$R^z$, —C(O)N(R)—C(R)$_2$-$L^3$-$R^z$, —C(O)O-$L^3$-$R^z$ or —C(O)S-$L^3$-$R^z$, wherein the methylene unit of $L^3$ that is directly bonded to said —C(O)—, —C(O)N(R)—, —C(O)N(R)—C(R)$_2$—, —C(O)O— or —C(O)S— moiety is optionally and independently replaced by -Cy-, —O—, —N(R)—, —N(R)C(O)—, —C(O)—, or —C(O)N(R)—. In some embodiments, one or more methylene units of $L^3$ are optionally and independently replaced with -Cy- or —O—. In some embodiments, $R^2$ is —C(O)-$L^3$-$R^z$, —C(O)N(R)-$L^3$-$R^z$, —C(O)N(R)—C(R)$_2$-$L^3$-$R^z$, —C(O)O-$L^3$-$R^z$ or —C(O)S-$L^3$-$R^z$, wherein the methylene unit of $L^3$ that is directly bonded to said —C(O)—, —C(O)N(R)—, —C(O)N(R)—C(R)$_2$—, —C(O)O— or —C(O)S— moiety is optionally and independently replaced by -Cy- or —O—.

In some embodiments, one or more methylene units are independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—. In some embodiments, one or more methylene units are replaced with -Cy-. In some embodiments, one or more methylene units are replaced with —O—. In some embodiments, one or more methylene units are replaced with —S—. In some embodiments, one or more methylene units are replaced with —N(R)—. In some embodiments, one or more methylene units are replaced with —N(R)C(O)—. In some embodiments, one or more methylene units are replaced with —N(R)S(O)$_2$—. In some embodiments, one or more methylene units are replaced with —C(O)—. In some embodiments, one or more methylene units are replaced with —C(O)N(R)—. In some embodiments, one or more methylene units are replaced with —S(O)—. In some embodiments, one or more methylene units are replaced with —S(O)$_2$—. In some embodiments, one or more methylene units are replaced with —S(O)$_2$N(R)—.

In some embodiments, the methylene unit of $L^3$ that is directly bonded to $R^z$ is optionally replaced with -Cy-. In some embodiments, the methylene unit of $L^3$ that is directly bonded to $R^z$ is replaced with -Cy-. In some embodiments, the methylene unit of $L^3$ that is directly bonded to $R^z$ is replaced with an optionally substituted phenylene. In some embodiments, the methylene unit of $L^3$ that is directly bonded to $R^z$ is replaced with an optionally substituted 5-6 membered heteroarylene having 1-4 heteroatoms independently selected from nitrogen, oxygen, or sulfur.

In some embodiments, $L^3$ is —NRS(O)$_2$(CH$_2$)$_2$N(R)C(O)—.

As generally defined above, $R^z$ of formula I is hydrogen, R, —OR, —SR, —S(O)R, —S(O)$_2$R, —S(O)$_2$N(R)$_2$, —N(R)$_2$, —C(O)N(R)$_2$, —C(O)R, —C(O)OR, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^3$, or is selected from:

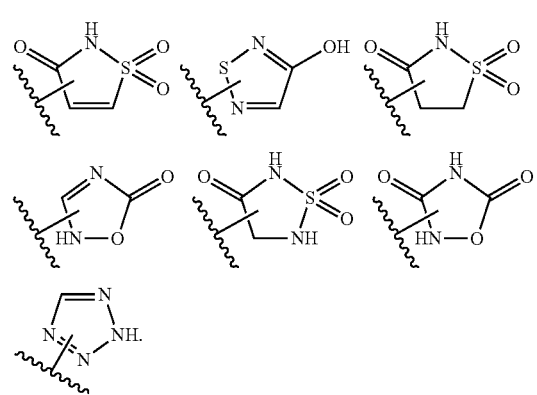

In some embodiments, $R^z$ is —OR, —SR, —S(O)R, —S(O)$_2$R, —S(O)$_2$N(R)$_2$, —N(R)$_2$, —C(O)N(R)$_2$, —C(O)R, —C(O)OR, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^3$, or is selected from:

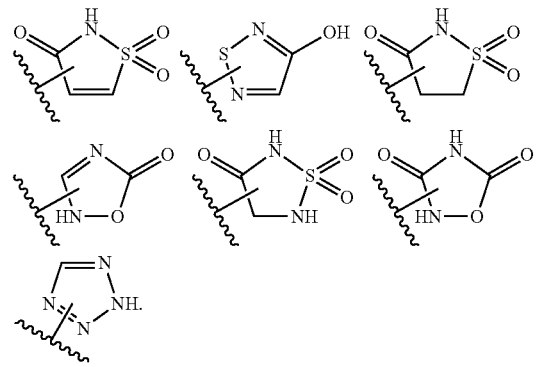

In some embodiments, $R^z$ is —S(O)R, —S(O)$_2$R, —S(O)$_2$N(R)$_2$, —N(R)$_2$, —C(O)N(R)$_2$, —C(O)R, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^3$, or is selected from:

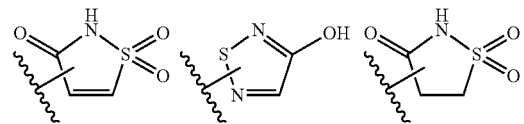

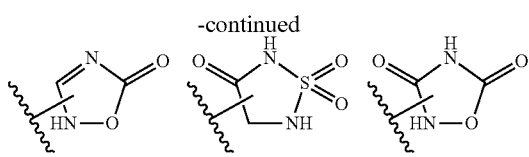

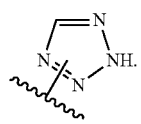

In some embodiments, $R^z$ is —S(O)$_2$N(R)$_2$, —C(O)N(R)$_2$, —C(O)OH, —C(O)R$^x$, —S(O)$_2$OH, or —S(O)$_2$R$^3$, or is selected from:

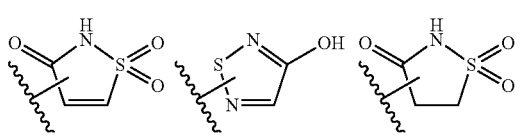

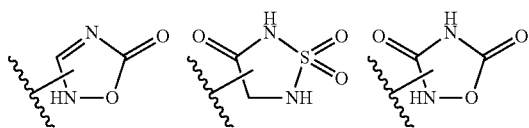

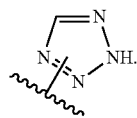

In some embodiments, $R^z$ is —S(O)$_2$N(R)$_2$, —C(O)N(R)$_2$, —C(O)OH, —C(O)R$^x$, —S(O)$_2$OH, or —S(O)$_2$R$^y$. In some embodiments, $R^z$ is —COOH, —C(O)N(R)SO$_2$R or —SO$_2$N(R)C(O)R. In some embodiments, $R^z$ is —COOH, —C(O)NHSO$_2$R or —SO$_2$NHC(O)R.

In some embodiments, $R^z$ is hydrogen. In some embodiments, $R^z$ is not hydrogen.

In some embodiments, $R^z$ is R. In some embodiments, $R^z$ is R, wherein R is not hydrogen.

In some embodiments, $R^z$ is —OR. In some embodiments, $R^z$ is —SR. In some embodiments, $R^z$ is —S(O)R. In some embodiments, $R^z$ is —S(O)$_2$R. In some embodiments, $R^z$ is —S(O)$_2$N(R)$_2$. In some embodiments, $R^z$ is —N(R)$_2$. In some embodiments, $R^z$ is C(O)N(R)$_2$. In some embodiments, $R^z$ is —C(O)R. In some embodiments, $R^z$ is —C(O)OR. In some embodiments, $R^z$ is —N(R)C(O)R. In some embodiments, $R^z$ is —N(R)C(O)OR. In some embodiments, $R^z$ is —N(R)C(O)N(R)$_2$. In some embodiments, $R^z$ is —N(R)S(O)$_2$R. In some embodiments, $R^z$ is —N(R)S(O)$_2$N(R)$_2$.

In some embodiments, $R^z$ is —C(O)OH.

In some embodiments, $R^z$ is —C(O)R$^x$. In some embodiments, $R^z$ is —C(O)N(R)S(O)$_2$R. In some embodiments, $R^z$ is —C(O)NHS(O)$_2$R. In some embodiments, $R^z$ is —C(O)N(R)S(O)$_2$R, wherein R is not hydrogen. In some embodiments, $R^z$ is —C(O)NHS(O)$_2$R, wherein R is not hydrogen. In some embodiments, $R^z$ is —C(O)N(R)S(O)$_2$R, wherein R is optionally substituted C$_{1-6}$ aliphatic. In some embodiments, $R^z$ is —C(O)NHS(O)$_2$R, wherein R is optionally substituted C$_{1-6}$ aliphatic. In some embodiments, $R^z$ is —C(O)N(R)S(O)$_2$Me. In some embodiments, $R^z$ is —C(O)NHS(O)$_2$Me. In some embodiments, $R^z$ is

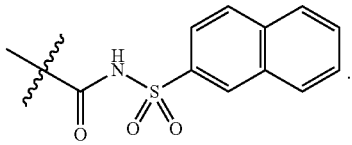 [SMILES: *C(=O)NS(=O)(=O)c1ccc2ccccc2c1]

In some embodiments, $R^z$ is

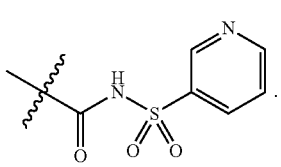 [SMILES: *C(=O)NS(=O)(=O)c1cccnc1]

In some embodiments, $R^z$ is

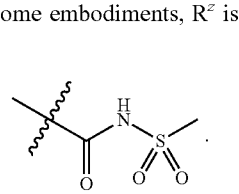

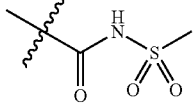

In some embodiments, $R^z$ is

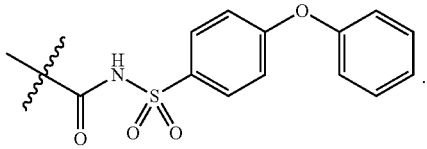 [SMILES: *C(=O)NS(=O)(=O)c1ccc(Oc2ccccc2)cc1]

In some embodiments, $R^z$ is

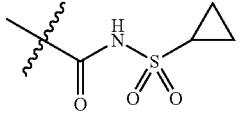

In some embodiments, $R^z$ is

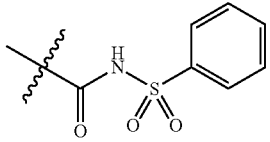

In some embodiments, $R^z$ is

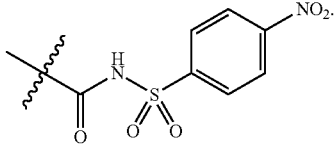 [SMILES: *C(=O)NS(=O)(=O)c1ccc([N+](=O)[O-])cc1]

In some embodiments, $R^z$ is

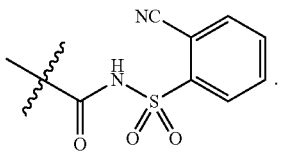 [SMILES: *C(=O)NS(=O)(=O)c1ccccc1C#N]

In some embodiments, $R^z$ is

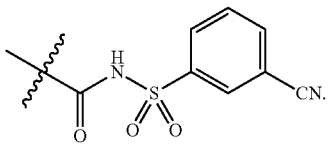 [SMILES: *C(=O)NS(=O)(=O)c1cccc(C#N)c1]

In some embodiments, $R^z$ is

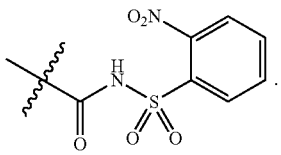 [SMILES: *C(=O)NS(=O)(=O)c1ccccc1[N+](=O)[O-]]

In some embodiments, $R^z$ is

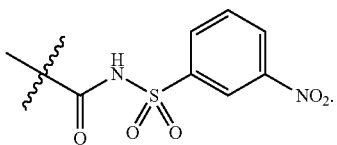 [SMILES: *C(=O)NS(=O)(=O)c1cccc([N+](=O)[O-])c1]

In some embodiments, $R^z$ is —S(O)$_2$OH.

In some embodiments, $R^z$ is —S(O)$_2$R$^y$. In some embodiments, $R^z$ is —S(O)$_2$N(R)C(O)R. In some embodiments, $R^z$ is —S(O)$_2$NHC(O)R. In some embodiments, $R^z$ is —S(O)$_2$N(R)C(O)R, wherein R is not hydrogen. In some embodiments, $R^z$ is S(O)$_2$NHC(O)R, wherein R is not hydrogen. In some embodiments, $R^z$ is —S(O)$_2$N(R)C(O)R, wherein R is optionally substituted C$_{1-6}$ aliphatic. In some embodiments, $R^z$ is —S(O)$_2$NHC(O)R, wherein R is optionally substituted C$_{1-6}$ aliphatic. In some embodiments, $R^z$ is —S(O)$_2$N(R)C(O)Me. In some embodiments, $R^z$ is —S(O)$_2$NHC(O)Me. In some embodiments, $R^z$ is —S(O)$_2$NHC(O)Me. In some embodiments, $R^z$ is

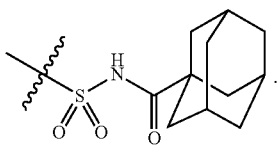 [SMILES: *S(=O)(=O)NC(=O)C12CC3CC(CC(C3)C1)C2]

In some embodiments, $R^z$ is

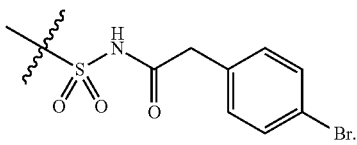 [SMILES: *S(=O)(=O)NC(=O)Cc1ccc(Br)cc1]

In some embodiments, $R^z$ is

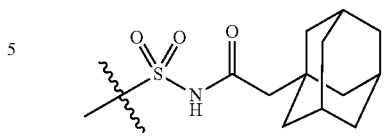

In some embodiments, $R^z$ is selected from:

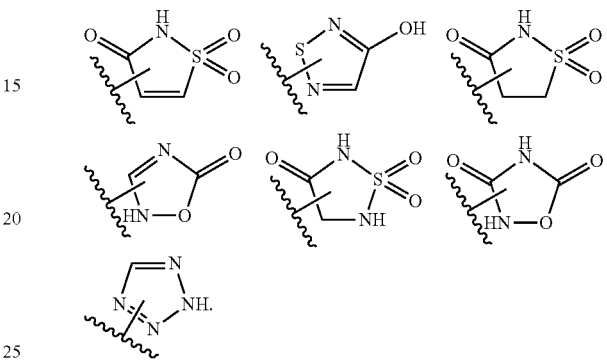

an optionally substituted bivalent straight or branched C$_{3-6}$ hydrocarbon chain wherein one or two methylene units of L$^2$ are optionally and independently replaced with —O—, —S—, or —N(R')—, and wherein two substituents of L$^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur As defined generally above, L$^2$ of formula I is an optionally substituted bivalent straight or branched C$_{3-6}$ hydrocarbon chain wherein one or two methylene units of L$^2$ are optionally and independently replaced with —O—, —S—, or —N(R')—, and wherein two substituents of L$^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur. In some embodiments, L$^2$ is an optionally substituted bivalent straight or branched C$_{3-6}$ hydrocarbon chain wherein one or two methylene units of L$^2$ are optionally and independently replaced with —O—, —S—, or —N(R')—. In some embodiments, two substituents of L$^2$ are optionally taken together to form an optionally substituted bivalent ring selected from 3-8 membered saturated or partially unsaturated carbocyclylene or 3-8 membered saturated or partially unsaturated heterocyclylene having 1-4 heteroatoms independently selected from nitrogen, oxygen, or sulfur. In some embodiments, two substituents of L$^2$ are optionally taken together to form optionally substituted bivalent 3-8 membered saturated or partially unsaturated carbocyclylene. In some embodiments, two substituents of L$^2$ are optionally taken together to form optionally substituted bivalent 3-8 membered saturated or partially unsaturated heterocyclylene having 1-4 heteroatoms independently selected from nitrogen, oxygen, or sulfur. In some embodiments, L$^2$ is a substituted bivalent C$_{3-6}$ hydrocarbon chain wherein one or two methylene units of L$^2$ are optionally and independently replaced with —O—, —S—, or —N(R')—. In some embodiments, $L^2$ is an unsubstituted bivalent $C_{3-6}$ hydrocarbon chain wherein one or two methylene units of $L^2$ are optionally and independently replaced with —O—, —S—, or —N(R')—. In some embodiments, $L^2$ is a substituted bivalent $C_{3-6}$ hydrocarbon. In some embodiments, $L^2$ is an unsubstituted bivalent $C_{3-6}$ hydrocarbon. In some embodiments, $L^2$ is an optionally substituted bivalent $C_{4-6}$ hydrocarbon chain wherein one or two methylene units of $L^2$ are optionally and independently replaced with —O—, —S—, or —N(R')—. In some embodiments, $L^2$ is a substituted bivalent $C_{4-6}$ hydrocarbon chain wherein one or two methylene units of $L^2$ are optionally and independently replaced with —O—, —S—, or —N(R')—. In some embodiments, $L^2$ is an unsubstituted bivalent $C_{4-6}$ hydrocarbon chain wherein one or two methylene units of $L^2$ are optionally and independently replaced with —O—, —S—, or —N(R')—. In some embodiments, $L^2$ is a substituted bivalent $C_{4-6}$ hydrocarbon. In some embodiments, $L^2$ is an unsubstituted bivalent $C_{4-6}$ hydrocarbon. In some embodiments, $L^2$ is an optionally substituted bivalent $C_5$-6 hydrocarbon chain wherein one or two methylene units of $L^2$ are optionally and independently replaced with —O—, —S—, or —N(R')—. In some embodiments, $L^2$ is a substituted bivalent $C_5$-6 hydrocarbon chain wherein one or two methylene units of $L^2$ are optionally and independently replaced with —O—, —S—, or —N(R')—. In some embodiments, $L^2$ is an unsubstituted bivalent $C_5$-6 hydrocarbon chain wherein one or two methylene units of $L^2$ are optionally and independently replaced with —O—, —S—, or —N(R')—. In some embodiments, $L^2$ is a substituted bivalent $C_5$-6 hydrocarbon. In some embodiments, $L^2$ is an unsubstituted bivalent $C_{5-6}$ hydrocarbon.

In some embodiments, $L^2$ is an optionally substituted bivalent $C_3$ hydrocarbon chain wherein one or two methylene units of $L^2$ are optionally and independently replaced with —O—, —S—, or —N(R')—. In some embodiments, $L^2$ is a substituted bivalent $C_3$ hydrocarbon chain wherein one or two methylene units of $L^2$ are optionally and independently replaced with —O—, —S—, or —N(R')—. In some embodiments, $L^2$ is an unsubstituted bivalent $C_3$ hydrocarbon chain wherein one or two methylene units of $L^2$ are optionally and independently replaced with —O—, —S—, or —N(R')—. In some embodiments, $L^2$ is a substituted bivalent $C_3$ hydrocarbon chain. In some embodiments, $L^2$ is an unsubstituted bivalent $C_3$ hydrocarbon chain.

In some embodiments, $L^2$ is an optionally substituted bivalent $C_4$ hydrocarbon chain wherein one or two methylene units of $L^2$ are optionally and independently replaced with —O—, —S—, or —N(R')—. In some embodiments, $L^2$ is a substituted bivalent $C_4$ hydrocarbon chain wherein one or two methylene units of $L^2$ are optionally and independently replaced with —O—, —S—, or —N(R')—. In some embodiments, $L^2$ is an unsubstituted bivalent $C_4$ hydrocarbon chain wherein one or two methylene units of $L^2$ are optionally and independently replaced with —O—, —S—, or —N(R')—. In some embodiments, $L^2$ is a substituted bivalent $C_4$ hydrocarbon chain. In some embodiments, $L^2$ is an unsubstituted bivalent $C_4$ hydrocarbon chain.

In some embodiments, $L^2$ is an optionally substituted bivalent $C_5$ hydrocarbon chain wherein one or two methylene units of $L^2$ are optionally and independently replaced with —O—, —S—, or —N(R')—. In some embodiments, $L^2$ is a substituted bivalent $C_5$ hydrocarbon chain wherein one or two methylene units of $L^2$ are optionally and independently replaced with —O—, —S—, or —N(R')—. In some embodiments, $L^2$ is an unsubstituted bivalent $C_5$ hydrocarbon chain wherein one or two methylene units of $L^2$ are optionally and independently replaced with —O—, —S—, or —N(R')—. In some embodiments, $L^2$ is a substituted bivalent $C_5$ hydrocarbon chain. In some embodiments, $L^2$ is an unsubstituted bivalent $C_5$ hydrocarbon chain.

In some embodiments, $L^2$ is an optionally substituted bivalent $C_6$ hydrocarbon chain wherein one or two methylene units of $L^2$ are optionally and independently replaced with —O—, —S—, or —N(R')—. In some embodiments, $L^2$ is a substituted bivalent $C_6$ hydrocarbon chain wherein one or two methylene units of $L^2$ are optionally and independently replaced with —O—, —S—, or —N(R')—. In some embodiments, $L^2$ is an unsubstituted bivalent $C_6$ hydrocarbon chain wherein one or two methylene units of $L^2$ are optionally and independently replaced with —O—, —S—, or —N(R')—. In some embodiments, $L^2$ is a substituted bivalent $C_6$ hydrocarbon chain. In some embodiments, $L^2$ is an unsubstituted bivalent $C_6$ hydrocarbon chain.

In some embodiments, two substituents of $L^2$ are optionally taken together to form optionally substituted bivalent 3-8 membered saturated or partially unsaturated carbocyclylene. In some embodiments, two substituents of $L^2$ are taken together to form optionally substituted bivalent 3-8 membered saturated or partially unsaturated carbocyclylene. In some embodiments, two substituents of $L^2$ are optionally taken together to form optionally substituted bivalent 3-8 membered saturated carbocyclylene. In some embodiments, two substituents of $L^2$ are taken together to form optionally substituted bivalent 3-8 membered saturated carbocyclylene. In some embodiments, two substituents of $L^2$ are optionally taken together to form optionally substituted bivalent 3-8 membered partially unsaturated carbocyclylene. In some embodiments, two substituents of $L^2$ are taken together to form optionally substituted bivalent 3-8 membered partially unsaturated carbocyclylene.

In some embodiments, two substituents of $L^2$ are taken together to form optionally substituted bivalent 3-membered saturated or partially unsaturated carbocyclylene. In some embodiments, two substituents of $L^2$ are taken together to form optionally substituted bivalent 3-membered saturated carbocyclylene. In some embodiments, two substituents of $L^2$ are taken together to form optionally substituted bivalent 3-membered partially unsaturated carbocyclylene. In some embodiments, two substituents of $L^2$ are taken together to form optionally substituted bivalent 4-membered saturated or partially unsaturated carbocyclylene. In some embodiments, two substituents of $L^2$ are taken together to form optionally substituted bivalent 4-membered saturated carbocyclylene. In some embodiments, two substituents of $L^2$ are taken together to form optionally substituted bivalent 4-membered partially unsaturated carbocyclylene. In some embodiments, two substituents of $L^2$ are taken together to form optionally substituted bivalent 5-membered saturated or partially unsaturated carbocyclylene. In some embodiments, two substituents of $L^2$ are taken together to form optionally substituted bivalent 5-membered saturated carbocyclylene. In some embodiments, two substituents of $L^2$ are taken together to form optionally substituted bivalent 5-membered partially unsaturated carbocyclylene. In some embodiments, two substituents of $L^2$ are taken together to form optionally substituted bivalent 6-membered saturated or partially unsaturated carbocyclylene. In some embodiments, two substituents of $L^2$ are taken together to form optionally substituted bivalent 6-membered saturated carbocyclylene. In some embodiments, two substituents of $L^2$ are taken together to form optionally substituted bivalent 6-membered partially unsaturated carbocyclylene. In some embodiments, two substituents of $L^2$ are taken together to form optionally substituted bivalent 7-membered saturated or partially unsaturated carbocyclylene. In some embodiments, two substituents of $L^2$ are taken together to form optionally substituted bivalent 7-membered saturated carbocyclylene. In some embodiments, two substituents of $L^2$ are taken together to form optionally substituted bivalent 7-membered partially unsaturated carbocyclylene. In some embodiments, two substituents of $L^2$ are taken together to form optionally substituted bivalent 8-membered saturated or partially unsaturated carbocyclylene. In some embodiments, two substituents of $L^2$ are taken together to form optionally substituted bivalent 8-membered saturated carbocyclylene. In some embodiments, two substituents of $L^2$ are taken together to form optionally substituted bivalent 8-membered partially unsaturated carbocyclylene.

In some embodiments, two substituents of $L^2$ are optionally taken together to form optionally substituted bivalent 3-8 membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-8 membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-8 membered saturated heterocyclylene having 1-4 heteroatoms independently selected from nitrogen, oxygen, or sulfur. In some embodiments, two substituents of $L^2$ are taken together to form optionally substituted bivalent 3-8 membered partially unsaturated heterocyclylene having 1-4 heteroatoms independently selected from nitrogen, oxygen, or sulfur.

In some embodiments, two substituents of $L^2$ are taken together to form optionally substituted bivalent 3-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 3-membered saturated heterocyclylene having 1-4 heteroatoms independently selected from nitrogen, oxygen, or sulfur. In some embodiments, two substituents of $L^2$ are taken together to form optionally substituted bivalent 3-membered partially unsaturated heterocyclylene having 1-4 heteroatoms independently selected from nitrogen, oxygen, or sulfur. In some embodiments, two substituents of $L^2$ are taken together to form optionally substituted bivalent 4-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 4-membered saturated heterocyclylene having 1-4 heteroatoms independently selected from nitrogen, oxygen, or sulfur. In some embodiments, two substituents of $L^2$ are taken together to form optionally substituted bivalent 4-membered partially unsaturated heterocyclylene having 1-4 heteroatoms independently selected from nitrogen, oxygen, or sulfur. In some embodiments, two substituents of $L^2$ are taken together to form optionally substituted bivalent 5-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 5-membered saturated heterocyclylene having 1-4 heteroatoms independently selected from nitrogen, oxygen, or sulfur. In some embodiments, two substituents of $L^2$ are taken together to form optionally substituted bivalent 5-membered partially unsaturated heterocyclylene having 1-4 heteroatoms independently selected from nitrogen, oxygen, or sulfur. In some embodiments, two substituents of $L^2$ are taken together to form optionally substituted bivalent 6-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 6-membered saturated heterocyclylene having 1-4 heteroatoms independently selected from nitrogen, oxygen, or sulfur. In some embodiments, two substituents of $L^2$ are taken together to form optionally substituted bivalent 6-membered partially unsaturated heterocyclylene having 1-4 heteroatoms independently selected from nitrogen, oxygen, or sulfur. In some embodiments, two substituents of $L^2$ are taken together to form optionally substituted bivalent 7-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 7-membered saturated heterocyclylene having 1-4 heteroatoms independently selected from nitrogen, oxygen, or sulfur. In some embodiments, two substituents of $L^2$ are taken together to form optionally substituted bivalent 7-membered partially unsaturated heterocyclylene having 1-4 heteroatoms independently selected from nitrogen, oxygen, or sulfur. In some embodiments, two substituents of $L^2$ are taken together to form optionally substituted bivalent 8-membered saturated or partially unsaturated heterocyclylene having 1-4 heteroatoms independently selected from nitrogen, oxygen, or sulfur. In some embodiments, two substituents of $L^2$ are taken together to form optionally substituted bivalent 8-membered saturated heterocyclylene having 1-4 heteroatoms independently selected from nitrogen, oxygen, or sulfur. In some embodiments, two substituents of $L^2$ are taken together to form optionally substituted bivalent 8-membered partially unsaturated heterocyclylene having 1-4 heteroatoms independently selected from nitrogen, oxygen, or sulfur.

In some embodiments, two substituents of $L^2$ are taken together to form optionally substituted bivalent 3-8 membered saturated or partially unsaturated heterocyclylene having one heteroatom selected from nitrogen, oxygen, or sulfur. In some embodiments, two substituents of $L^2$ are taken together to form optionally substituted bivalent 3-8 membered saturated or partially unsaturated heterocyclylene having two heteroatoms independently selected from nitrogen, oxygen, or sulfur. In some embodiments, two substituents of $L^2$ are taken together to form optionally substituted bivalent 3-8 membered saturated or partially unsaturated heterocyclylene having three heteroatoms independently selected from nitrogen, oxygen, or sulfur. In some embodiments, two substituents of $L^2$ are taken together to form optionally substituted bivalent 3-8 membered saturated or partially unsaturated heterocyclylene having four heteroatoms independently selected from nitrogen, oxygen, or sulfur.

In some embodiments, one or two methylene units of $L^2$ are replaced with —O—. In some embodiments, one methylene unit of $L^2$ is replaced with —O—. In some embodiments, $L^2$ is an optionally substituted bivalent $C_3$ hydrocarbon chain wherein one methylene unit of $L^2$ is replaced with —O—. In some embodiments, $L^2$ is a substituted bivalent $C_3$ hydrocarbon chain wherein one methylene unit of $L^2$ is replaced with —O—. In some embodiments, $L^2$ is an unsubstituted bivalent $C_3$ hydrocarbon chain wherein one methylene unit of $L^2$ is replaced with —O—. In some embodiments, $L^2$ is an optionally substituted bivalent $C_4$ hydrocarbon chain wherein one methylene unit of $L^2$ is replaced with —O—. In some embodiments, $L^2$ is a substituted bivalent $C_4$ hydrocarbon chain wherein one methylene unit of $L^2$ is replaced with —O—. In some embodiments, $L^2$ is an unsubstituted bivalent $C_4$ hydrocarbon chain wherein one methylene unit of $L^2$ is replaced with —O—. In some embodiments, $L^2$ is an optionally substituted bivalent $C_5$ hydrocarbon chain wherein one methylene unit of $L^2$ is replaced with —O—. In some embodiments, $L^2$ is a substituted bivalent $C_5$ hydrocarbon chain wherein one methylene unit of $L^2$ is replaced with —O—. In some embodiments, $L^2$ is an unsubstituted bivalent $C_5$ hydrocarbon chain wherein one methylene unit of $L^2$ is replaced with —O—. In some embodiments, $L^2$ is an optionally substituted bivalent $C_6$ hydrocarbon chain wherein one methylene unit of $L^2$ is replaced with —O—. In some embodiments, $L^2$ is a substituted bivalent $C_6$ hydrocarbon chain wherein one methylene unit of $L^2$ is replaced with —O—. In some embodiments, $L^2$ is an unsubstituted bivalent $C_6$ hydrocarbon chain wherein one methylene unit of $L^2$ is replaced with —O—.

In some embodiments, one or two methylene units of $L^2$ are replaced with —S—. In some embodiments, one methylene unit of $L^2$ is replaced with —S—. In some embodiments, $L^2$ is an optionally substituted bivalent $C_3$ hydrocarbon chain wherein one methylene unit of $L^2$ is replaced with —S—. In some embodiments, $L^2$ is a substituted bivalent $C_3$ hydrocarbon chain wherein one methylene unit of $L^2$ is replaced with —S—. In some embodiments, $L^2$ is an unsubstituted bivalent $C_3$ hydrocarbon chain wherein one methylene unit of $L^2$ is replaced with —S—. In some embodiments, $L^2$ is an optionally substituted bivalent $C_4$ hydrocarbon chain wherein one methylene unit of $L^2$ is replaced with —S—. In some embodiments, $L^2$ is a substituted bivalent $C_4$ hydrocarbon chain wherein one methylene unit of $L^2$ is replaced with —S—. In some embodiments, $L^2$ is an unsubstituted bivalent $C_4$ hydrocarbon chain wherein one methylene unit of $L^2$ is replaced with —S—. In some embodiments, $L^2$ is an optionally substituted bivalent $C_5$ hydrocarbon chain wherein one methylene unit of $L^2$ is replaced with —S—. In some embodiments, $L^2$ is a substituted bivalent $C_5$ hydrocarbon chain wherein one methylene unit of $L^2$ is replaced with —S—. In some embodiments, $L^2$ is an unsubstituted bivalent $C_5$ hydrocarbon chain wherein one methylene unit of $L^2$ is replaced with —S—. In some embodiments, $L^2$ is an optionally substituted bivalent $C_6$ hydrocarbon chain wherein one methylene unit of $L^2$ is replaced with —S—. In some embodiments, $L^2$ is a substituted bivalent $C_6$ hydrocarbon chain wherein one methylene unit of $L^2$ is replaced with —S—. In some embodiments, $L^2$ is an unsubstituted bivalent $C_6$ hydrocarbon chain wherein one methylene unit of $L^2$ is replaced with —S—.

In some embodiments, one or two methylene units of $L^2$ are replaced with —N(R')—. In some embodiments, one methylene unit of $L^2$ is replaced with —N(R')—. In some embodiments, $L^2$ is an optionally substituted bivalent $C_3$ hydrocarbon chain wherein one methylene unit of $L^2$ is replaced with —N(R')—. In some embodiments, $L^2$ is a substituted bivalent $C_3$ hydrocarbon chain wherein one methylene unit of $L^2$ is replaced with —N(R')—. In some embodiments, $L^2$ is an unsubstituted bivalent $C_3$ hydrocarbon chain wherein one methylene unit of $L^2$ is replaced with —N(R')—. In some embodiments, $L^2$ is an optionally substituted bivalent $C_4$ hydrocarbon chain wherein one methylene unit of $L^2$ is replaced with —N(R')—. In some embodiments, $L^2$ is a substituted bivalent $C_4$ hydrocarbon chain wherein one methylene unit of $L^2$ is replaced with —N(R')—. In some embodiments, $L^2$ is an unsubstituted bivalent $C_4$ hydrocarbon chain wherein one methylene unit of $L^2$ is replaced with —N(R')—. In some embodiments, $L^2$ is an optionally substituted bivalent $C_5$ hydrocarbon chain wherein one methylene unit of $L^2$ is replaced with —N(R')—. In some embodiments, $L^2$ is a substituted bivalent $C_5$ hydrocarbon chain wherein one methylene unit of $L^2$ is replaced with —N(R')—. In some embodiments, $L^2$ is an unsubstituted bivalent $C_5$ hydrocarbon chain wherein one methylene unit of $L^2$ is replaced with —N(R')—. In some embodiments, $L^2$ is an optionally substituted bivalent $C_6$ hydrocarbon chain wherein one methylene unit of $L^2$ is replaced with —N(R')—. In some embodiments, $L^2$ is a substituted bivalent $C_6$ hydrocarbon chain wherein one methylene unit of $L^2$ is replaced with —N(R')—. In some embodiments, $L^2$ is an unsubstituted bivalent $C_6$ hydrocarbon chain wherein one methylene unit of $L^2$ is replaced with —N(R')—.

In some embodiments, each substituent of $L^2$ is $C_{1-6}$ aliphatic. In some embodiments, each substituent of $L^2$ is $C_{1-6}$ alkyl. In some embodiments, each substituent of $L^2$ is methyl.

In some embodiments, $L^2$ is —$CH_2CH_2O$—. In some embodiments, -$L^2$-$R^3$ is —$CH_2CH_2O$—$R^3$. In some embodiments, $L^2$ is —$CH_2CH_2CH_2O$—. In some embodiments, -$L^2$-$R^3$ is —$CH_2CH_2CH_2O$—$R^3$. In some embodiments, -$L^2$-$R^3$ is In some embodiments, $L^2$ is —$CH_2CH(CH_3)CH_2O$—. In some embodiments, -$L^2$-$R^3$ is —$CH_2CH(CH_3)CH_2O$—$R^3$.

As defined generally above, each R' of formula I is independently hydrogen or optionally substituted $C_1$-4 alkyl. In some embodiments, R' is hydrogen. In some embodiments, R' is optionally substituted $C_{1-4}$ alkyl. In some embodiments, R' is substituted C1-4 alkyl. In some embodiments, R' is unsubstituted C1-4 alkyl. In some embodiments, R' is optionally substituted methyl. In some embodiments, R' is substituted methyl. In some embodiments, R' is methyl. In some embodiments, R' is optionally substituted ethyl. In some embodiments, R' is substituted ethyl. In some embodiments, R' is ethyl. In some embodiments, R' is optionally substituted propyl. In some embodiments, R' is optionally substituted n-propyl. In some embodiments, R' is optionally substituted isopropyl. In some embodiments, R' is substituted propyl. In some embodiments, R' is substituted n-propyl. In some embodiments, R' is substituted isopropyl. In some embodiments, R' is propyl. In some embodiments, R' is n-propyl. In some embodiments, R' is isopropyl. In some embodiments, R' is optionally substituted butyl. In some embodiments, R' is substituted butyl. In some embodiments, R' is butyl. In some embodiments, R' is optionally substituted n-butyl. In some embodiments, R' is substituted n-butyl. In some embodiments, R' is n-butyl. In some embodiments, R' is optionally substituted isobutyl. In some embodiments, R' is substituted isobutyl. In some embodiments, R' is isobutyl. In some embodiments, R' is optionally substituted sec-butyl. In some embodiments, R' is substituted sec-butyl. In some embodiments, R' is sec-butyl. In some embodiments, R' is optionally substituted t-butyl. In some embodiments, R' is substituted t-butyl. In some embodiments, R' is t-butyl.

As defined generally above, $R^3$ of formula I is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur. In some embodiments, $R^3$ is substituted. In some embodiments, $R^3$ is unsubstituted.

In some embodiments, $R^3$ is an optionally substituted 3-8 membered saturated or partially unsaturated monocyclic carbocyclic ring. In some embodiments, $R^3$ is an optionally substituted 3-membered saturated or partially unsaturated monocyclic carbocyclic ring. In some embodiments, $R^3$ is an optionally substituted 4-membered saturated or partially unsaturated monocyclic carbocyclic ring. In some embodiments, $R^3$ is an optionally substituted 5-membered saturated or partially unsaturated monocyclic carbocyclic ring. In some embodiments, $R^3$ is an optionally substituted 6-membered saturated or partially unsaturated monocyclic carbocyclic ring. In some embodiments, $R^3$ is an optionally substituted 7-membered saturated or partially unsaturated monocyclic carbocyclic ring. In some embodiments, $R^3$ is an optionally substituted 8-membered saturated or partially unsaturated monocyclic carbocyclic ring.

In some embodiments, $R^3$ is an optionally substituted 3-8 membered saturated monocyclic carbocyclic ring. In some embodiments, $R^3$ is an optionally substituted cycloheptyl. In some embodiments, $R^3$ is an optionally substituted cyclohexyl. In some embodiments, $R^3$ is an optionally substituted cyclopentyl. In some embodiments, $R^3$ is an optionally substituted cyclobutyl. In some embodiments, $R^3$ is an optionally substituted cyclopropyl.

In some embodiments, $R^3$ is an optionally substituted 3-8 membered unsaturated monocyclic carbocyclic ring. In some embodiments, $R^3$ is an optionally substituted cycloheptenyl. In some embodiments, $R^3$ is an optionally substituted cyclohexenyl. In some embodiments, $R^3$ is an optionally substituted cyclopentenyl. In some embodiments, $R^3$ is an optionally substituted cyclobutenyl.

In some embodiments, $R^3$ is optionally substituted phenyl. In some embodiments, $R^3$ is substituted phenyl. In some embodiments, $R^3$ is unsubstituted phenyl. In some embodiments, $R^3$ is 3,5-dimethyl-4-chlorophenyl.

In some embodiments, $R^3$ is an optionally substituted 8-10 membered bicyclic aromatic carbocyclic ring. In some embodiments, $R^3$ is a substituted 8-10 membered bicyclic aromatic carbocyclic ring. In some embodiments, $R^3$ is an unsubstituted 8-10 membered bicyclic aromatic carbocyclic ring. In some embodiments, $R^3$ is an optionally substituted 10-membered bicyclic aromatic carbocyclic ring. In some embodiments, $R^3$ is a substituted 10-membered bicyclic aromatic carbocyclic ring. In some embodiments, $R^3$ is an unsubstituted 10-membered bicyclic aromatic carbocyclic ring. In some embodiments, $R^3$ is optionally substituted naphthyl. In some embodiments, $R^3$ is substituted naphthyl. In some embodiments, $R^3$ is unsubstituted naphthyl. In some embodiments, $R^3$ is optionally substituted 1-naphthyl. In some embodiments, $R^3$ is 1-naphthyl. In some embodiments, $R^3$ is optionally substituted 2-naphthyl. In some embodiments, $R^3$ is 2-naphthyl.

In some embodiments, $R^3$ is an optionally substituted 3-8 membered saturated or partially unsaturated monocyclic heterocyclic ring having 1-2 heteroatoms independently selected from nitrogen, oxygen or sulfur. In some embodiments, $R^3$ is an optionally substituted 4-8 membered saturated or partially unsaturated monocyclic heterocyclic ring having 1-2 heteroatoms independently selected from nitrogen, oxygen or sulfur. In some embodiments, $R^3$ is a substituted 4-8 membered saturated or partially unsaturated monocyclic heterocyclic ring having 1-2 heteroatoms independently selected from nitrogen, oxygen or sulfur. In some embodiments, $R^3$ is an unsubstituted 4-8 membered saturated or partially unsaturated monocyclic heterocyclic ring having 1-2 heteroatoms independently selected from nitrogen, oxygen or sulfur.

In some embodiments, $R^3$ is an optionally substituted 3-8 membered saturated heterocyclic ring having 1-2 heteroatoms independently selected from nitrogen, oxygen or sulfur. In some embodiments, $R^3$ is an optionally substituted 4-8 membered saturated heterocyclic ring having 1-2 heteroatoms independently selected from nitrogen, oxygen or sulfur. In some embodiments, $R^3$ is a substituted 4-8 membered saturated heterocyclic ring having 1-2 heteroatoms independently selected from nitrogen, oxygen or sulfur. In some embodiments, $R^3$ is an unsubstituted 4-8 membered saturated heterocyclic ring having 1-2 heteroatoms independently selected from nitrogen, oxygen or sulfur.

In some embodiments, $R^3$ is an optionally substituted 3-membered saturated heterocyclic ring having one heteroatom selected from nitrogen, oxygen or sulfur. Exemplary $R^3$ groups include but are not limited to optionally substituted aziridinyl, thiiranyl or oxiranyl. In some embodiments, $R^3$ is a substituted 3-membered saturated heterocyclic ring having one heteroatom selected from nitrogen, oxygen or sulfur. In some embodiments, $R^3$ is an unsubstituted 3-membered saturated heterocyclic ring having one heteroatom selected from nitrogen, oxygen or sulfur.

In some embodiments, $R^3$ is an optionally substituted 4-membered saturated heterocyclic ring having 1-2 heteroatoms independently selected from nitrogen, oxygen, or sulfur. Exemplary $R^3$ groups include but are not limited to optionally substituted azetidinyl, oxetanyl, thietanyl, oxazetidinyl, thiazetidinyl, or diazetidinyl.

In some embodiments, $R^3$ is an optionally substituted 5-membered saturated heterocyclic ring having 1-2 heteroatoms independently selected from nitrogen, oxygen, or sulfur. Exemplary $R^3$ groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, or thiazolidinyl.

In some embodiments, $R^3$ is an optionally substituted 6-membered saturated heterocyclic ring having 1-2 heteroatoms independently selected from nitrogen, oxygen, or sulfur. Exemplary $R^3$ groups include but are not limited to optionally substituted piperidinyl, tetrahydropyranyl, tetrahydrothiopyranyl, piperazinyl, morpholinyl, thiomorpholinyl, dithianyl, dioxanyl, and oxathianyl.

In some embodiments, $R^3$ is optionally substituted 7-membered saturated heterocyclic ring having 1-2 heteroatoms independently selected from nitrogen, oxygen, or sulfur. Exemplary $R^3$ groups include but are not limited to optionally substituted azepanyl, oxepanyl, thiepanyl, diazepanyl, oxazepanyl, thiazepanyl, dioxepanyl, oxathiepanyl, or dithiepanyl.

In some embodiments, $R^3$ is optionally substituted 8-membered saturated heterocyclic ring having 1-2 heteroatoms independently selected from nitrogen, oxygen, or sulfur.

In some embodiments, $R^3$ is an optionally substituted 4-8 membered partially unsaturated heterocyclic ring having 1-2 heteroatoms independently selected from nitrogen, oxygen or sulfur. In certain embodiments, $R^3$ is an optionally substituted 5-7 membered partially unsaturated ring having 1-2 heteroatoms independently selected from nitrogen, oxygen, or sulfur. In certain embodiments, $R^3$ is an optionally substituted 5-6 membered partially unsaturated ring having 1-2 heteroatoms independently selected from nitrogen, oxygen, or sulfur. In certain embodiments, $R^3$ is an optionally substituted 5-membered partially unsaturated ring having 1-2 heteroatoms independently selected from nitrogen, oxygen, or sulfur. Exemplary $R^3$ groups include but are not limited to optionally substituted dihydroimidazolyl, dihydrothiazolyl, dihydrooxazolyl, or oxazolinyl. In certain embodiments, $R^3$ is an optionally substituted 6-membered partially unsaturated ring having 1-2 heteroatoms independently selected from nitrogen, oxygen, or sulfur. Exemplary $R^3$ groups include but are not limited to optionally substituted dihydropyridinyl, tetrahydropyridinyl, dihydropyrimidinyl, tetrahydropyrimidinyl, dihydropyrazinyl, tetrahydropyrazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, $R^3$ is an optionally substituted 7-membered partially unsaturated ring having 1-2 heteroatoms independently selected from nitrogen, oxygen, or sulfur. Exemplary $R^3$ groups include but are not limited to optionally substituted azepinyl, oxepinyl, thiepinyl, diazepinyl, oxazepinyl, thiazepinyl, triazepinyl, oxadiazepinyl, thiadiazepinyl, dihydroazepinyl, dihydrooxepinyl, dihydrothiepinyl, dihydrodiazepinyl, dihydrooxazepinyl, dihydrothiazepinyl, tetrahydroazepinyl, tetrahydrooxepinyl, tetrahydrothiepinyl, tetrahydrodiazepinyl, tetrahydrooxazepinyl or tetrahydrothiazepinyl. In some embodiments, $R^3$ is an optionally substituted 8-membered partially unsaturated ring having 1-2 heteroatoms independently selected from nitrogen, oxygen or sulfur.

In some embodiments, $R^3$ is an optionally substituted 5-6 membered monocyclic heteroaromatic ring having 1-4 heteroatoms independently selected from nitrogen, oxygen, or sulfur. In some embodiments, $R^3$ is a substituted 5-6 membered monocyclic heteroaromatic ring having 1-4 heteroatoms independently selected from nitrogen, oxygen, or sulfur. In some embodiments, $R^3$ is an unsubstituted 5-6 membered monocyclic heteroaromatic ring having 1-4 heteroatoms independently selected from nitrogen, oxygen, or sulfur.

In some embodiments, $R^3$ is an optionally substituted 5-membered monocyclic heteroaromatic ring having 1-4 heteroatoms independently selected from nitrogen, oxygen or sulfur. In some embodiments, $R^3$ is a substituted 5-membered monocyclic heteroaromatic ring having 1-4 heteroatoms independently selected from nitrogen, oxygen or sulfur. In some embodiments, $R^3$ is an unsubstituted 5-membered monocyclic heteroaromatic ring having 1-4 heteroatoms independently selected from nitrogen, oxygen or sulfur. In some embodiments, $R^3$ is an optionally substituted 6-membered monocyclic heteroaromatic ring having 1-4 heteroatoms independently selected from nitrogen, oxygen, or sulfur. In some embodiments, $R^3$ is a substituted 6-membered monocyclic heteroaromatic ring having 1-4 heteroatoms independently selected from nitrogen, oxygen or sulfur. In some embodiments, $R^3$ is an unsubstituted 6-membered monocyclic heteroaromatic ring having 1-4 heteroatoms independently selected from nitrogen, oxygen or sulfur.

In some embodiments, $R^3$ is an optionally substituted 5-membered heteroaryl ring having one heteroatom selected from nitrogen, oxygen, or sulfur. In some embodiments, $R^3$ is selected from optionally substituted pyrrolyl, furanyl, or thienyl.

In some embodiments, $R^3$ is an optionally substituted 5-membered heteroaryl ring having two heteroatoms independently selected from nitrogen, oxygen, or sulfur. In certain embodiments, $R^3$ is an optionally substituted 5-membered heteroaryl ring having one nitrogen atom, and an additional heteroatom selected from sulfur or oxygen. Exemplary $R^3$ groups include but are not limited to optionally substituted pyrazolyl, imidazolyl, thiazolyl, isothiazolyl, oxazolyl or isoxazolyl.

In some embodiments, $R^3$ is an optionally substituted 5-membered heteroaryl ring having three heteroatoms independently selected from nitrogen, oxygen, or sulfur. Exemplary $R^3$ groups include but are not limited to optionally substituted triazolyl, oxadiazolyl or thiadiazolyl.

In some embodiments, $R^3$ is an optionally substituted 5-membered heteroaryl ring having four heteroatoms independently selected from nitrogen, oxygen, or sulfur. Exemplary $R^3$ groups include but are not limited to optionally substituted tetrazolyl, oxatriazolyl and thiatriazolyl.

In some embodiments, $R^3$ is a 6-membered heteroaryl ring having 1-4 nitrogen atoms. In some embodiments, $R^3$ is a 6-membered heteroaryl ring having 1-3 nitrogen atoms. In other embodiments, $R^3$ is an optionally substituted 6-membered heteroaryl ring having 1-2 nitrogen atoms. In some embodiments, $R^3$ is an optionally substituted 6-membered heteroaryl ring having four nitrogen atoms. In some embodiments, $R^3$ is an optionally substituted 6-membered heteroaryl ring having three nitrogen atoms. In some embodiments, $R^3$ is an optionally substituted 6-membered heteroaryl ring having two nitrogen atoms. In certain embodiments, $R^3$ is an optionally substituted 6-membered heteroaryl ring having one nitrogen atom. Exemplary $R^3$ groups include but are not limited to optionally substituted pyridinyl, pyrimidinyl, pyrazinyl, pyridazinyl, triazinyl, or tetrazinyl.

In some embodiments, $R^3$ is an optionally substituted 8-10 membered bicyclic heteroaryl ring having 1-5 heteroatoms independently selected from nitrogen, oxygen, or sulfur. In some embodiments, $R^3$ is a substituted 8-10 membered bicyclic heteroaryl ring having 1-5 heteroatoms independently selected from nitrogen, oxygen, or sulfur. In some embodiments, $R^3$ is an unsubstituted 8-10 membered bicyclic heteroaryl ring having 1-5 heteroatoms independently selected from nitrogen, oxygen, or sulfur. In some embodiments, $R^3$ is an optionally substituted 8-membered bicyclic heteroaryl ring having 1-5 heteroatoms independently selected from nitrogen, oxygen, or sulfur. In some embodiments, $R^3$ is a substituted 8-membered bicyclic heteroaryl ring having 1-5 heteroatoms independently selected from nitrogen, oxygen, or sulfur. In some embodiments, $R^3$ is an unsubstituted 8-membered bicyclic heteroaryl ring having 1-5 heteroatoms independently selected from nitrogen, oxygen, or sulfur. In some embodiments, $R^3$ is an optionally substituted 9-membered bicyclic heteroaryl ring having 1-5 heteroatoms independently selected from nitrogen, oxygen, or sulfur. In some embodiments, $R^3$ is a substituted 9-membered bicyclic heteroaryl ring having 1-5 heteroatoms independently selected from nitrogen, oxygen, or sulfur. In some embodiments, $R^3$ is an unsubstituted 9-membered bicyclic heteroaryl ring having 1-5 heteroatoms independently selected from nitrogen, oxygen, or sulfur. In some embodiments, $R^3$ is an optionally substituted 10-membered bicyclic heteroaryl ring having 1-5 heteroatoms independently selected from nitrogen, oxygen, or sulfur. In some embodiments, $R^3$ is a substituted 10-membered bicyclic heteroaryl ring having 1-5 heteroatoms independently selected from nitrogen, oxygen, or sulfur. In some embodiments, $R^3$ is an unsubstituted 10-membered bicyclic heteroaryl ring having 1-5 heteroatoms independently selected from nitrogen, oxygen, or sulfur.

In some embodiments, $R^3$ is an optionally substituted 5,6-fused heteroaryl ring having 1-5 heteroatoms independently selected from nitrogen, oxygen, or sulfur. In some embodiments, $R^3$ is an optionally substituted 5,6-fused heteroaryl ring having 1-4 heteroatoms independently selected from nitrogen, oxygen, or sulfur. In some embodiments, $R^3$ is an optionally substituted 5,6-fused heteroaryl ring having 1-3 heteroatoms independently selected from nitrogen, oxygen, or sulfur. In some embodiments, $R^3$ is an optionally substituted 5,6-fused heteroaryl ring having two heteroatoms independently selected from nitrogen, oxygen, or sulfur. In some embodiments, $R^3$ is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, $R^3$ is an optionally substituted 5,6-fused heteroaryl ring having three heteroatoms independently selected from nitrogen, oxygen, or sulfur. In some embodiments, $R^3$ is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, $R^3$ is an optionally substituted 5,6-fused heteroaryl ring having four heteroatoms independently selected from nitrogen, oxygen, or sulfur. In some embodiments, $R^3$ is an optionally substituted 5,6-fused heteroaryl ring having five heteroatoms independently selected from nitrogen, oxygen, or sulfur.

In some embodiments, $R^3$ is an optionally substituted 5,6-fused heteroaryl ring having 1-5 heteroatoms independently selected from nitrogen, oxygen, or sulfur. In other embodiments, $R^3$ is an optionally substituted 5,6-fused heteroaryl ring having 1-2 heteroatoms independently selected from nitrogen, oxygen, or sulfur. In certain embodiments, $R^3$ is an optionally substituted 5,6-fused heteroaryl ring having one heteroatom independently selected from nitrogen, oxygen, or sulfur. In some embodiments, $R^3$ is optionally substituted indolyl. In some embodiments, $R^3$ is optionally substituted benzofuranyl. In some embodiments, $R^3$ is optionally substituted benzo[b]thienyl. In certain embodiments, $R^3$ is an optionally substituted 5,6-fused heteroaryl ring having two heteroatoms independently selected from nitrogen, oxygen, or sulfur. In some embodiments, $R^3$ is optionally substituted azaindolyl. In some embodiments, $R^3$ is optionally substituted benzimidazolyl. In some embodiments, $R^3$ is optionally substituted benzothiazolyl. In some embodiments, $R^3$ is optionally substituted benzoxazolyl. In some embodiments, $R^3$ is an optionally substituted indazolyl. In certain embodiments, $R^3$ is an optionally substituted 5,6-fused heteroaryl ring having three heteroatoms independently selected from nitrogen, oxygen, or sulfur. In some embodiments, $R^3$ is optionally substituted oxazolopyridiyl, thiazolopyridinyl or imidazopyridinyl. In certain embodiments, $R^3$ is an optionally substituted 5,6-fused heteroaryl ring having four heteroatoms independently selected from nitrogen, oxygen, or sulfur. In some embodiments, $R^3$ is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, $R^3$ is an optionally substituted 5,6-fused heteroaryl ring having five heteroatoms independently selected from nitrogen, oxygen, or sulfur.

In certain embodiments, $R^3$ is an optionally substituted 6,6-fused heteroaryl ring having 1-5 heteroatoms independently selected from nitrogen, oxygen, or sulfur. In some embodiments, $R^3$ is an optionally substituted 6,6-fused heteroaryl ring having 1-2 heteroatoms independently selected from nitrogen, oxygen, or sulfur. In other embodiments, $R^3$ is an optionally substituted 6,6-fused heteroaryl ring having one heteroatom selected from nitrogen, oxygen, or sulfur. In some embodiments, $R^3$ is optionally substituted quinolinyl. In some embodiments, $R^3$ is optionally substituted isoquinolinyl. In some embodiments, $R^3$ is an optionally substituted 6,6-fused heteroaryl ring having two heteroatoms independently selected from nitrogen, oxygen, or sulfur. In some embodiments, $R^3$ is optionally substituted quinazolinyl, phthalazinyl, quinoxalinyl or naphthyridinyl. In some embodiments, $R^3$ is an optionally substituted 6,6-fused heteroaryl ring having three heteroatoms independently selected from nitrogen, oxygen, or sulfur. In some embodiments, $R^3$ is optionally substituted pyridopyrimidinyl, pyridopyridazinyl, pyridopyrazinyl, or benzotriazinyl. In some embodiments, $R^3$ is an optionally substituted 6,6-fused heteroaryl ring having four heteroatoms independently selected from nitrogen, oxygen, or sulfur. In some embodiments, $R^3$ is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, $R^3$ is an optionally substituted 6,6-fused heteroaryl ring having five heteroatoms independently selected from nitrogen, oxygen, or sulfur.

As defined generally above, $R^4$ of formula I is selected from R, halogen, —CN, —NO$_2$, —CF$_3$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^4$ is R. In some embodiments, $R^4$ is hydrogen. In some embodiments, $R^4$ is optionally substituted $C_{1-6}$ aliphatic. In some embodiments, $R^4$ is $C_{1-6}$ alkyl. In some embodiments, $R^4$ is methyl.

In some embodiments, $R^4$ is halogen. In some embodiments, $R^4$ is —F. In some embodiments, $R^4$ is —Cl. In some embodiments, $R^4$ is —Br. In some embodiments, $R^4$ is —I.

In some embodiments, $R^4$ is —CN. In some embodiments, $R^4$ is —NO$_2$. In some embodiments, $R^4$ is —CF$_3$. In some embodiments, $R^4$ is —C(O)OR'. In some embodiments, $R^4$ is —OR'. In some embodiments, $R^4$ is —SR'. In some embodiments, $R^4$ is —C(O)N(R')$_2$. In some embodiments, $R^4$ is —N(R')$_2$. In some embodiments, $R^4$ is —S(O)$_2$N(R)$_2$. In some embodiments, $R^4$ is —N(R')S(O)$_2$CF$_3$. In some embodiments, $R^4$ is —C(O)R'. In some embodiments, $R^4$ is —N(R')C(O)R'. In some embodiments, $R^4$ is —S(O)R'. In some embodiments, $R^4$ is —S(O)$_2$R'. In some embodiments, $R^4$ is —N(R')C(O)OR. In some embodiments, $R^4$ is —N(R')S(O)$_2$R'.

As defined generally above, $R^5$ of formula I is selected from R, halogen, —CN, —NO$_2$, —CF$_3$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^5$ is R. In some embodiments, $R^5$ is hydrogen. In some embodiments, $R^5$ is optionally substituted $C_{1-6}$ aliphatic. In some embodiments, $R^5$ is $C_{1-6}$ alkyl. In some embodiments, $R^5$ is methyl.

In some embodiments, $R^5$ is halogen. In some embodiments, $R^5$ is —F. In some embodiments, $R^5$ is —Cl. In some embodiments, $R^5$ is —Br. In some embodiments, $R^5$ is —I.

In some embodiments, $R^5$ is —CN. In some embodiments, $R^5$ is —NO$_2$. In some embodiments, $R^5$ is —CF$_3$. In some embodiments, $R^5$ is —C(O)OR'. In some embodiments, $R^5$ is —OR'. In some embodiments, $R^5$ is —SR'. In some embodiments, $R^5$ is —C(O)N(R')$_2$. In some embodiments, $R^5$ is —N(R')$_2$. In some embodiments, $R^5$ is —S(O)$_2$N(R)$_2$. In some embodiments, $R^5$ is —N(R')S(O)$_2$CF$_3$. In some embodiments, $R^5$ is —C(O)R'. In some embodiments, $R^5$ is —N(R')C(O)R'. In some embodiments, $R^5$ is —S(O)R'. In some embodiments, $R^5$ is —S(O)$_2$R'. In some embodiments, $R^5$ is —N(R')C(O)OR. In some embodiments, $R^5$ is —N(R')S(O)$_2$R'.

As defined generally above, $R^6$ of formula I is selected from R, halogen, —CN, —NO$_2$, —CF$_3$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'.

In some embodiments, $R^6$ is R. In some embodiments, $R^6$ is hydrogen. In some embodiments, $R^6$ is optionally substituted $C_{1-6}$ aliphatic. In some embodiments, $R^6$ is optionally substituted $C_{1-6}$ alkyl. In some embodiments, $R^6$ is substituted $C_{1-6}$ alkyl. In some embodiments, $R^6$ is unsubstituted $C_{1-6}$ alkyl. In some embodiments, $R^6$ is methyl. In some embodiments, $R^6$ is $C_{1-6}$ alkyl optionally substituted with one or more halogen. In some embodiments, $R^6$ is $C_{1-6}$ haloalkyl. In some embodiments, $R^6$ is optionally substituted $C_{3-6}$ cycloalkyl. In some embodiments, $R^6$ is substituted $C_{3-6}$ cycloalkyl. In some embodiments, $R^6$ is unsubstituted $C_{3-6}$ cycloalkyl. In some embodiments, $R^6$ is optionally substituted cyclopropyl. In some embodiments, $R^6$ is substituted cyclopropyl. In some embodiments, $R^6$ is unsubstituted cyclopropyl. In some embodiments, $R^6$ is optionally substituted cyclobutyl. In some embodiments, $R^6$ is substituted cyclobutyl. In some embodiments, $R^6$ is unsubstituted cyclobutyl. In some embodiments, $R^6$ is optionally substituted cyclopentyl. In some embodiments, $R^6$ is substituted cyclopentyl. In some embodiments, $R^6$ is unsubstituted cyclopentyl. In some embodiments, $R^6$ is optionally substituted cyclohexyl. In some embodiments, $R^6$ is substituted cyclohexyl. In some embodiments, $R^6$ is unsubstituted cyclohexyl.

In some embodiments, $R^6$ is halogen. In some embodiments, $R^6$ is —F. In some embodiments, $R^6$ is —Cl. In some embodiments, $R^6$ is —Br. In some embodiments, $R^6$ is —I.

In some embodiments, $R^6$ is —CN. In some embodiments, $R^6$ is —NO$_2$. In some embodiments, $R^6$ is —CF$_3$. In some embodiments, $R^6$ is —C(O)OR'. In some embodiments, $R^6$ is —OR'. In some embodiments, $R^6$ is —SR'. In some embodiments, $R^6$ is —C(O)N(R')$_2$. In some embodiments, $R^6$ is —N(R')$_2$. In some embodiments, $R^6$ is —S(O)$_2$N(R)$_2$. In some embodiments, $R^6$ is —N(R')S(O)$_2$CF$_3$. In some embodiments, $R^6$ is —C(O)R'. In some embodiments, $R^6$ is —N(R')C(O)R'. In some embodiments, $R^6$ is —S(O)R'.

In some embodiments, $R^6$ is —S(O)$_2$R'. In some embodiments, $R^6$ is —N(R')C(O)OR. In some embodiments, $R^6$ is —N(R')S(O)$_2$R'.

In some embodiments, optionally $R^2$ and -A-L$^1$-, $R^2$ and -L$^2$-R$^3$, $R^4$ and $R^5$, $R^5$ and $R^6$ and/or $R^6$ and -A-L$^1$- of formula I are taken together with their intervening atoms to form an optionally substituted ring selected from a 4-8 membered saturated or partially unsaturated carbocyclic ring, phenyl, a 4-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, optionally one of $R^2$ and -A-L$^1$-, $R^2$ and -L$^2$-R$^3$, $R^4$ and $R^5$, $R^5$ and $R^6$, or $R^6$ and -A-L$^1$- is taken together with their intervening atoms to form an optionally substituted ring selected from a 4-8 membered saturated or partially unsaturated carbocyclic ring, phenyl, a 4-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, optionally one of $R^2$ and -A-L$^1$-, $R^2$ and -L$^2$-R$^3$, $R^4$ and $R^5$, $R^5$ and $R^6$, or $R^6$ and -A-L$^1$- is taken together with their intervening atoms to form an optionally substituted 4-8 membered saturated or partially unsaturated carbocyclic ring. In some embodiments, optionally one of $R^2$ and -A-L$^1$-, $R^2$ and -L$^2$-R$^3$, $R^4$ and $R^5$, $R^5$ and $R^6$, or $R^6$ and -A-L$^1$- is taken together with their intervening atoms to form an optionally substituted phenyl. In some embodiments, optionally one of $R^2$ and -A-L$^1$-, $R^2$ and -L$^2$-R$^3$, $R^4$ and $R^5$, $R^5$ and $R^6$, or $R^6$ and -A-L$^1$- is taken together with their intervening atoms to form an optionally substituted 4-8 membered saturated or partially unsaturated heterocyclic ring having 1-4 heteroatoms independently selected from nitrogen, oxygen. In some embodiments, optionally one of $R^2$ and -A-L$^1$-, $R^2$ and -L$^2$-R$^3$, $R^4$ and $R^5$, $R^5$ and $R^6$, or $R^6$ and -A-L$^1$- is taken together with their intervening atoms to form an optionally substituted 5-6 membered heteroaryl ring having 1-4 heteroatoms independently selected from nitrogen, oxygen, or sulfur.

In some embodiments, $R^2$ and -A-L$^1$- are taken together with their intervening atoms to form an optionally substituted ring selected from 5-8 membered saturated or partially unsaturated carbocyclic ring, phenyl, a 5-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^2$ and -L$^2$-R$^3$ are taken together with their intervening atoms to form an optionally substituted ring selected from 5-8 membered saturated or partially unsaturated carbocyclic ring, phenyl, a 5-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^4$ and $R^5$ are taken together with their intervening atoms to form an optionally substituted ring selected from 5-8 membered saturated or partially unsaturated carbocyclic ring, phenyl, a 5-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^5$ and $R^6$ are taken together with their intervening atoms to form an optionally substituted ring selected from 5-8 membered saturated or partially unsaturated carbocyclic ring, phenyl, a 5-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^6$ and -A-L- are taken together with their intervening atoms to form an optionally substituted ring selected from 5-8 membered saturated or partially unsaturated carbocyclic ring, phenyl, a 5-8 membered saturated or partially unsaturated heterocyclic ring having 1-4 heteroatoms independently selected from nitrogen, oxygen, or sulfur, or a 5-6 membered heteroaryl ring having 1-4 heteroatoms independently selected from nitrogen, oxygen, or sulfur.

In some embodiments, $R^2$ is —C(O)N(R)-$L^3$-$R^z$ or —C(O)N(R)—C(R)$_2$-$L^3$-$R^z$, wherein one R group and $R^3$ are optionally taken together with their intervening atoms to form an optionally substituted 6-8 membered saturated or partially unsaturated heterocyclic ring having 1-4 heteroatoms independently selected from nitrogen, oxygen, or sulfur, or an optionally substituted 6 membered heteroaryl ring having 1-4 heteroatoms independently selected from nitrogen, oxygen, or sulfur.

In some embodiments, the present invention provides compounds of the general formula Ia, Ib, Ic or Id:

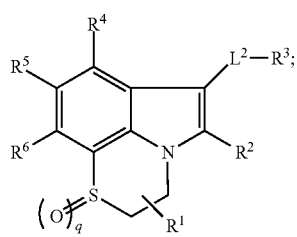

Ia

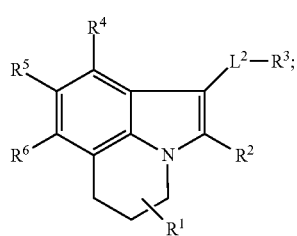

Ib

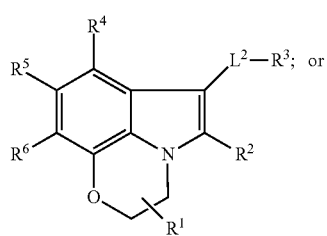

Ic

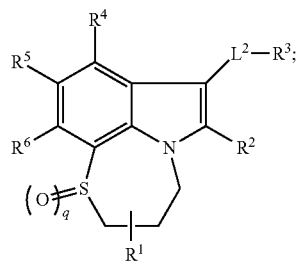

Id or a pharmaceutically acceptable salt thereof, wherein each of $R^1$, $R^2$, $R^3$, $R^4$, $R^5$, $R^6$, A, $L^1$ and $L^2$ is as defined and described in embodiments herein and q is 0, 1 or 2.

In some embodiments, the present invention provides compounds of the general formula Ia:

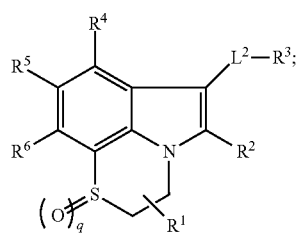

Ia or a pharmaceutically acceptable salt thereof, wherein each of $R^1$, $R^2$, $R^3$, $R^4$, $R^5$, $R^6$, A, $L^1$ and $L^2$ is as defined and described in embodiments herein and q is 0, 1 or 2.

In some embodiments, the present invention provides compounds of the general formula Ia, where q is 0. In some embodiments, q is 1. In some embodiments, q is 2.

In some embodiments, $R^1$ is hydrogen. In some embodiments, $R^1$ is not hydrogen.

In some embodiments, $R^2$ is selected from —C(O)O-$L^3$-$R^z$ or —C(O)N(R)$L^3$-$R^z$. In some embodiments, $L^3$ is a covalent bond or —SO$_2$—. In some embodiments, $R^z$ is hydrogen, optionally substituted $C_{1-4}$ alkyl or optionally substituted aryl. In some embodiments, $R^z$ is optionally substituted phenyl, optionally substituted naphthyl, or optionally substituted tetrahydronaphthyl. In some embodiments, R is hydrogen, optionally substituted $C_{1-4}$ alkyl. In some embodiments, $R^2$ is —CO$_2$H, —C(O)NHSO$_2$CH$_3$ or —C(O)NHSO$_2$C$_6$H$_5$.

In some embodiments, $L^2$ is an optionally substituted bivalent straight or branched $C_{3-4}$ hydrocarbon chain wherein one methylene unit of $L^2$ is optionally replaced with —O—. In some embodiments, $L^2$ is —CH$_2$CH$_2$O— or —CH$_2$CH$_2$CH$_2$O—.

In some embodiments, $R^3$ is optionally substituted phenyl or an optionally substituted 6-10 membered bicyclic saturated, partially unsaturated or aryl ring. In some embodiments, $R^3$ is optionally substituted phenyl, optionally substituted naphthyl, or optionally substituted tetrahydronaphthyl. In some embodiments, $R^3$ is

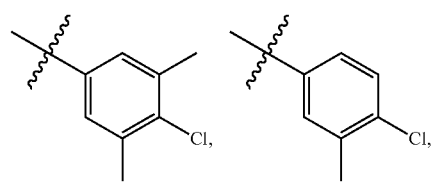

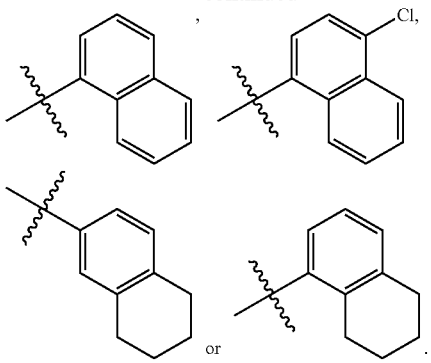

In some embodiments, $R^4$ is hydrogen. In some embodiments, $R^4$ is halogen. In some embodiments, $R^4$ is —Cl. In some embodiments, $R^4$ is —CF$_3$. In some embodiments, $R^5$ is hydrogen. In some embodiments, $R^5$ is halogen. In some embodiments, $R^5$ is —Cl. In some embodiments, $R^5$ is —CF$_3$. In some embodiments, $R^6$ is hydrogen. In some embodiments, $R^6$ is halogen. In some embodiments, $R^6$ is —Cl. In some embodiments, $R^6$ is —CF$_3$.

In some embodiments, the present invention provides compounds of the general formula Ib:

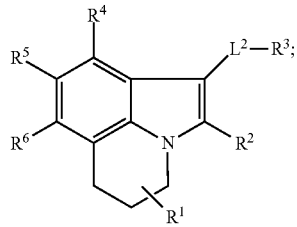

Ib or a pharmaceutically acceptable salt thereof, wherein each of $R^1$, $R^2$, $R^3$, $R^4$, $R^5$, $R^6$, A, $L^1$ and $L^2$ is as defined and described in embodiments herein.

In some embodiments, the present invention provides compounds of the general formula Ib where $R^1$ is hydrogen. In some embodiments, $R^1$ is not hydrogen.

In some embodiments, $R^2$ is selected from —C(O)O-L$^3$-R$^z$ or —C(O)N(R)L$^3$-R$^z$. In some embodiments, $L^3$ is a covalent bond or —SO$_2$—. In some embodiments, $R^z$ is hydrogen, optionally substituted C$_{1-4}$ alkyl or optionally substituted aryl. In some embodiments, $R^z$ is optionally substituted phenyl, optionally substituted naphthyl, or optionally substituted tetrahydronaphthyl. In some embodiments, R is hydrogen, optionally substituted C$_{1-4}$ alkyl. In some embodiments, $R^2$ is —CO$_2$H, —C(O)NHSO$_2$CH$_3$ or —C(O)NHSO$_2$C$_6$H$_5$.

In some embodiments, $L^2$ is an optionally substituted bivalent straight or branched C$_{3-4}$ hydrocarbon chain wherein one methylene unit of $L^2$ is optionally replaced with —O—. In some embodiments, $L^2$ is —CH$_2$CH$_2$O— or —CH$_2$CH$_2$CH$_2$O—.

In some embodiments, $R^3$ is optionally substituted phenyl or an optionally substituted 6-10 membered bicyclic saturated, partially unsaturated or aryl ring. In some embodiments, $R^3$ is optionally substituted phenyl, optionally substituted naphthyl, or optionally substituted tetrahydronaphthyl. In some embodiments, $R^3$ is

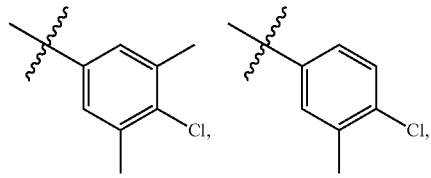

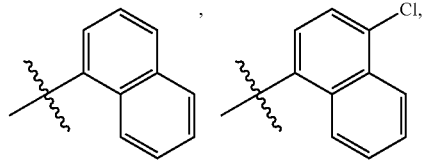

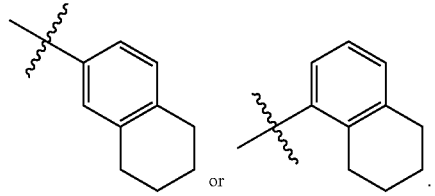

In some embodiments, $R^4$ is hydrogen. In some embodiments, $R^4$ is halogen. In some embodiments, $R^4$ is —Cl. In some embodiments, $R^4$ is —CF$_3$. In some embodiments, $R^5$ is hydrogen. In some embodiments, $R^5$ is halogen. In some embodiments, $R^5$ is —Cl. In some embodiments, $R^5$ is —CF$_3$. In some embodiments, $R^6$ is hydrogen. In some embodiments, $R^6$ is halogen. In some embodiments, $R^6$ is —Cl. In some embodiments, $R^6$ is —CF$_3$.

In some embodiments, the present invention provides compounds of the general formula Ic:

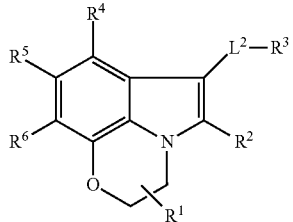

Ic or a pharmaceutically acceptable salt thereof, wherein each of $R^1$, $R^2$, $R^3$, $R^4$, $R^5$, $R^6$, A, $L^1$ and $L^2$ is as defined and described in embodiments herein. In some embodiments, the present invention provides compounds of the general formula Ic where $R^1$ is hydrogen.

In some embodiments, the present invention provides compounds of the general formula Ic where $R^1$ is hydrogen. In some embodiments, $R^1$ is not hydrogen.

In some embodiments, $R^2$ is selected from —C(O)O-L$^3$-R$^z$ or —C(O)N(R)-L$^3$-R$^z$. In some embodiments, $L^3$ is a covalent bond or —SO$_2$—. In some embodiments, $R^z$ is hydrogen, optionally substituted C$_{1-4}$ alkyl or optionally substituted aryl. In some embodiments, $R^z$ is optionally substituted phenyl, optionally substituted naphthyl, or optionally substituted tetrahydronaphthyl. In some embodiments, R is hydrogen, optionally substituted C$_{1-4}$ alkyl. In some embodiments, $R^2$ is —CO$_2$H, —C(O)NHSO$_2$CH$_3$ or —C(O)NHSO$_2$C$_6$H$_5$.

In some embodiments, L² is an optionally substituted bivalent straight or branched C₃-4 hydrocarbon chain wherein one methylene unit of L² is optionally replaced with —O—. In some embodiments, L² is —CH₂CH₂O— or —CH₂CH₂CH₂O—.

In some embodiments, R³ is optionally substituted phenyl or an optionally substituted 6-10 membered bicyclic saturated, partially unsaturated or aryl ring. In some embodiments, R³ is optionally substituted phenyl, optionally substituted naphthyl, or optionally substituted tetrahydronaphthyl. In some embodiments, R³ is

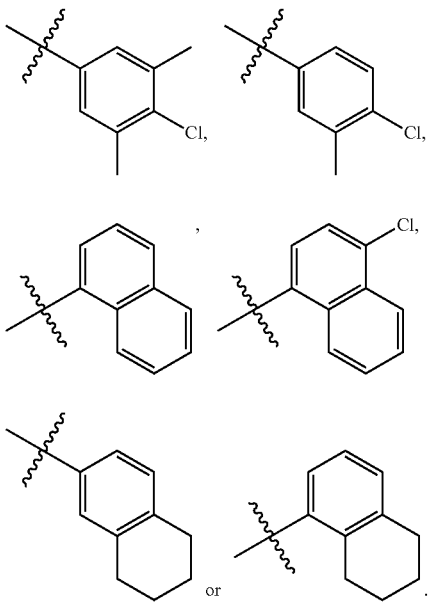

In some embodiments, R⁴ is hydrogen. In some embodiments, R⁴ is halogen. In some embodiments, R⁴ is —Cl. In some embodiments, R⁴ is —CF₃. In some embodiments, R⁵ is hydrogen. In some embodiments, R⁵ is halogen. In some embodiments, R⁵ is —Cl. In some embodiments, R⁵ is —CF₃. In some embodiments, R⁶ is hydrogen. In some embodiments, R⁶ is halogen. In some embodiments, R⁶ is —Cl. In some embodiments, R⁶ is —CF₃.

In some embodiments, the present invention provides compounds of the general formula Id:

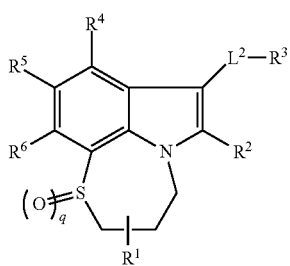

Id or a pharmaceutically acceptable salt thereof, wherein each of R¹, R², R³, R⁴, R⁵, R⁶, A, L¹ and L² is as defined and described in embodiments herein and q is 0, 1 or 2.

In some embodiments, the present invention provides compounds of the general formula Id, where q is 0. In some embodiments, q is 1. In some embodiments, q is 2.

In some embodiments, R¹ is hydrogen. In some embodiments, R¹ is not hydrogen.

In some embodiments, R² is selected from —C(O)O-L³-R^z or —C(O)N(R)L³-R^z. In some embodiments, L³ is a covalent bond or —SO₂—. In some embodiments, R^z is hydrogen, optionally substituted C₁₋₄ alkyl or optionally substituted aryl. In some embodiments, R^z is optionally substituted phenyl, optionally substituted naphthyl, or optionally substituted tetrahydronaphthyl. In some embodiments, R is hydrogen, optionally substituted C₁₋₄ alkyl. In some embodiments, R² is —CO₂H, —C(O)NHSO₂CH₃ or —C(O)NHSO₂C₆H₅.

In some embodiments, L² is an optionally substituted bivalent straight or branched C₃₋₄ hydrocarbon chain wherein one methylene unit of L² is optionally replaced with —O—. In some embodiments, L² is —CH₂CH₂O— or —CH₂CH₂CH₂O—.

In some embodiments, R³ is optionally substituted phenyl or an optionally substituted 6-10 membered bicyclic saturated, partially unsaturated or aryl ring. In some embodiments, R³ is optionally substituted phenyl, optionally substituted naphthyl, or optionally substituted tetrahydronaphthyl. In some embodiments, R³ is

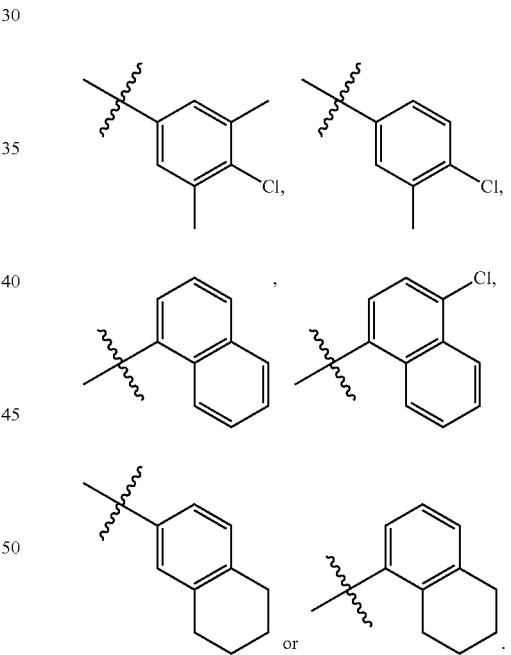

In some embodiments, R⁴ is hydrogen. In some embodiments, R⁴ is halogen. In some embodiments, R⁴ is —Cl. In some embodiments, R⁴ is —CF₃. In some embodiments, R⁵ is hydrogen. In some embodiments, R⁵ is halogen. In some embodiments, R⁵ is —Cl. In some embodiments, R⁵ is —CF₃. In some embodiments, R⁶ is hydrogen. In some embodiments, R⁶ is halogen. In some embodiments, R⁶ is —Cl. In some embodiments, R⁶ is —CF₃.

Exemplary compounds of general formula I are set forth in Table 1, below:

TABLE 1

| Example | Structure | Name |
|---|---|---|
| I-1 | 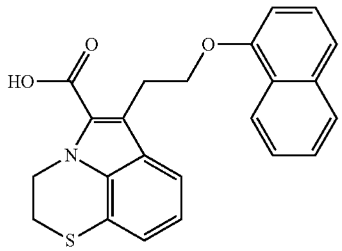 [SMILES: O=C(O)c1c(CCOc2cccc3ccccc23)c2cccc3c2n1CCS3] | 6-(2-(naphthalen-1-yloxy)ethyl)-2,3-dihydro-[1,4]thiazino[2,3,4-hi]indole-5-carboxylic acid |
| I-2 | 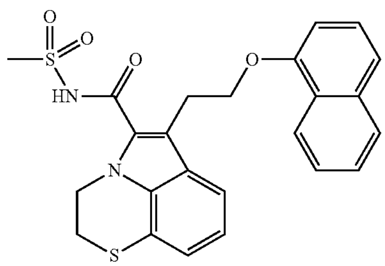 [SMILES: CS(=O)(=O)NC(=O)c1c(CCOc2cccc3ccccc23)c2cccc3c2n1CCS3] | N-(methylsulfonyl)-6-(2-(naphthalen-1-yloxy)ethyl)-2,3-dihydro-[1,4]thiazino[2,3,4-hi]indole-5-carboxamide |
| I-3 | 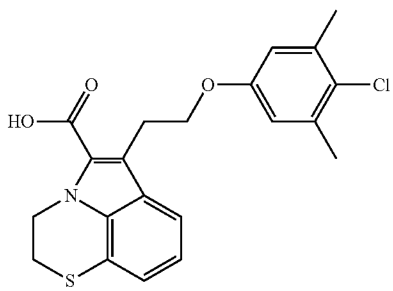 [SMILES: Cc1cc(OCCc2c(C(=O)O)n3c4c(cccc24)SCC3)cc(C)c1Cl] | 6-(2-(4-chloro-3,5-dimethylphenoxy)ethyl)-2,3-dihydro-[1,4]thiazino[2,3,4-hi]indole-5-carboxylic acid |
| I-4 | 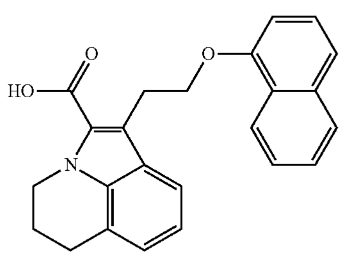 [SMILES: O=C(O)c1c(CCOc2cccc3ccccc23)c2cccc3c2n1CCC3] | 1-(2-(naphthalen-1-yloxy)ethyl)-5,6-dihydro-4H-pyrrolo[3,2,1-ij]quinoline-2-carboxylic acid |
| I-5 | 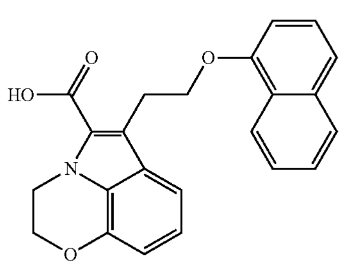 | 6-(2-(naphthalen-1-yloxy)ethyl)-2,3-dihydro-[1,4]oxazino[2,3,4-hi]indole-5-carboxylic acid |
| I-6 | 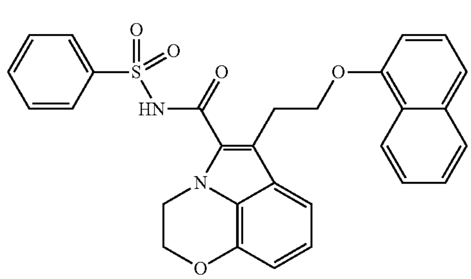 [SMILES: O=C(NS(=O)(=O)c1ccccc1)c1c(CCOc2cccc3ccccc23)c2cccc3c2n1CCO3] | 6-(2-(naphthalen-1-yloxy)ethyl)-N-(phenylsulfonyl)-2,3-dihydro-[1,4]oxazino[2,3,4-hi]indole-5-carboxamide |

TABLE 1-continued

| Example | Structure | Name |
|---|---|---|
| I-7 | 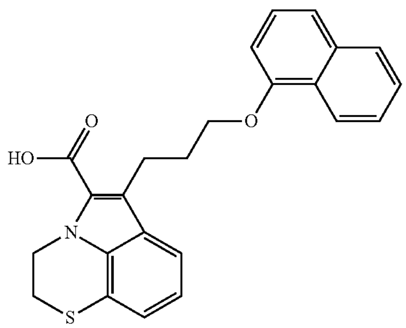 [SMILES: O=C(O)c1c(CCCOc2cccc3ccccc23)c2cccc3c2n1CCS3] | 6-(3-(naphthalen-1-yloxy)propyl)-2,3-dihydro-[1,4]thiazino[2,3,4-hi]indole-5-carboxylic acid |
| I-8 | 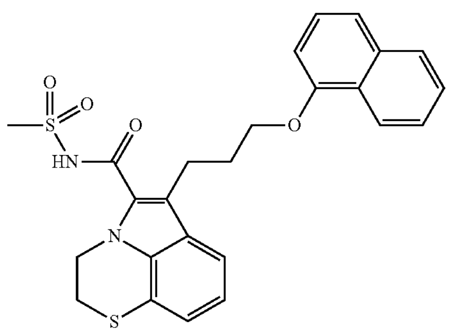 [SMILES: CS(=O)(=O)NC(=O)c1c(CCCOc2cccc3ccccc23)c2cccc3c2n1CCS3] | N-(methylsulfonyl)-6-(3-(naphthalen-1-yloxy)propyl)-2,3-dihydro-[1,4]thiazino[2,3,4-hi]indole-5-carboxamide |
| I-9 | 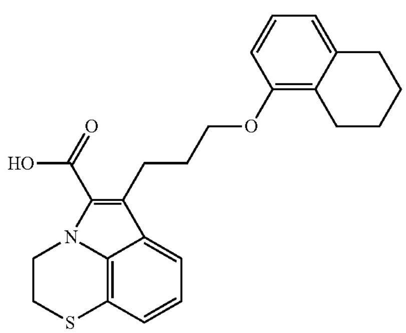 [SMILES: O=C(O)c1c(CCCOc2cccc3c2CCCC3)c2cccc3c2n1CCS3] | 6-(3-((5,6,7,8-tetrahydronaphthalen-1-yl)oxy)propyl)-2,3-dihydro-[1,4]oxazino[2,3,4-hi]indole-5-carboxylic acid |
| I-10 | 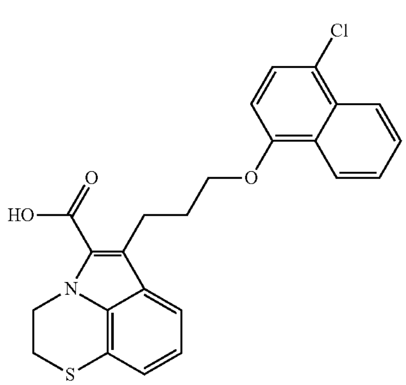 [SMILES: O=C(O)c1c(CCCOc2ccc(Cl)c3ccccc23)c2cccc3c2n1CCS3] | 6-(3-((4-chloronaphthalen-1-yl)oxy)propyl)-2,3-dihydro-[1,4]thiazino[2,3,4-hi]indole-5-carboxylic acid |

TABLE 1-continued
| Example | Structure | Name |
|---|---|---|
| I-11 | 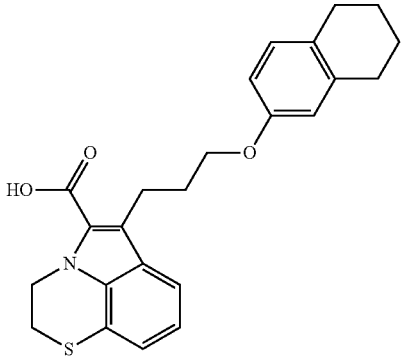 [SMILES: O=C(O)c1c(CCCOc2ccc3c(c2)CCCC3)c2cccc3c2n1CCS3] | 6-(3-((5,6,7,8-tetrahydronaphthalen-2-yl)oxy)propyl)-2,3-dihydro-[1,4]thiazino[2,3,4-hi]indole-5-carboxylic acid |
| I-12 | 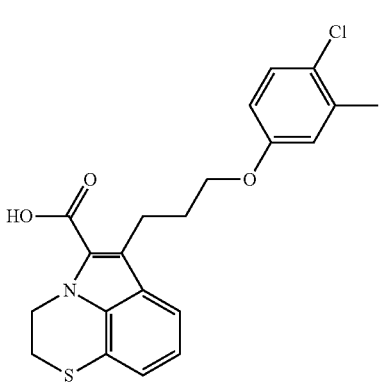 [SMILES: Cc1cc(OCCCc2c(C(=O)O)n3c4c(cccc24)SCC3)ccc1Cl] | 6-(3-(4-chloro-3-methylphenoxy)propyl)-2,3-dihydro-[1,4]thiazino[2,3,4-hi]indole-5-carboxylic acid |
| I-13 | 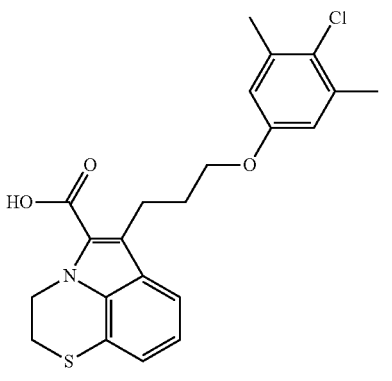 [SMILES: Cc1cc(OCCCc2c(C(=O)O)n3c4c(cccc24)SCC3)cc(C)c1Cl] | 6-(3-(4-chloro-3,5-dimethylphenoxy)propyl)-2,3-dihydro-[1,4]thiazino[2,3,4-hi]indole-5-carboxylic acid |
| I-14 | 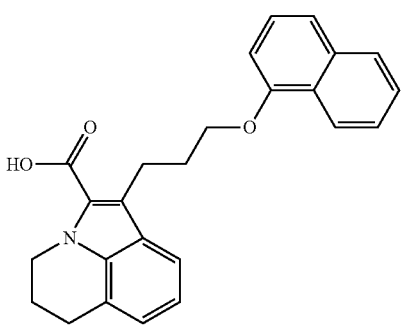 [SMILES: O=C(O)c1c(CCCOc2cccc3ccccc23)c2cccc3c2n1CCC3] | 1-(3-(naphthalen-1-yloxy)propyl)-5,6-dihydro-4H-pyrrolo[3,2,1-ij]quinoline-2-carboxylic acid |

TABLE 1-continued

| Example | Structure | Name |
|---|---|---|
| I-15 | 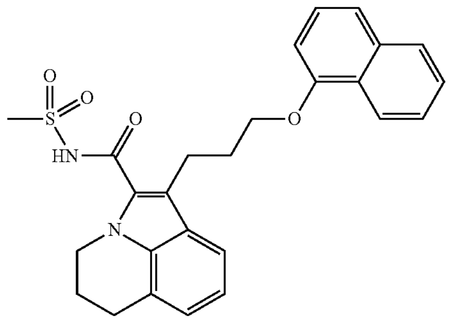 [SMILES: CS(=O)(=O)NC(=O)c1c(CCCOc2cccc3ccccc23)c2cccc3c2n1CCC3] | N-(methylsulfonyl)-1-(3-(naphthalen-1-yloxy)propyl)-5,6-dihydro-4H-pyrrolo[3,2,1-ij]quinoline-2-carboxamide |
| I-16 | 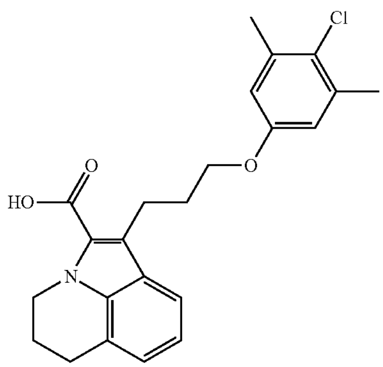 [SMILES: Cc1cc(OCCCc2c(C(=O)O)n3c4c(cccc24)CCC3)cc(C)c1Cl] | 1-(3-(4-chloro-3,5-dimethylphenoxy)propyl)-5,6-dihydro-4H-pyrrolo[3,2,1-ij]quinoline-2-carboxylic acid |
| I-17 | 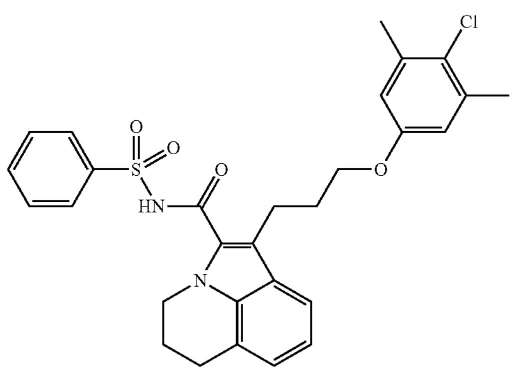 [SMILES: Cc1cc(OCCCc2c(C(=O)NS(=O)(=O)c3ccccc3)n3c4c(cccc24)CCC3)cc(C)c1Cl] | 1-(3-(4-chloro-3,5-dimethylphenoxy)propyl)-N-(phenylsulfonyl)-5,6-dihydro-4H-pyrrolo[3,2,1-ij]quinoline-2-carboxamide |
| I-18 | 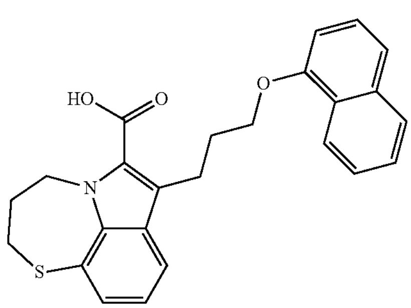 [SMILES: O=C(O)c1c(CCCOc2cccc3ccccc23)c2cccc3c2n1CCCS3] | 7-(3-(naphthalen-1-yloxy)propyl)-3,4-dihydro-2H-[1,4]thiazepino[2,3,4-hi]indole-6-carboxylic acid |

TABLE 1-continued

| Example | Structure | Name |
|---|---|---|
| I-19 | 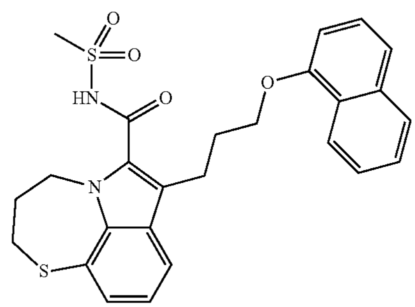 [SMILES: CS(=O)(=O)NC(=O)c1c(CCCOc2cccc3ccccc23)c2cccc3c2n1CCCS3] | N-(methylsulfonyl)-7-(3-(naphthalen-1-yloxy)propyl)-3,4-dihydro-2H-[1,4]thiazepino[2,3,4-hi]indole-6-carboxamide |
| I-20 | 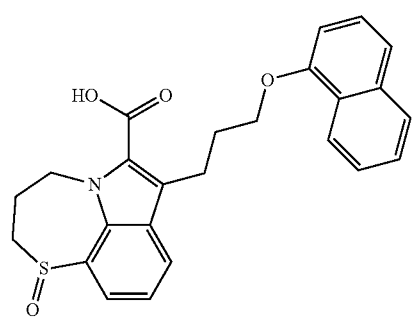 [SMILES: O=C(O)c1c(CCCOc2cccc3ccccc23)c2cccc3c2n1CCCS3=O] | 7-(3-(naphthalen-1-yloxy)propyl)-3,4-dihydro-2H-[1,4]thiazepino[2,3,4-hi]indole-6-carboxylic acid 1-oxide |
| I-21 | 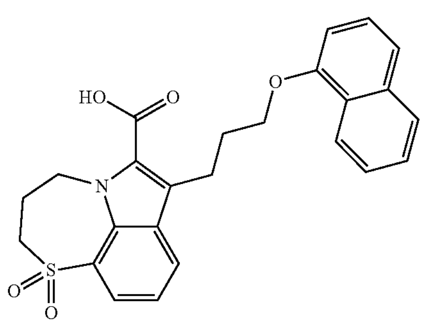 [SMILES: O=C(O)c1c(CCCOc2cccc3ccccc23)c2cccc3c2n1CCCS3(=O)=O] | 7-(3-(naphthalen-1-yloxy)propyl)-3,4-dihydro-2H-[1,4]thiazepino[2,3,4-hi]indole-6-carboxylic acid 1,1-dioxide |
| I-22 | 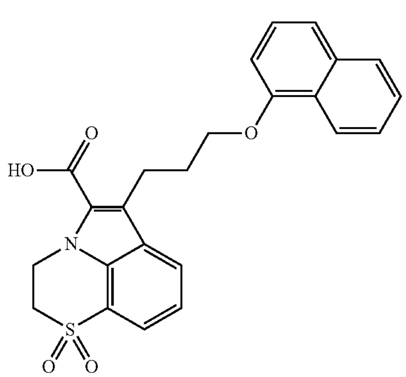 [SMILES: O=C(O)c1c(CCCOc2cccc3ccccc23)c2cccc3c2n1CCS3(=O)=O] | 6-(3-(naphthalen-1-yloxy)propyl)-2,3-dihydro-[1,4]thiazino[2,3,4-hi]indole-5-carboxylic acid 1,1-dioxide |

TABLE 1-continued

| Example | Structure | Name |
| --- | --- | --- |
| I-23 | 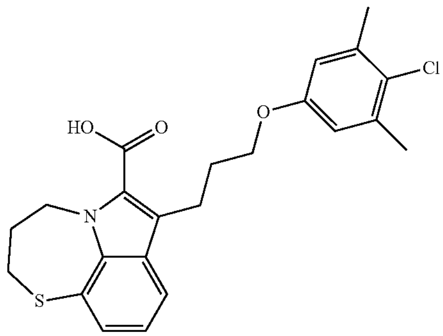 [SMILES: Cc1cc(OCCCc2c(C(=O)O)n3c4c(cccc24)SCCC3)cc(C)c1Cl] | 7-(3-(4-chloro-3,5-dimethylphenoxy)propyl)-3,4-dihydro-2H-[1,4]thiazepino[2,3,4-hi]indole-6-carboxylic acid |
| I-24 | 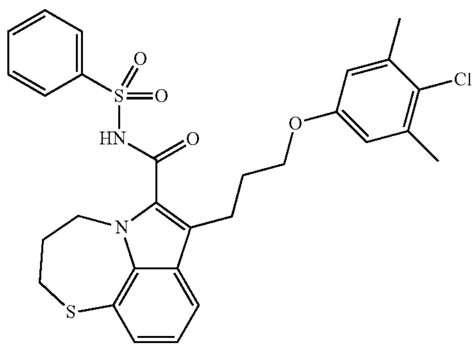 [SMILES: Cc1cc(OCCCc2c(C(=O)NS(=O)(=O)c3ccccc3)n3c4c(cccc24)SCCC3)cc(C)c1Cl] | 7-(3-(4-chloro-3,5-dimethylphenoxy)propyl)-N-(phenylsulfonyl)-3,4-dihydro-2H-[1,4]thiazepino[2,3,4-hi]indole-6-carboxamide |
| I-25 | 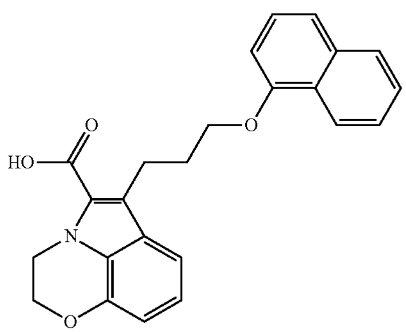 | 6-(3-(naphthalen-1-yloxy)propyl)-2,3-dihydro-[1,4]oxazino[2,3,4-hi]indole-5-carboxylic acid |
| I-26 | 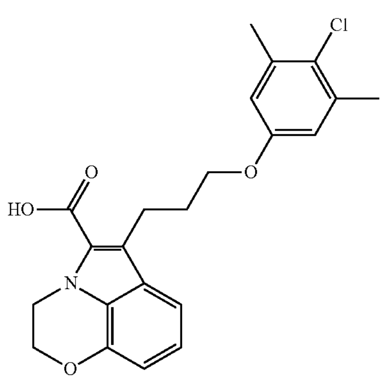 | 6-(3-(4-chloro-3,5-dimethylphenoxy)propyl)-2,3-dihydro-[1,4]oxazino[2,3,4-hi]indole-5-carboxylic acid |

TABLE 1-continued

| Example | Structure | Name |
|---|---|---|
| I-27 | 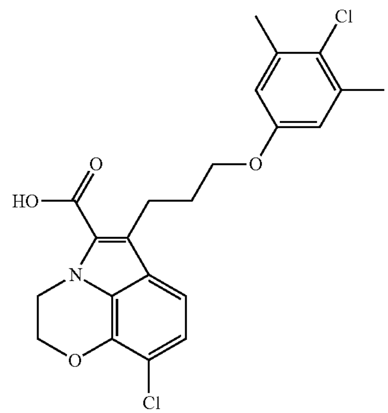 [SMILES: Cc1cc(OCCCc2c(C(=O)O)n3c4c(c(Cl)ccc24)OCC3)cc(C)c1Cl] | 9-chloro-6-(3-(4-chloro-3,5-dimethylphenoxy)propyl)-2,3-dihydro-[1,4]oxazino[2,3,4-hi]indole-5-carboxylic acid |
| I-28 | 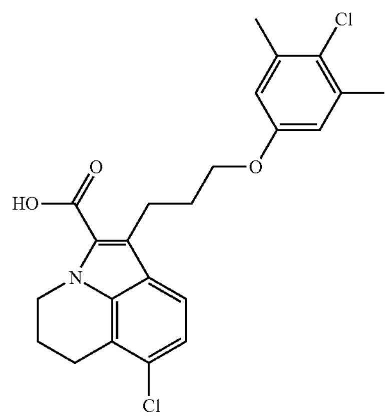 [SMILES: Cc1cc(OCCCc2c(C(=O)O)n3c4c(c(Cl)ccc24)CCC3)cc(C)c1Cl] | 7-chloro-1-(3-(4-chloro-3,5-dimethylphenoxy)propyl)-5,6-dihydro-4H-pyrrolo[3,2,1-ij]quinoline-2-carboxylic acid |

In certain embodiments, the present invention provides any compound selected from those depicted in Table 1, above, or a pharmaceutically acceptable salt thereof.

In some embodiments, a provided compound has a Ki value less than about 0.01 µM for inhibition of Mcl-1. In some embodiments, a provided compound has a Ki value less than about 0.1 µM for inhibition of Mcl-1. In some embodiments, a provided compound has a Ki value less than about 0.2 µM for inhibition of Mcl-1. In some embodiments, a provided compound has a Ki value less than about 0.3 µM for inhibition of Mcl-1. In some embodiments, a provided compound has a Ki value less than about 0.4 µM for inhibition of Mcl-1. In some embodiments, a provided compound has a Ki value less than about 0.5 µM for inhibition of Mcl-1. In some embodiments, a provided compound has a Ki value less than about 0.6 µM for inhibition of Mcl-1. In some embodiments, a provided compound has a Ki value less than about 0.7 µM for inhibition of Mcl-1. In some embodiments, a provided compound has a Ki value less than about 0.8 µM for inhibition of Mcl-1. In some embodiments, a provided compound has a Ki value less than about 0.9 µM for inhibition of Mcl-1. In some embodiments, a provided compound has a Ki value less than about 1 µM for inhibition of Mcl-1. In some embodiments, a provided compound has a Ki value less than about 2 µM for inhibition of Mcl-1. In some embodiments, a provided compound has a Ki value less than about 3 µM for inhibition of Mcl-1. In some embodiments, a provided compound has a Ki value less than about 4 µM for inhibition of Mcl-1. In some embodiments, a provided compound has a Ki value less than about 5 µM for inhibition of Mcl-1. Exemplary assays for measuring Ki value for inhibition of Mcl-1 is widely known in the art, including but not limited to those described in the examples herein. In some embodiments, an assay for measuring Ki value for inhibition of Mcl-1 is described in Example 29.

4. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. The amount of compound in compositions of this invention is such that is effective to measurably inhibit Mcl-1, in a biological sample or in a patient. In certain embodiments, the amount of compound in compositions of this invention is such that is effective to measurably inhibit Mcl-1, in a biological sample or in a patient. In certain embodiments, a composition of this invention is formulated for administration to a patient in need of such composition. In some embodiments, a composition of this invention is formulated for oral administration to a patient.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Mcl-1, or a mutant thereof, activity in a biological sample is useful for a variety of purposes that are known to one of skill in the art. Examples of such purposes include, but are not limited to, blood transfusion, organ transplantation, biological specimen storage, and biological assays.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration.

Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In another aspect the present disclosure provides a method of treating a disease or disorder associated with the expression or over-expression of anti-apoptotic Bcl-2 family protein members, and in certain embodiments those diseases characterized by the expression or the over-expression of Mcl-1 proteins, comprising administering to a mammalian patient a therapeutically effective amount of a compound of formula I, or a pharmaceutically acceptable salt or solvate or a pharmaceutically acceptable carrier thereof.

Further, in accordance with the present invention, a method is provided for preventing, modulating, or treating the progression or onset of diseases or disorders associated with the upregulated activity of the Bcl-2 family of proteins, specifically Mcl-1 protein, such as defined above and hereinafter, wherein a therapeutically effective amount of a compound of formula I is administered to a mammalian, i.e., human, patient in need of treatment.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting Mcl-1, or a mutant thereof, activity in a patient comprising the step of administering to said patient a compound of the present invention, or a composition comprising said compound. In other embodiments, the present invention provides a method for treating a disorder mediated by Mcl-1, or a mutant thereof, in a patient in need thereof, comprising the step of administering to said patient a compound according to the present invention or pharmaceutically acceptable composition thereof. Such disorders are described in detail herein.

Compounds of the present invention modulate the activity of the Bcl-2 family of proteins. Preferably, compounds of the present invention inhibit the activity of one type or a subset of anti-apoptotic Bcl-2 family of proteins, for examples of Mcl-1, Bcl-2, Bcl-xL, and Bcl-w proteins. Consequently, the compounds of the present invention may be used in the treatment of multiple diseases or conditions of abnormal cell growth and/or dysregulated apoptosis, such as cancer, autoimmune disease and pro-thrombotic conditions. Examples of diseases or disorders associated with down-regulated apoptosis can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

The compounds of the present invention possess activity as inhibitors of the Bcl-2 family proteins, particularly Mcl-1 protein, and, therefore, may be used in the treatment of diseases associated with anti-apoptotic Bcl-2 family of proteins. Via the inhibitition of the activity of anti-apoptotic Bcl-2 family proteins, the compounds of the present invention may preferably be employed to release pro-apoptotic and promote apoptosis.

Accordingly, the compounds of the present invention can be administered to mammals, preferably humans, for the treatment of a variety of conditions and disorders, including, but not limited to, treating, preventing, or slowing the progression of various hematologic and solid tumor types and related conditions, resistance development associated with chemotherapy. Consequently, it is believed that the compounds of the present invention may be used in preventing, inhibiting, or treating acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myeogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that the compounds of the present invention may be used in preventing, inhibiting, or treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like. (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Bf. 1. Haematol. 2000 September; 110(3): 584-90; Blood 2000 Feb. 15; 95(4): 1283-92; and New England Journal of Medicine 2004 September; 351(14): 1409-1418).

Involvement of Mcl-1 in acute lymphoblastic leukemia is reported in Blood (1998) 91, 991-1000.

Involvement of Mcl-1 in pancreatic carcinoma is reported in *Cancer Chemotherapeutic Pharmacology* (2008) 62, 1055-1064.

Involvement of Mcl-1 in breast cancer is reported in *Anticancer Research* (2004) 24, 473-482.

Involvement of Mcl-1 in breast and non small-cell lung cancer is also reported in *Nature* (2010) 463, 899-905

Involvement of Mcl-1 in non small-cell lung cancer is also reported in *Oncogene* (2011) 30, 1963-1968

Involvement of Mcl-1 in acute myelogenous leukemia is reported in *Blood* (1998) 91, 991-1000.

Involvement of Mcl-1 in cervical cancer is reported in *Cancer Letters (Shannon, Ireland)* (2002) 180, 63-68.

Involvement of Mcl-1 in cervical cancer is also reported in *Medical Oncology* (2011) 3, 673-677.

Involvement of Mcl-1 in chronic lymphocytic leukemia is reported in *Journal of the National Cancer Institute* (2004) 96, 673-682 and *Immunology* (2005) 114, 441-449.

Involvement of Mcl-1 in colorectal cancer, is reported in *Annals of oncology: Official Journal of the European Society for Medical Oncology/ESMO* (2001) 12, 779-785.

Involvement of Mcl-1 in gastric carcinoma, is reported in *Gastric Cancer* (2004) 7, 78-84.

Involvement of Mcl-1 in gestational trophobalstic disease is reported in *Cancer* (2005) 103, 268-276.

Involvement of Mcl-1 in glioblastoma is reported in *Journal of Neurology, Neurosurgery, and Psychiatry* (1999) 67, 763-768.

Involvement of Mcl-1 in head and neck cancer is reported in *Archives of Otolaryngology-Head and Neck Surgery* (1999) 125, 417-422.

Involvement of Mcl-1 in lung cancer is reported in *Pathology Oncology Research: POR* (1999) 5, 179-186.

Involvement of Mcl-1 in lung cancer is also reported in *Cancer Biology and Therapy* (2005) 4, 267-276.

Involvement of Mcl-1 in mesothioloma, is reported in *Clinical Cancer Research* (1999) 5, 3508-3515.

Involvement of Mcl-1 in mesothioloma, is also reported in *Carcinogenesis* (2010) 6, 984-993.

Involvement of Mcl-1 in multiple myeloma is reported in *European Journal of Immunology* (2004) 34, 3156-3164.

Involvement of Mcl-1 in non-Hodgkin's lymphoma is reported in *British Journal of Haematology* (2002) 116, 158-161.

Involvement of Mcl-1 in oligodenroglioma is reported in *Cancer* (1999) 86, 1832-1839.

Involvement of Mcl-1 in ovarian cancer is reported in *Journal of Clinical Oncology: Official Journal of the American Society of Clinical Oncology* (2000) 18, 3775-3781.

Involvement of Mcl-1 in ovarian cancer is also reported in *Molecular Genetics, Gastrointestinal Carcinoma and Ovarian Carcinoma* (2005) 4, 479-486.

Involvement of Mcl-1 in pancreatic cancer is reported in *Oncology* (2002) 62, 354-362.

Involvement of Mcl-1 in peripheral T-cell lymphoma is reported in *Journal of Pathology* (2003) 200, 240-248.

Over-expression of Bcl-2 family protein members is associated with resistance to chemotherapy and is correlated with clinical outcome, disease progression, overall prognosis or a combination thereof in various hematologic and solid tumor types Examples of diseases or disorders associated with the hyperactivity of the Bcl-2 family of proteins, particularly Mcl-1, that can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that compounds having formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

In one embodiment, a compound of the invention (e.g., a compound of formula I), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

In another embodiment, the present invention provides for compositions for treating diseases in a patient during which is expressed or overexpressed an anti-apoptotic Bcl-2 family protein, said compositions comprising an excipient and a therapeutically effective amount of the compound of either formula I and a therapeutically effective amount of one additional therapeutic agent or more than one additional therapeutic agent.

The compounds of the invention can be used alone, in combination with other compounds of the present invention, or in combination with one or more other agent(s). Further, the present invention provides a method for preventing, modulating, or treating the diseases as defined above and hereinafter, wherein a therapeutically effective amount of a combination of a compound of formula I and another compound of formula I and/or at least one other type of therapeutic agent, is administered to a mammalian, e.g., human, patient in need of treatment.

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an anticancer agent or other pharmaceutically active material.

Depending upon the particular condition, or disease, to be treated, additional therapeutic agents, which are normally administered to treat that condition, are optionally present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention are also combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents are optionally administered separately from an inventive compound-containing composition, as part of a multiple dosage regimen. Alternatively, those agents are optionally part of a single dosage form, mixed together with a compound of this invention in a single composition. If administered as part of a multiple dosage regime, the two active agents are submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention is administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that is combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention act synergistically. Therefore, the amount of additional therapeutic agent in such compositions will be less than that required in a monotherapy utilizing only that therapeutic agent. In such compositions a dosage of between 0.01-1,000 g/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, are optionally incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects are prevented or mitigated by pre-coating the device with a pharmaceutically acceptable composition comprising a kinase inhibitor. Implantable devices coated with a compound of this invention are another embodiment of the present invention.

The compounds of the present invention may be employed in adjunct with other therapies, including conventional surgery, radiotherapy and chemotherapy, for the treatment of cancer.

Such therapies can include one or more of the following categories of anti-cancer agents: alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Examples of suitable alkylating agents include altretamine, AMD-473, AP-5280, apaziquone, bendamustine, brostallicin, busulfan, carboquone, carmustine (BCNU), chlorambucil, Cloretazine™ (VNP 40101 M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Examples of suitable angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Examples of suitable aurora kinase inhibitors include AZD-1152, MLN-8054, VX-680 and the like.

Examples of suitable antimetabolites include ALIMTA® (pemetrexed disodium, L Y231514, MTA), 5 azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflomithine, E1CAR (5-ethynyl-1-—-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-I, tiazofurin, tegafur, TS-1, vidarabine, UFT and the like.

Examples of suitable Bcl protein family member inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethyl amino)-1-((phenylsulfanyl)methyl)propyl)amino)-3-nitrobenzenesulfonamide) (AB T-737), N-(4-(4-((2-(4-chlorophenyl)-5,5-dimethyl-1-cyclohex-I-en-1-yl)methyl)piperazin-1-yl)benzoyl)-4-(((1R)-3-(morpholin-4-yl)-I-((phenylsulfanyl)methyl)propyl)amino)-3-((trifluoromethyl)sulfonyl)benzenesulfonamide (ABT-263), N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitro benzenesulfonamide) (ABT-737), ABT-199, GX-070 (obatoclax) and the like.

Examples of suitable Bcr-Abl kinase inhibitors include DASATINIB® (BMS-354825), GLEEVEC® (imatinib) and the like.

Examples of suitable CDK inhibitors include AZD-5438, BMI-I040, BMS-032, BMS-387, CVT-2584, flavopyridol, GPC-286199, MCS-5A, PD0332991, PHA-690509, seliciclib (CYC-202, R-roscovitine), ZK-304709 and the like.

Examples of suitable COX-2 inhibitors include ARCOXIA® (etoricoxib), BEXTRA® (valdecoxib), BMS347070, CELEBREX™ (celecoxib), COX-189 (lumiracoxib), CT-3, DERAMAXX® (deracoxib), 1TE-522, 4-methyl-2-(3,4-dimethylphenyl)-I-(4sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

Examples of suitable EGFR inhibitors include ABX-EGF, anti-EGFr immunoliposomes, EGF-vaccine, EMD-7200, ERBITUX® (cetuximab), HR3, 19A antibodies, IRESSA® (gefitinib), TARCEVA® (erlotinib or OS1-774), TP-38, EGFR fusion protein, TYKERB® (lapatinib) and the like.

Examples of suitable ErbB2 receptor inhibitors include CP-724-714, C1-I033 (canertinib), Herceptin® (trastuzumab), TYKERB® (lapatinib), OMNITARG® (2C4, petuzumab), TAK-165, GW-572016 (ionafamib), GW-282974, EKB-569, P1-166, dHER2 (HER2 vaccine), APC-8024 (HER-2 vaccine), anti-HER12neu bispecific antibody, B7.her21gG3, AS HER2 trifunctional bispecfic antibodies, mAB AR-209, mAB 2B-1 and the like.

Examples of suitable histone deacetylase inhibitors include depsipeptide, LAQ-824, MS-275, trapoxin, suberoylanilide hydroxamic acid (SAHA), TSA, valproic acid and the like.

Examples of suitable HSP-90 inhibitors include 17-AAG-nab, 17-AAG, CNF-I01, CNF-1010, CNF-2024, 17-DMAG, geldanamycin, 1P1-504, KOS-953, MYCOGRAB®, NCS-683664, PU24FC1, PU3, radicicol, SNX-2112, STA-9090 VER49009 and the like.

Examples of suitable MEK inhibitors include ARRY-142886, ARRY-438162 PD-325901, PD-98059 and the like.

Examples of suitable activators of death receptor pathway include TRAIL, antibodies or other agents that target death receptors (e.g., DR4 and DR5) such as Apomab, conatumumab, ETR2-ST01, GDC0145, lexatumumab, HGS-1029, LBY-135, PRO-1762 and trastuzumab.

Examples of suitable mTOR inhibitors include AP-23573, CC 1-779, everolimus, RAD-OO1, rapamycin, temsirolimus and the like.

Examples of suitable non-steroidal anti-inflammatory drugs include AM1GES1C® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetm), LODINE® (etodolac), TORADOL® (ketorolac), DAYPRO® (oxaprozin) and the like.

Examples of suitable platinum chemotherapeutics include cisplatin, ELOXATIN® (oxaliplatin) eptaplatin, lobaplatin, nedaplatin, PARAPLATIN® (carboplatin), satrap latin and the like.

Examples of suitable polo-like kinase inhibitors include B1-2536 and the like.

Examples of suitable thrombospondin analogs include TSP-1 and the like.

Examples of suitable VEGFR inhibitors include AVASTIN® (bevacizumab), AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), vatalanib (PTK-787, ZK-222584), SUTENT® (sunitinib, SU-11248), VEGF trap, vatalanib, ZACTIMA (vandetanib, ZD-6474) and the like.

Examples of suitable antibiotics include intercalating antibiotics aclarubicin, actinomycin D, amrubicin, annamycin, adriamycin, BLENOXANE® (bleomycin), daunorubicin, CAEL YX® or MYOCET® (doxorubicin), elsamitrucin, epirbucin, glarbuicin, ZA VEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Examples of suitable topoisomerase inhibitors include aclarubicin, 9-aminocamptothecin, amonafide, BN-80915, CAMPTOSAR® (irinotecan hydrochloride). amptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Examples of suitable antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, P ANOREX® (edrecolomab), RENCAREX® (WX G250), RITUXAN® (rituximab), ticilimumab, trastuzimab and and the like.

Examples of suitable hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Examples of suitable deltoids and retinoids include seocalcitol (EB1089, CB1093), lexacalcitrol (KH1060), fenretinide, PANRETIN® (aliretinoin), ATRAGEN® (liposomal tretinoin), TARGRETIN®(bexarotene), LGD-1550 and the like.

Examples of suitable plant alkaloids include, but are not limited to, vincristine, vinblastine, vindesine, vinorelbine and the like.

Examples of suitable PARP inhibitors include olaparib, KU-59436, ABT-888, AZD-2281, AG-014699, BSI-201, BGP-15, INO-IOOI, ONO-2231 and the like.

Examples of suitable proteasome inhibitors include VELCADE® (bortezomib), MG132, NPI-0052, PR-171 and the like.

Examples of suitable immunologicals include interferons and other immune-enhancing agents. Interferons include interferon alpha, interferon alpha-2a, interferon alpha-2b, interferon beta,interferon gamma-la, ACTIMMUNE® (interferon gamma-lb), or interferon gamma-nl, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE®(lenograstim), lentinan, leukocyte alpha interferon, imiquimod, MDX-010, melanomavaccine, mitumomab, molgramostim, MYLOTARG™® (gemtuzumab ozogamicin). NEUPOGEN® (filgrastlm), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-1OO, WF-1O, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Examples of suitable purine analogs include LANVIS® (thioguanine) and PURI-NETHOL® (mercaptopurine).

Examples of suitable antimitotic agents include batabulin, epothilone D (KOS-862), N-(2-((4-hydroxyphenyl)amino) pyridin-3-yl)-4-methoxybenzenesulfonamide, ixabepilone (BMS 247550), paclitaxel, TAXOTERE® (docetaxel), PNUI00940 (109881), patupilone, XRP-9881 (larotaxel), vinflunine, ZK-EPO and the like.

Compounds of the present invention can also be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula I may be combined with other chemotherapeutic agents such as ABRAXANE™ (ABI-007), ADVEXIN®, ALTOCOR® or MEVACOR® (lovastatin), AMPLIGEN® (polyl:poly CI2U, a synthetic RNA), APTOSYN™ (exisulind), AREDIA® (pamidronic acid), arglabin, L-asparaginase, atamestane (1-methyl-3,17-dione-androsta-1,4-diene), A V AGE® (tazarotne), A VE-8062, BEC2 (mitumomab), cachectin or cachexin (tumor necrosis factor), canvaxin (vaccine), CeaVac™ (cancer vaccine), CELEUK® (celmoleukin), CEPLENE®(histamine dihydrochloride), CERVARIX™ (human papillomavirus vaccine), CHOP® (C:CYTOXAN® (cyclophosphamide); H: ADRIAMYCIN® (hydroxydoxorubicin); Vincristine (ONCOVIN®); P: prednisone), CyPat™, combrestatin A4P, DAB(389)EGF or TransMID-I07R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinantvaccine), gastrimmune, genasense, GMK (ganglioside conjugate vaccine), GVAX® (prostate cancer vaccine), halofuginone, histerelin, hydroxycarbamide, ibandronic acid, IGN-101, IL-3-PE38, IL-13-PE38QQR (cintredekin besudotox), IL-13-*pseudomonas* exotoxin, interferon-a, interferon-y, JUNOVAN™ or MEPACT™ (mifamurtide), lonafarnib, 5,10-25 methylenetetrahydrofolate, miltefosine (hexadecylphosphocholine), NEOVASTAT®(AE-941), NEUTREXIN® (trimetrexate glucuronate), NIPENT® (pentostatin), ONCONASE® (aribonuclease enzyme), ONCOPHAGE® (melanoma vaccine treatment), OncoVAX (IL-2Vaccine), ORATHECIN™ (rubitecan), OSIDEM® (antibody-based cell drug), OvaRex®MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEGInterferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PTI00), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio) quinazoline dihydrochloride), TNFerade™ (adenovector: DNA carrier containing the gene for tumor-necrosis factor-a), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alpha vbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

The combination therapy can be administered as a simultaneous or sequential regimen. When administered sequentially, the combination can be administered in two or more administrations. The combined administration includes co-administration, using separate formulations or a single pharmaceutical formulation, and consecutive administration in either order, wherein preferably there is a time period while both (or all) active agents simultaneously exert their biological activities.

The above other therapeutic agents, when employed in combination with the compounds of the present invention may be used, for example, in those amounts indicated in the *Physicians' Desk Reference*, as in the patents set out above, or can be lowered due to the combined action (synergy) of the newly identified agent and other chemotherapeutic agents or treatments as determined by one of ordinary skill in the art.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

The compounds of formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating cancers and related diseases, a pharmaceutical composition will be employed containing the compounds of formula I, with or without other anticancer agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of formula I (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of a compound of formula I into a vial, aseptically freeze-drying and sealing. For use, the contents of the vial are mixed with 2 mL of physiological saline, to produce an injectable preparation.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein.

The compounds of the invention may be prepared using the exemplary reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One having ordinary skill in the art may adjust one or more of the conditions described herein. One skilled in the art of organic synthesis understands that the functionality present on various portions of the edict molecule must be compatible with the reagents and reactions proposed. Not all compounds of the invention falling into a given class may be compatible with some of the reaction conditions required in some of the methods described. Such restrictions to the substituents, which are compatible with the reaction conditions, will be readily apparent to one skilled in the art and alternate methods can be used.

Scheme 1

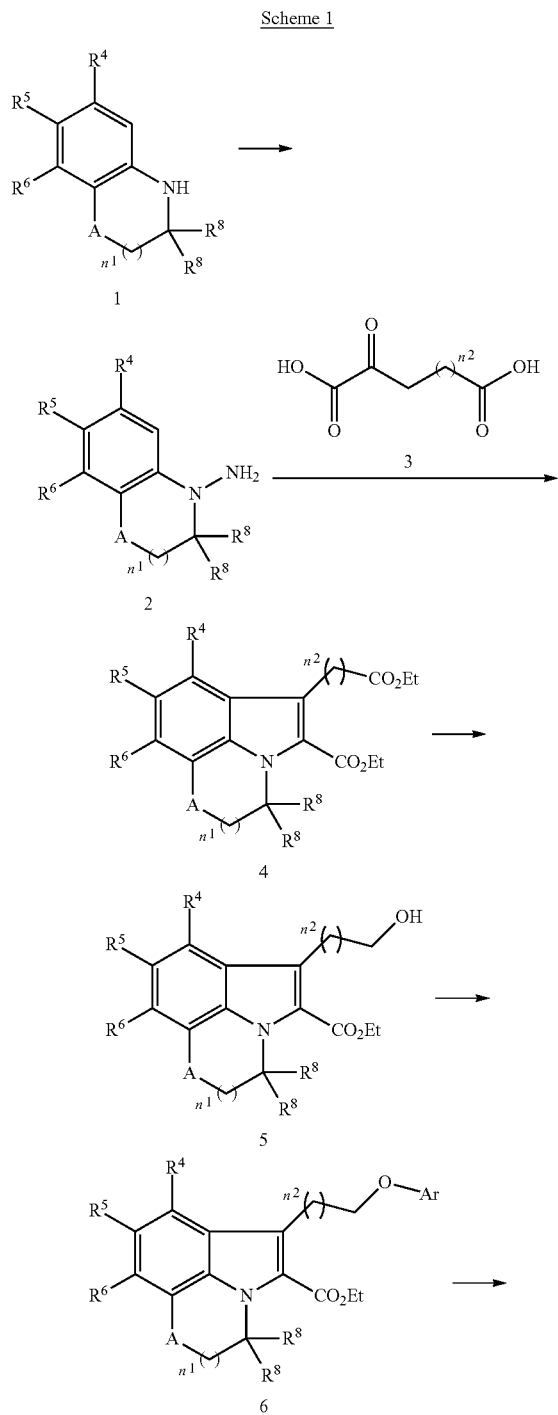

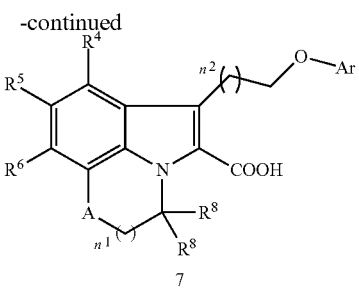

In some embodiments, provided compounds of this invention may be prepared as shown in Scheme 1. In some embodiments, $n^1$ is 1, 2 or 3 in any of the compounds of Scheme 1. In some embodiments, $n^2$ is 1, 2 or 3 in any of the compounds of Scheme 1. Each of $R^4$, $R^5$ and $R^6$ is as defined and described in embodiments herein. In some embodiments, $R^8$ in any of the compounds of Scheme 1 is hydrogen or a "monovalent substituent" as defined herein. In some embodiments, $R^8$ is hydrogen, $C_{1-4}$ alkyl or halogen in any of the compounds of Scheme 1. Preparation of an aryl hydrazine 2 can be accomplished, for example, by treatment of a corresponding substituted heterobicyclic aniline 1 with $NaNO_2$ followed by reduction of the N-nitroso intermediate with a reducing agent such as LAH. The core tricyclic indole intermediate 4 can be constructed via Fischer indole cyclization of the aryl hydrazine 2 and a suitably substituted ketone (i.e., 3) by methods described by, but not limited to, R. J. Sundberg, "Indoles, Best Synthetic Methods" 1996, Academic Press, San Diego, Calif. The ethyl ester functional group at the flexible linker of indole 4 can be selectively reduced with excess $BH_3$, and the resulting alcohol 5 can be condensed with a suitably substituted phenol or hydroxyheterocycle via Mitsunobu reaction (described by, but not limited to, I. D. Jenkens and O. Mitsunobu, "Electronic Encyclopedia of Reagents for Organic Synthesis" (Ed.: L. A. Paquette), 2001, John Wiley & Sons) to give the aryl ether 6 using, but not limited to, DEAD or Dt-BuAD. Indole acid 7 can be generated by saponification of the ethyl ester group of compound 6 with appropriate aqueous bases, such as $Cs_2CO_3$, $K_2CO_3$, KOH, LiOH or NaOH, using a number of conditions that are routine for those skilled in the art of organic synthesis.

Scheme 2

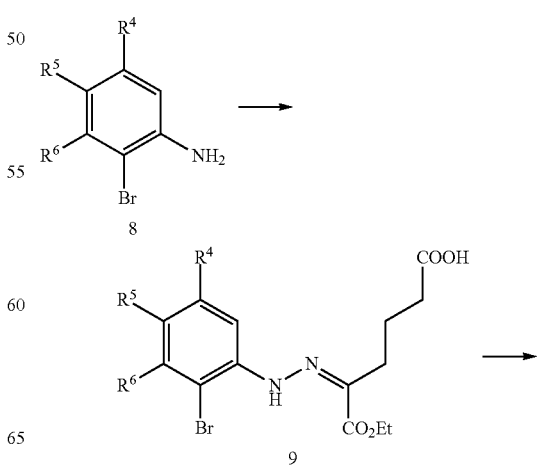

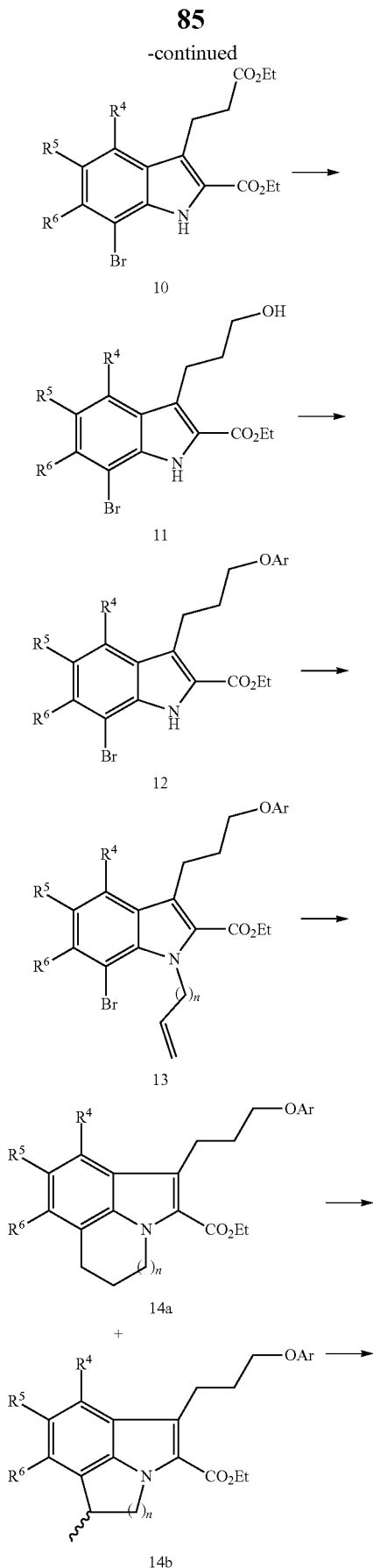

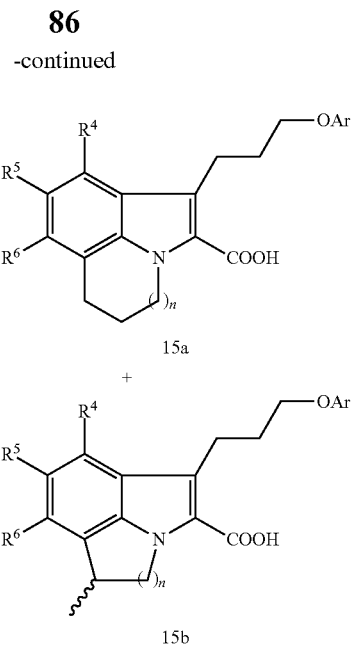

Compounds of Formula 15a and 15b may be prepared as shown in Scheme 2. In some embodiments, n is 1, 2, 3 or 4 in any of the compounds in Scheme 2. Each of $R^4$, $R^5$ and $R^6$ is as defined and described in embodiments herein. Indole 10, for example, can be assembled by using Japp-Klingemann reaction described by, but not limited to, F. G. Salituro, et al. *J. Med. Chem.* (1990) 33, 2944-2946 as follows. Aniline 8, containing ortho-Br, can be converted to the corresponding benzenediazonium intermediate followed by condensation with ethyl 2-oxocyclopentanecarboxylate to give hydrazone 9. Subsequent intramolecular Fisher indole cyclization of the intermediate 9 can give 7-Br-indole 10. Aryl ether 12 can be produced using selective reduction by excess $BH_3$ follow by Mitsunobu condensation of a suitably substituted phenol as shown in Scheme 1. The indole NH of the intermediate 12 can be alkylated with a vinyl alkyl halide with a proper length under treatment of a base, for example, $Na_2CO_3$, $CsCO_3$, $K_2CO_3$, $Et_3N$ or NaH in an appropriate solvent such as, but not limited to, DMF, $CH_2Cl_2$, THF or $Et_2O$ to generate a vinyl indole 13. The third ring of the indole core 14a and 14b can be constructed by condensing the terminal vinyl group to the 7-Br of indole using a radical initiator such as, but not limited to, AIBN, ABCN, di-tert-butyl peroxide or benzoyl peroxide. Tricyclic indole acids 15a and 16b can be generated by saponification from corresponding indole esters 14a and 14b.

Scheme 3

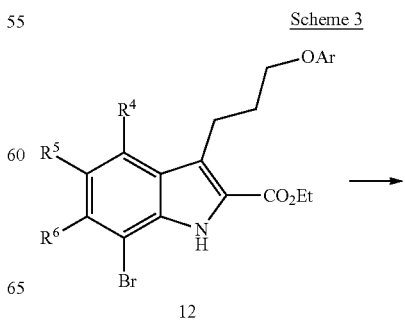

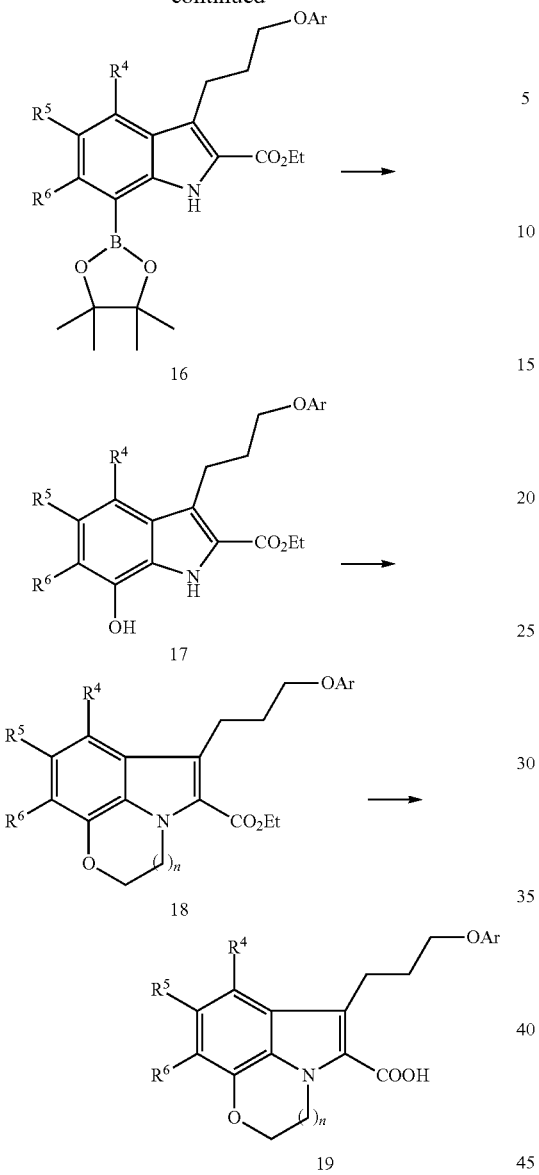

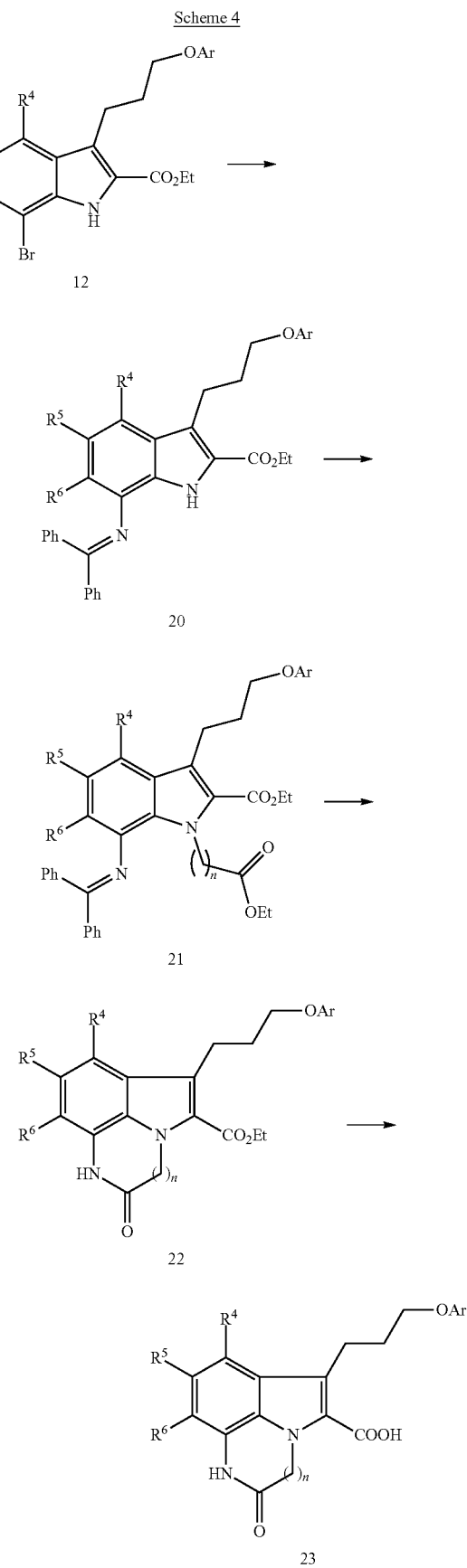

Scheme 4

In some embodiments, compounds of Formula 19 with —O— containing c-ring units may be synthesized by procedures illustrated in Scheme 3. In some embodiments, n is 1, 2 or 3 in any of the compounds in Scheme 3. Each of $R^4$, $R^5$ and $R^6$ is as defined and described in embodiments herein. Previously described compounds of Formula 12 baring 7-Br group can be converted to the pinacol-borate 16 by coupling bis(pinacolato)diborn in the presence of a catalytic Pd species (i.e. $Pd(PPh_3)_4$, $Pd(PPh_3)_2Cl_2$, $Pd(OAc)_2$, $Pd_2(dba)_3$, $Pd(dppf)Cl_2$). 7-Hydroxy indole 17 can be prepared by oxidation of the borate 16 using, without limitation, $H_2O_2$, ONOOH, or HOCl. Subsequent cyclization via intramolecular double alkylations with a di-haloalkane such as $Br(CH_2)_2Br$ or $Br(CH_2)_3Br$ in the presence of a base such as $Na_2CO_3$, $CsCO_3$, $K_2CO_3$, $Et_3N$ or NaH in an appropriate solvent such as DMF, $CH_2Cl_2$, THF or $Et_2O$ can yield tricyclic indole 18. Finally, the morpholino-tricyclic indole acid 19 can be obtained by saponification of ester 18 as described above.

Compounds 23 containing the lactam c-ring moiety can be synthesized by procedures depicted in Scheme 4 using previously described the intermediate 12. In some embodiments, n is 1, 2 or 3 in any of the compounds in Scheme 4. Each of $R^4$, $R^5$ and $R^6$ is as defined and described in embodiments herein. Coupling of benzophenone imine at the 7-position of indole 12 employing Buchwald Hartwig cross-coupling method (described by, but not limited to, J. P. Wolfe et. al. *Tetrahedron. Lett.* (1997), 38, 6367-6370) in the presence of a catalytic Pd species, such as $Pd(PPh_3)_4$, $Pd(PPh_3)_2Cl_2$, $Pd(OAc)_2$, $Pd_2(dba)_3$, or $Pd(dppf)Cl_2$, a suitable ligand (i.e. BINAP, BrettPhos, RuPhos, etc.), and a base such as t-BuONa, $CsCO_3$, KOH, LiHMDS, or NaHMDS can produce di-phenylketimine 20. Substitution at the NH with a halo-alkylester can be achieved by employing an appropriate base such as, but not limited to, $Cs_2CO_3$, $K_2CO_3$, NaH, NaHMDS, or LiHMDS at a number of conditions that are routine for those skilled in the art of organic synthesis to give an adduct 21. Selective hydrolysis of ketamine followed by cyclization using mild aqueous acid can give lactam 22 which can be converted to tricyclic indole acid 23 containing the piperazinone c-ring moiety by previously described saponification.

Alternatively, the intermediate 22 can be substituted at the lactam NH to produce compound 24 utilizing a variety of base catalyzed alkylation conditions for a secondary amide with an alkylhalide or alkylsulfonates that are well known by those skilled in the art. In some embodiments, n is 1, 2 or 3 in any of the compounds in Scheme 5. Each of $R^1$, $R^4$, $R^5$ and $R^6$ is as defined and described in embodiments herein. Standard saponification can be applied to obtain the N-substituted piperazinone-indole acid 25. The intermediate 24 can be also reduced by reducing agents such as, but not limited to $BH_3$ in an appropriate solvent such as $Et_2O$ or THF to give the piperazine derivative 26 which can be converted to the tricyclic indole acid 27 containing a N-substituted piperazine via saponification as described previously.

Scheme 6

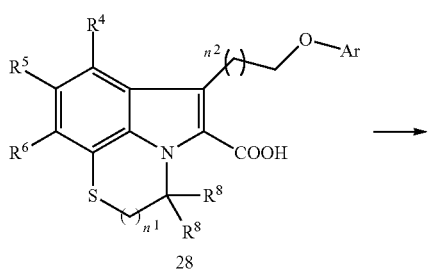

28

Scheme 5

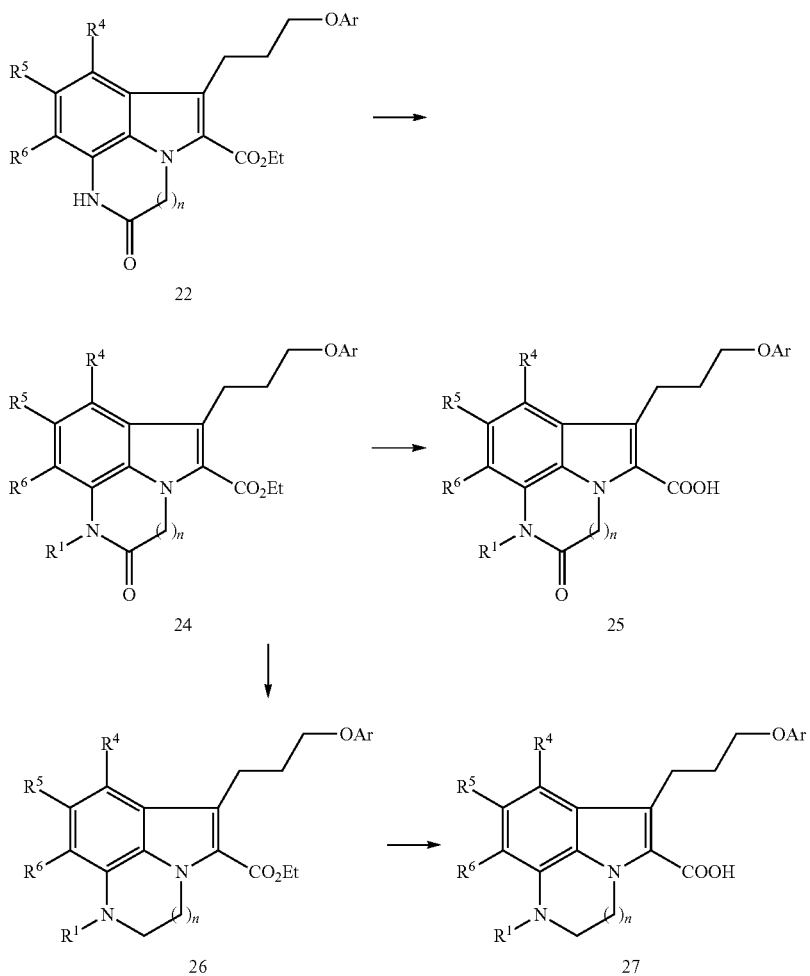

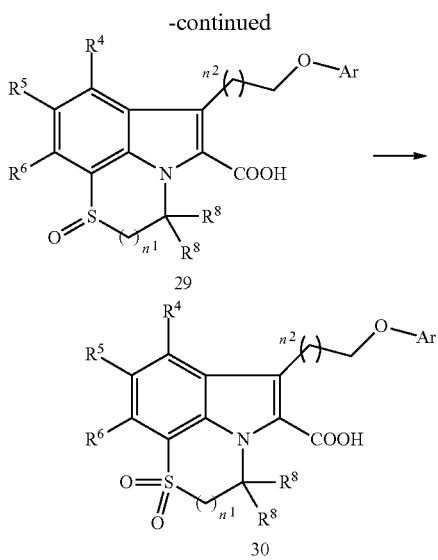

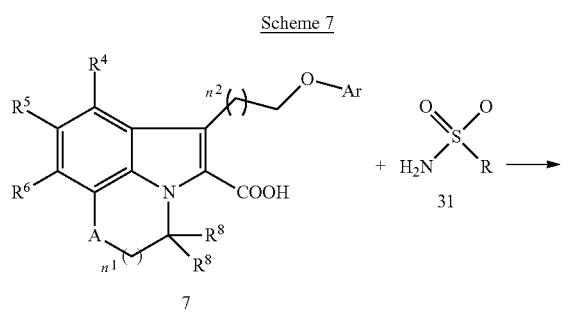

Preparation of compounds 29 and 30 with different oxidation states of the sulfur in the third ring is outlined in Scheme 6. In some embodiments, $n^1$ is 1, 2 or 3 in any of the compounds of Scheme 6. In some embodiments, $n^2$ is 1, 2 or 3 in any of the compounds of Scheme 6. Each of $R^4$, $R^5$ and $R^6$ is as defined and described in embodiments herein. In some embodiments, $R^8$ in any of the compounds of Scheme 6 is hydrogen or a "monovalent substituent" as defined herein. In some embodiments, $R^8$ is hydrogen, $C_{1-4}$ alkyl or halogen in any of the compounds of Scheme 6. Indole acid 28 containing the sulfide group in the third ring can be oxidized to the corresponding sulfoxide 29 with a oxidizing agent such as, but not limited to, $H_2O_2$, mCPBA or periodic acid. Sulfone 30 can be also synthesized from sulfoxide 29 or sulfide 28 by employing a similar oxidation condition described above with a higher equivalence of an oxidizing agent and/or extended reaction time.

Scheme 7

Tricyclic indole acylsulfonamides of Formula 32 can be produced by coupling of carboxylic acids of Formula 7 with a variety of sulfonamides of Formula 31 using a coupling reagent, but not limited to, PyBOP, DCC, EDC, HBTU, or TBTU at a number of conditions that are routine for those skilled in the art of organic synthesis. In some embodiments, $n^1$ is 1, 2 or 3 in any of the compounds of Scheme 7. In some embodiments, $n^2$ is 1, 2 or 3 in any of the compounds of Scheme 7. Each of R, $R^4$, $R^5$ and $R^6$ is as defined and described in embodiments herein. In some embodiments, R in any of the compounds of Scheme 7 is hydrogen or a "monovalent substituent" as defined herein. In some embodiments, $R^8$ is hydrogen, $C_{1-4}$ alkyl or halogen in any of the compounds of Scheme 7.

Scheme 8

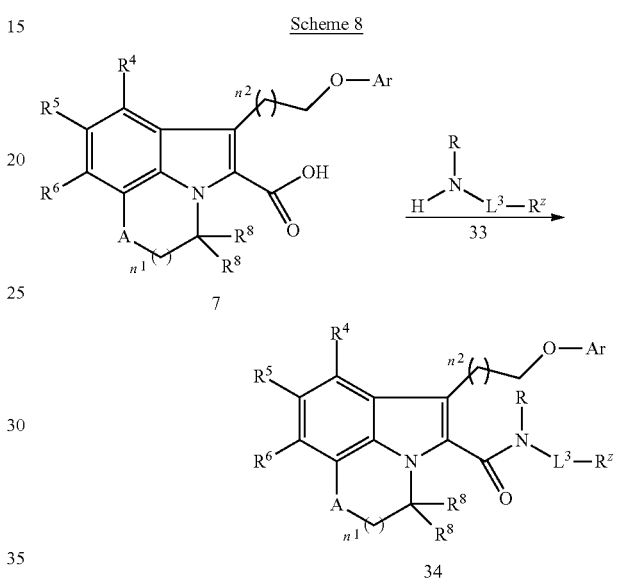

Tricyclic indole amide derivatives of Formula 34 can be also prepared from carboxylic acids of Formula 7 with suitably substituted amines of Formula 33 using coupling reagents including, but not limited to, PyBOP, DCC, EDC, HBTU, or TBTU at conditions that are routine for those skilled in the art of organic synthesis. In some embodiments, $n^1$ is 1, 2 or 3 in any of the compounds of Scheme 8. In some embodiments, $n^2$ is 1, 2 or 3 in any of the compounds of Scheme 8. Each of R, $R^4$, $R^5$, $R^6$, $L^3$ and $R^z$ is as defined and described in embodiments herein. In some embodiments, $R^8$ in any of the compounds of Scheme 8 is hydrogen or a "monovalent substituent" as defined herein. In some embodiments, $R^8$ is hydrogen, $C_{1-4}$ alkyl or halogen in any of the compounds of Scheme 8.

ABBREVIATIONS

The following abbreviations are employed in the Examples and elsewhere herein:
Dt-BuAD=di-tert-butyl azodicarboxylate
DCM=dichloromethane
EDC=1-Ethyl-3-(3-dimethylaminopropyl)carbodiimide
TEA=triethylamine
i-Pr$_2$NEt=N-ethyl-N-isopropylpropan-2-amine
Rochelle salt=Potassium sodium tartrate aqueous solution
LAH=LIthium aluminium hydride
PyBOP=benzotriazol-1-yl-oxytripyrrolidinophosphonium hexafluorophosphate
DMAP=dimethylamino pyridine
mCPBA=meta-chloroperoxybenzoic acid HOBT=hydroxybenzotriazole
DBU=1,8-Diazabicycloundec-7-ene
DMF=dimethylformamide
DMSO=dimethylsulfoxide
THF=tetrahydrofuran
$K_2CO_3$=potassiumm carbonate
$Cs_2CO_3$=cesium carbonate
$H_2O_2$=hydrogen peroxide
ONOOH=peroxynitrous acid
HOCl=Hypochlorous acid
DME=1,2-dimethoxyethane
t-BuONa=sodium tert-butoxide
LDA=lithium di-isopropylamide
AIBN=Azobisisobutyronnitrile
ABCN=1,1'-Azobis(cyclohexanecarbonitrile)
NaHMDS=sodium hexamethyldisilazide
LiHMDS=lithium hexamethyldisilazide
mCPBA=meta-chlroperbenzoic acid
n-BuLi=n-butyl lithium
ether=diethyl ether
NaOH=sodium hydroxide
KOH=potassium hydroxide
EtOAc=ethyl acetate
$Na_2CO_3$=sodium carbonate
$Na_2SO_4$=sodium sulfate
$MgSO_4$=magnesium sulfate
$SiO_2$=silicon dioxide
$CH_2Cl_2$=methylene chloride
MeOH=methanol
EtOH=ethanol
Hex=hexanes
HCl=hydrochloric acid
Pd(dppf)$Cl_2$=[1,1'-bis(diphenylphosphino)ferrocene]dichloropalladium (II)
$Pd_2(dba)_3$=tris(dibenzylideneacetone)dipalladium (0)
Pd(PPh$_3$)$_4$=tetrakis(triphenylphosphine)palladium(0)
TFA=trifluoroacetic acid
Et$_3$N=triethylamine
DIPEA=N,N-diisopropylethylamine
DEAD=diethyl azodicarboxylate
TBAD=dit-butyl azodicarboxylate
min=minute(s)
h or hr=hour(s)
mL or ml=milliliter
g=gram(s)
mg=milligram(s)
mmol=millimole(s)
rt=room temperature
aq.=aqueous
MS=mass spectrometry
NMR=nuclear magnetic resonance

EXAMPLES

The following Examples are offered as illustrative as a partial scope and particular embodiments of the invention and are not meant to be limiting of the scope of the invention.

Abbreviations and chemical symbols have their usual and customary meanings unless otherwise indicated. Unless otherwise indicated, the compounds described herein have been prepared, isolated and characterized using the Schemes and other methods disclosed herein or may be prepared using the same or similar procedures.

Example 1

Preparation of 6-(2-(naphthalen-1-yloxy)ethyl)-2,3-dihydro-[1,4]thiazino[2,3,4-hi]indole-5-carboxylic acid, I-1

Step A. Preparation of 3,4-dihydro-2H-benzo[b][1,4]thiazine

To a solution of 2-aminobenzenethiol (2.0 g, 16 mmol) and 1,2-dibromoethane (3.6 g, 19 mmol) in THF (40 mL) was added and i-Pr$_2$NEt (4.9 g, 38 mmol) with stirring 1 h at rt. The reaction mixture was concentrated and dissolved in MeOH (5.0 mL). NaBH$_4$ (590 mg, 16 mmol) was added, and the reaction mixture was refluxed for 8 h. The reaction mixture was concentrated and quenched by addition of 10% Rochelle salt (20 mL). It was extracted with CH$_2$Cl$_2$ (3×20 mL) and concentrated in vacuo. The residue was purified by flash chromatography (Combi-flash Rf Hex/EtOAc 0-100% gradient) to give the title compound. MS (ES) 152.1 (M+H).

Step B. Preparation of 4-nitroso-3,4-dihydro-2H-benzo[b][1,4]thiazine

To a biphasic solution of 3,4-dihydro-2H-benzo[b][1,4] thiazine (16 mmol) in CH$_2$Cl$_2$ (24 mL) and aq. H$_2$SO$_4$ (1M, 24 mL) was added NaNO$_2$ (1.1 g, 16 mmol) at rt. The reaction mixture was stirred for 1.5 h at rt then layers were separated. The aqueous layer was extracted with CH$_2$Cl$_2$ (3×10 mL). The combined organic solution was concentrated in vacuo, and the residue was purified by flash chromatography (Combi-flash Rf Hexane/EtOAc gradient 0-100%) to give the title compound as a yellow oil in 2.1 g (11.7 mmol). MS (ES) 181.0 (M+H).

Step C. Preparation of 2,3-dihydro-4H-benzo[b][1,4]thiazin-4-amine

To a solution of 4-nitroso-3,4-dihydro-2H-benzo[b][1,4] thiazine (2.1 g, 11.7 mmol) in THF (32 mL) was slowly added LAH (610 mg, 16 mmol) at 50° C. under N$_2$ atmosphere. The reaction mixture was stirred for 10 min at 50° C. then quenched by sequential addition of H$_2$O (0.7 mL), aq. 3N NaOH (0.7 mL) and H$_2$O (2.1 mL). The mixture was filtered through celite, and the filtrate was concentrated in vacuo. The residue was purified by flash chromatography (Combi-flash Rf Hexane/EtOAc gradient 0-50%) to give the title compound as a yellow oil in 1.5 g (9.0 mmol). MS (ES) 167.1 (M+H).

Step D. Preparation of 6-(2-ethoxy-2-oxoethyl)-2,3-dihydro-[1,4]thiazino[2,3,4-hi]indole-5-carboxylic acid A solution of 2,3-dihydro-4H-benzo[b][1,4]thiazin-4-amine (336 mg, 2.0 mmol) and 2-oxopentanedioic acid (325 mg, 2.2 mmol) in EtOH (5 mL) was stirred at 50° C. for 30 min then cooled to 0° C. To the reaction mixture was added conc. H$_2$SO$_4$ (0.5 mL) dropwise at 0° C., under N$_2$ atmosphere. The reaction mixture was stirred for 2 h at 60° C. then quenched by pouring into ice then extracted with CH$_2$Cl$_2$. The combined organic layer was washed with sat. NaHCO$_3$, water, brine, dried over MgSO$_4$, filtered and concentrated in vacuo. The residue was purified by flash chromatography (Combi-flash Rf Hex/EtOAc 25% gradient)

Step E. Preparation of methyl 6-(2-ethoxy-2-oxo-ethyl)-2,3-dihydro-[1,4]thiazino[2,3,4-hi]indole-5-carboxylate To a solution of 6-(2-ethoxy-2-oxoethyl)-2,3-dihydro-[1,4]thiazino[2,3,4-hi]indole-5-carboxylic acid (145 mg, 0.47 mmol) in of MeOH and benzene mixture (1:10, 2.0 mL) was added TMSCHN$_2$ (2M in hexane) until bubbling stopped and a yellow color of the reaction mixture persisted. The reaction mixture was stirred for additional 10 min at rt then concentrated in vacuo to give the title product. It was directly used for the subsequent step without further purification.

Step F. Preparation of methyl 6-(2-hydroxyethyl)-2,3-dihydro-[1,4]thiazino[2,3,4-hi]indole-5-carboxylate To a solution of methyl 6-(2-ethoxy-2-oxoethyl)-2,3-dihydro-[1,4]thiazino[2,3,4-hi]indole-5-carboxylate (0.47 mmol) in THF (2.0 mL) was added BH$_3$ in THF (2 mL, 2 mmol) at 20° C. The reaction mixture was stirred for 5 h at 20° C. and quenched by addition of MeOH then concentrated in vacuo. The residue was purified by flash chromatography (Combi-flash Rf Hexane/EtOAc gradient 0-100%) to give the title compound as a colorless oil in 110 mg (0.40 mmol). MS (ES) 278.1 (M+H).

Step G. Example 1

To a solution of methyl 6-(2-hydroxyethyl)-2,3-dihydro-[1,4]thiazino[2,3,4-hi]indole-5-carboxylate (50 mg, 0.18 mmol), PPh$_3$ (71 mg, 0.27 mmol) and naphthalen-1-ol (44 mg, 0.28 mmol) in THF (1.0 mL) was added Dt-BuAD (62 mg, 0.27 mmol) at 20° C. The reaction mixture was stirred for 15 h at 20° C. To the reaction mixture was added KOH (101 mg, 10 mmol) and MeOH (1.0 mL). The reaction mixture was stirred for 2 h at 65° C. then concentrated in vacuo. The crude product was purified by reverse phase prep. HPLC (Phenomenex Gemini C18, H$_2$O/CH$_3$CN gradient to 95% CH$_3$CN 0.1% TFA) to yield the title compound (43 mg, 0.11 mmol) as a light yellow solid. MS (ES) 390.1 (M+H).

Example 2

Preparation of N-(methylsulfonyl)-6-(2-(naphthalen-1-yloxy)ethyl)-2,3-dihydro-[1,4]thiazino[2,3,4-hi]indole-5-carboxamide, I-2

To a solution of 6-(2-(naphthalen-1-yloxy)ethyl)-2,3-dihydro-[1,4]thiazino[2,3,4-hi]indole-5-carboxylic acid (12 mg, 0.030 mmol), methanesulfonamide (3.1 mg, 0.033 mmol) and PyBOP (19 mg, 0.036 mmol) in CH$_2$Cl$_2$ (1.0 mL) was added i-Pr$_2$NEt (16 µL, 0.090 mmol) at 20° C. The reaction mixture was stirred for 1 h at 20° C. then quenched by addition of 0.5 N aq. HCl. The quenched reaction mixture was extracted with CH$_2$Cl$_2$ and concentrated in vacuo. The residue was purified by flash chromatography (Combi-flash Rf Hexane/EtOAc gradient 0-20%) to give the title compound (2.0 mg, 0.0043 mmol) as a white solid. MS (ES) 467.1 (M+H).

Example 3

Preparation of 6-(2-(4-chloro-3,5-dimethylphenoxy)ethyl)-2,3-dihydro-[1,4]thiazino[2,3,4-hi]indole-5-carboxylic acid, I-3

The title compound was prepared (47 mg, 0.12 mmol) as a white solid according to procedures described in Example 1, Step F, using methyl 6-(2-hydroxyethyl)-2,3-dihydro-[1,4]thiazino[2,3,4-hi]indole-5-carboxylate (50 mg, 0.18 mmol) and substituting naphthalen-1-ol with 4-chloro-3,5-dimethylphenol (39 mg, 0.25 mmol). MS (ES) 402.1 (M+H); $^1$H NMR (400 MHz, DMSO-d$_6$) δ 8.07 (d, J=8.0 Hz, 1H), 7.75 (d, J=7.2 Hz, 1H), 7.30 (t, J=7.7 Hz, 1H), 6.75 (s, 2H), 5.26 (dt, J=14.4, 3.8 Hz, 1H), 4.45 (ddd, J=14.9, 12.8, 2.7 Hz, 1H), 4.19-4.04 (m, 2H), 3.65-3.51 (m, 3H), 3.18 (ddd, J=14.1, 12.6, 3.9 Hz, 1H), 2.26 (s, 6H).

Example 4

Preparation of 1-(2-(naphthalen-1-yloxy)ethyl)-5,6-dihydro-4H-pyrrolo[3,2,1-ij]quinoline-2-carboxylic acid, I-4

Step A. Preparation of 1-nitroso-1,2,3,4-tetrahydroquinoline

The title compound was prepared as a white solid according to procedures described in Example 1, Step B, by substituting 3,4-dihydro-2H-benzo[b][1,4]thiazine with 1,2,3,4-tetrahydroquinoline (1.0 g, 7.5 mmol). MS (ES) 163.1 (M+H).

Step B. Preparation of 3,4-dihydroquinolin-1(2H)-amine

The title compound (615 mg, 4.2 mmol, two steps) was prepared as an off-white solid according to procedures described in Example 1, Step C, using 1-nitroso-1,2,3,4-tetrahydroquinoline. MS (ES) 149.1 (M+H).

Step C. Preparation of 1-(2-ethoxy-2-oxoethyl)-5,6-dihydro-4H-pyrrolo[3,2,1-ij]quinoline-2-carboxylic acid The title compound (95 mg, 0.37 mmol) was prepared as a white solid according to procedures described in Example 1, Step D, by substituting 2,3-dihydro-4H-benzo[b][1,4]thiazin-4-amine with 3,4-dihydroquinolin-1(2H)-amine (74 mg, 0.5 mmol). MS (ES) 288.1 (M+H).

Step D. Preparation of methyl 1-(2-ethoxy-2-oxoethyl)-5,6-dihydro-4H-pyrrolo[3,2,1-ij]quinoline-2-carboxylate The title compound was prepared as a white solid according to procedures described in Example 1, Step E, using 1-(2-ethoxy-2-oxoethyl)-5,6-dihydro-4H-pyrrolo[3,2,1-ij]quinoline-2-carboxylic acid.

Step E. Preparation of methyl 1-(2-hydroxyethyl)-5,6-dihydro-4H-pyrrolo[3,2,1-ij]quinoline-2-carboxylate The title compound was prepared as a white solid according to procedures described in Example 1, Step F, using crude methyl 1-(2-ethoxy-2-oxoethyl)-5,6-dihydro-4H-pyrrolo[3,2,1-ij]quinoline-2-carboxylate. MS (ES) 260.1 (M+H).

Step F. Example 4

The title compound was prepared as a white solid according to procedures described in Example 1, Step E, by substituting methyl 6-(2-hydroxyethyl)-2,3-dihydro-[1,4]thiazino[2,3,4-hi]indole-5-carboxylate with methyl 1-(2-hydroxyethyl)-5,6-dihydro-4H-pyrrolo[3,2,1-ij]quinoline-2-carboxylate. MS (ES) 372.2 (M+H); $^1$H NMR (400 MHz, DMSO-$d_6$) δ 8.10 (d, J=8.3 Hz, 1H), 7.83 (d, J=8.1 Hz, 1H), 7.67 (dd, J=7.7, 1.5 Hz, 1H), 7.49 (ddd, J=8.2, 6.8, 1.3 Hz, 1H), 7.45-7.31 (m, 3H), 7.10-7.00 (m, 2H), 6.96 (d, J=7.5 Hz, 1H), 4.50-4.42 (m, 2H), 4.35 (t, J=6.7 Hz, 2H), 3.67 (t, J=6.7 Hz, 2H), 2.92 (t, J=6.1 Hz, 2H), 2.18-2.04 (m, 2H).

Example 5

Preparation of 6-(2-(naphthalen-1-yloxy)ethyl)-2,3-dihydro-[1,4]oxazino[2,3,4-hi]indole-5-carboxylic acid, I-5

Step A. Preparation of 4-nitroso-3,4-dihydro-2H-benzo[b][1,4]oxazine

The title compound was prepared as a white solid according to procedures described in Example 1, Step B, by substituting 3,4-dihydro-2H-benzo[b][1,4]thiazine with 3,4-dihydro-2H-benzo[b][1,4]oxazine. MS (ES) 165.1 (M+H).

Step B. Preparation of 2,3-dihydro-4H-benzo[b][1,4]oxazin-4-amine

The title compound was prepared as an off-white solid according to procedures described in Example 1, Step C, using 4-nitroso-3,4-dihydro-2H-benzo[b][1,4]oxazine. MS (ES) 151.1 (M+H).

Step C. Preparation of 6-(2-ethoxy-2-oxoethyl)-2,3-dihydro-[1,4]oxazino[2,3,4-hi]indole-5-carboxylic acid The title compound (340 mg, 1.2 mmol) was prepared as an off-white solid according to procedures described in Example 1, Step D, by substituting 2,3-dihydro-4H-benzo[b][1,4]thiazin-4-amine with 2,3-dihydro-4H-benzo[b][1,4]oxazin-4-amine (60% yield, 3steps). MS (ES) 290.1 (M+H).

Step D. Preparation of methyl 6-(2-ethoxy-2-oxoethyl)-2,3-dihydro-[1,4]oxazino[2,3,4-hi]indole-5-carboxylate To a solution of 6-(2-ethoxy-2-oxoethyl)-2,3-dihydro-[1,4]oxazino[2,3,4-hi]indole-5-carboxylic acid (340 mg, 1.2 mmol) in THF (12 mL) was added $K_2CO_3$ (196 mg, 1.42 mmol) at rt. The reaction mixture was stirred for 10 min at rt then MeI (160 μL, 1.76 mmol) was added in three portions. The reaction mixture was warmed to 40° C. then stirred for additional 5 h. The reaction was cooled to rt then filtered, and the filtrate was concentrated in vacuo to give the crude title compound. It was used in the subsequent reaction without further purification.

Step E. Preparation of methyl 6-(2-hydroxyethyl)-2,3-dihydro-[1,4]oxazino[2,3,4-hi]indole-5-carboxylate The title compound (150 mg, 0.57 mmol) was prepared as a white solid according to procedures described in Example 1, Step F, using crude methyl 6-(2-ethoxy-2-oxoethyl)-2,3-dihydro-[1,4]oxazino[2,3,4-hi]indole-5-carboxylate (1.2 mmol). MS (ES) 262.1 (M+H).

Step F. Example 5

The title compound was prepared as a white solid according to procedures described in Example 1, Step E, by substituting methyl 6-(2-hydroxyethyl)-2,3-dihydro-[1,4]thiazino[2,3,4-hi]indole-5-carboxylate with methyl 6-(2-hydroxyethyl)-2,3-dihydro-[1,4]oxazino[2,3,4-hi]indole-5-carboxylate. MS (ES) 374.1 (M+H).

Example 6

Preparation of 6-(2-(naphthalen-1-yloxy)ethyl)-N-(phenylsulfonyl)-2,3-dihydro-[1,4]oxazino[2,3,4-hi]indole-5-carboxamide, I-6

To a solution of 6-(2-(naphthalen-1-yloxy)ethyl)-2,3-dihydro-[1,4]oxazino[2,3,4-hi]indole-5-carboxylic acid (14 mg, 0.038 mmol) in dichloromethane (754 μl) at rt was added benzenesulfonamide (6.52 mg, 0.041 mmol), 1-(3-dimethylaminopropyl)-3-ethylcarbodiimide hydrochloride (10.84 mg, 0.057 mmol) and DMAP (9.21 mg, 0.075 mmol). After 15 h at rt, the mixture was diluted with dichloromethane, washed with 1M HCl, dried ($MgSO_4$), filtered and concentrated in vacuo. The residue was purified via reverse-phase preparative HPLC (Phenomenex Gemini C18, $H_2O$/$CH_3CN$ gradient to 50-95% $CH_3CN$ 0.1% TFA) to give the title compound. MS (ES) 513.1 (M+H); 1H NMR (400 MHz, $CDCl_3$): 10.75 (s, 1H), 7.97 (t, J=7.4 Hz, 2H), 7.92 (d, J=8 .Hz, 1H), 7.81 (d, J=8.5 Hz, 1H), 7.59 (t, J=6.5 Hz, 1H), 7.54 (d, J=8.2 Hz, 1H), 7.42 (t, J=8.1 Hz, 2H), 7.33 (m, 2H), 7.23 (d, J=8.2 Hz, 1H), 7.08 (t, J=8.0 Hz, 1H), 6.93 (d, J=7.6 Hz, 1H), 6.80 (d, J=7.6 Hz, 1H), 4.66 (t, J=5.5 Hz, 2H), 4.54 (d, J=5.1 Hz, 2H), 4.48 (d, J=4.9 Hz, 2H), 3.73 (t, J=5.4 Hz, 2H).

Example 7

Preparation of 6-(3-(naphthalen-1-yloxy)propyl)-2,3-dihydro-[1,4]thiazino[2,3,4-hi]indole-5-carboxylic acid, I-7

Step A. Preparation of 6-(3-ethoxy-3-oxopropyl)-2,3-dihydro-[1,4]thiazino[2,3,4-hi]indole-5-carboxylic acid The title compound was prepared according to procedures described in Example 1, Step D, using 2,3-dihydro-4H-benzo[b][1,4]thiazin-4-amine (500 mg, 3.0 mmol) and substituting 2-oxopentanedioic acid with 2-oxohexanedioic acid (722 mg, 4.5 mmol). MS (ES) 320.1 (M+H).

Step B. Preparation of methyl 6-(3-ethoxy-3-oxopropyl)-2,3-dihydro-[1,4]thiazino[2,3,4-hi]indole-5-carboxylate The title compound was prepared according to procedures described in Example 1, Step E, using 6-(3-ethoxy-3-oxopropyl)-2,3-dihydro-[1,4]thiazino[2,3,4-hi]indole-5-carboxylic acid.

Step C. Preparation of methyl 6-(3-hydroxypropyl)-2,3-dihydro-[1,4]thiazino[2,3,4-hi]indole-5-carboxylate The title compound (465 mg, 1.6 mmol) was prepared as a yellow oil according to procedures described in Example 1, Step F, using crude methyl 6-(3-ethoxy-3-oxopropyl)-2,3-dihydro-[1,4]thiazino[2,3,4-hi]indole-5-carboxylate. MS (ES) 292.1 (M+H).

Step D. Example 7

The title compound (25 mg, 0.062 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]thiazino[2,3,4-hi]indole-5-carboxylate (56 mg, 0.2 mmol). MS (ES) 404.1 (M+H); $^1$H NMR (400 MHz, DMSO-$d_6$) δ 8.21-8.15 (m, 1H), 7.90-7.82 (m, 1H), 7.57-7.34 (m, 5H), 7.06 (d, J=7.2 Hz, 1H), 6.97-6.84 (m, 2H), 4.77-4.67 (m, 2H), 4.17 (t, J=6.0 Hz, 2H), 3.32-3.28 (m, 4H), 2.25-2.14 (m, 2H).

Example 8

Preparation of N-(methylsulfonyl)-6-(3-(naphthalen-1-yloxy)propyl)-2,3-dihydro-[1,4]thiazino[2,3,4-hi]indole-5-carboxamide, I-8

The title compound (8.0 mg, 0.017 mmol) was prepared according to procedures described in Example 2 by substituting 6-(2-(naphthalen-1-yloxy)ethyl)-2,3-dihydro-[1,4]thiazino[2,3,4-hi]indole-5-carboxylic acid with 6-(3-(naphthalen-1-yloxy)propyl)-2,3-dihydro-[1,4]thiazino[2,3,4-hi]indole-5-carboxylic acid (12 mg, 0.030 mmol). MS (ES) 481.1 (M+H).

Example 9

Preparation of 6-(3-((5,6,7,8-tetrahydronaphthalen-1-yl)oxy)propyl)-2,3-dihydro-[1,4]thiazino[2,3,4-hi]indole-5-carboxylic acid, I-9

The title compound (38 mg, 0.093 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]thiazino[2,3,4-hi]indole-5-carboxylate (56 mg, 0.2 mmol) and naphthalen-1-ol with 5,6,7,8-tetrahydronaphthalen-1-ol (46 mg, 0.31 mmol). MS (ES) 408.2 (M+H).

Example 10

Preparation of 6-(3-((4-chloronaphthalen-1-yl)oxy)propyl)-2,3-dihydro-[1,4]thiazino[2,3,4-hi]indole-5-carboxylic acid, I-10

The title compound (48 mg, 0.11 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]thiazino[2,3,4-hi]indole-5-carboxylate (56 mg, 0.2 mmol) and naphthalen-1-ol with 4-chloronaphthalen-1-ol (55 mg, 0.31 mmol). MS (ES) 438.1 (M+H).

Example 11

Preparation of 6-(3-((5,6,7,8-tetrahydronaphthalen-2-yl)oxy)propyl)-2,3-dihydro-[1,4]thiazino[2,3,4-hi]indole-5-carboxylic acid, I-11

The title compound (23 mg, 0.056 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]thiazino[2,3,4-hi]indole-5-carboxylate (56 mg, 0.2 mmol) and naphthalen-1-ol with 5,6,7,8-tetrahydronaphthalen-2-ol (46 mg, 0.31 mmol). MS (ES) 408.1 (M+H).

Example 12

Preparation of 6-(3-(4-chloro-3-methylphenoxy)propyl)-2,3-dihydro-[1,4]thiazino[2,3,4-hi]indole-5-carboxylic acid, I-12

The title compound (42 mg, 0.10 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]thiazino[2,3,4-hi]indole-5-carboxylate (56 mg, 0.2 mmol) and naphthalen-1-ol with 4-chloro-3-methylphenol (45 mg, 0.31 mmol). MS (ES) 402.1 (M+H).

Example 13

Preparation of 6-(3-(4-chloro-3,5-dimethylphenoxy)propyl)-2,3-dihydro-[1,4]thiazino[2,3,4-hi]indole-5-carboxylic acid, I-13

The title compound (24 mg, 0.058 mmol) was prepared as a white solid according to procedures described in Example 1, Step E, substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]thiazino[2,3,4-hi]indole-5-carboxylate (56 mg, 0.2 mmol) and naphthalen-1-ol with 4-chloro-3,5-dimethylphenol (46 mg, 0.31 mmol). MS (ES) 416.1 (M+H).

Example 14

Preparation of 1-(3-(naphthalen-1-yloxy)propyl)-5,6-dihydro-4H-pyrrolo[3,2,1-ij]quinoline-2-carboxylic acid, I-14

Step A. Preparation of 1-(3-ethoxy-3-oxopropyl)-5,6-dihydro-4H-pyrrolo[3,2,1-ij]quinoline-2-carboxylic acid The title compound was prepared according to procedures described in Example 1, Step D, using 3,4-dihydroquinolin-1(2H)-amine (74 mg, 0.5 mmol) and substituting 2-oxopentanedioic acid with 2-oxohexanedioic acid (160 mg, 1.0 mmol). MS (ES) 302.1 (M+H).

Step B. Preparation of methyl 1-(3-ethoxy-3-oxopropyl)-5,6-dihydro-4H-pyrrolo[3,2,1-ij]quinoline-2-carboxylate The title compound was prepared according to procedures described in Example 1, Step E, using 1-(3-ethoxy-3-oxopropyl)-5,6-dihydro-4H-pyrrolo[3,2,1-ij]quinoline-2-carboxylic acid.

Step C. Preparation of methyl 1-(3-hydroxypropyl)-5,6-dihydro-4H-pyrrolo[3,2,1-ij]quinoline-2-carboxylate The title compound (72 mg, 0.26 mmol) was prepared as a yellow oil according to procedures described in Example 1, Step F, using crude methyl 1-(3-ethoxy-3-oxopropyl)-5,6-dihydro-4H-pyrrolo[3,2,1-ij]quinoline-2-carboxylate. MS (ES) 274.1 (M+H).

Step D. Example 14

The title compound (20 mg, 0.052 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 1-(3-hydroxypropyl)-5,6-dihydro-4H-pyrrolo[3,2,1-ij]quinoline-2-carboxylate (56 mg, 0.2 mmol). MS (ES) 386.2 (M+H); $^1$H NMR (400 MHz, DMSO-$d_6$) δ 8.24-8.17 (m, 1H), 7.89-7.85 (m, 1H), 7.56-7.41 (m, 4H), 7.38 (t, J=7.9 Hz, 1H), 6.97 (d, J=6.9 Hz, 1H), 6.91-6.84 (m, 2H), 4.48-4.40 (m, 2H), 4.16 (t, J=6.1 Hz, 2H), 3.32-3.30 (m, 2H), 2.91 (t, J=6.1 Hz, 2H), 2.25-2.06 (m, 4H).

Example 15

Preparation of N-(methylsulfonyl)-1-(3-(naphthalen-1-yloxy)propyl)-5,6-dihydro-4H-pyrrolo[3,2,1-ij]quinoline-2-carboxamide, I-15

The title compound (2.0 mg, 0.0043 mmol) was prepared according to procedures described in Example 2 by substituting 6-(2-(naphthalen-1-yloxy)ethyl)-2,3-dihydro-[1,4]thiazino[2,3,4-hi]indole-5-carboxylic acid with 1-(3-(naphthalen-1-yloxy)propyl)-5,6-dihydro-4H-pyrrolo[3,2,1-ij]quinoline-2-carboxylic acid (11 mg, 0.030 mmol). MS (ES) 481.1 (M+H).

Example 16

Preparation of 1-(3-(4-chloro-3,5-dimethylphenoxy)propyl)-5,6-dihydro-4H-pyrrolo[3,2,1-ij]quinoline-2-carboxylic acid, I-16

The title compound (36 mg, 0.090 mmol) was prepared as a white solid according to procedures described in Example 1, Step E, by substituting methyl 6-(2-hydroxyethyl)-2,3-dihydro-[1,4]thiazino[2,3,4-hi]indole-5-carboxylate with methyl 1-(3-hydroxypropyl)-5,6-dihydro-4H-pyrrolo[3,2,1-ij]quinoline-2-carboxylate (55 mg, 0.2 mmol) and naphthalen-1-ol with 4-chloro-3,5-dimethylphenol (46 mg, 0.31 mmol). MS (ES) 398.2 (M+H).

Example 17

Preparation of 1-(3-(4-chloro-3,5-dimethylphenoxy)propyl)-N-(phenylsulfonyl)-5,6-dihydro-4H-pyrrolo[3,2,1-ij]quinoline-2-carboxamide, I-17

The title compound was prepared (12 mg, 0.022 mmol) as a white solid according to procedures described in Example 6 by substituting 6-(2-(naphthalen-1-yloxy)ethyl)-2,3-dihydro-[1,4]oxazino[2,3,4-hi]indole-5-carboxylic acid with 1-(3-(4-chloro-3,5-dimethylphenoxy)propyl)-5,6-dihydro-4H-pyrrolo[3,2,1-ij]quinoline-2-carboxylic acid (15 mg, 0.038 mmol). MS (ES) 537.1 (M+H). $^1$H NMR (400 MHz, CDCl$_3$): 9.77 (s, 1H), 7.95 (d, J=8.2 Hz, 1H), 7.62 (t, J=7.4 Hz, 2H), 7.48 (t, J=7.9 Hz, 4H), 7.07 (m, 2H), 6.83 (s, 2H), 4.30 (t, J=5.0 Hz, 2H), 3.86 (t, J=5.8 Hz, 2H), 3.39 (t, J=6.6 Hz, 2H), 2.95 (t, J=6.0 Hz, 2H), 2.35 (m, 8H), 2.16 (m, 2H).

Example 18

Preparation of 7-(3-(naphthalen-1-yloxy)propyl)-3,4-dihydro-2H-[1,4]thiazepino[2,3,4-hi]indole-6-carboxylic acid, I-18

Step A. Preparation of 5-nitroso-2,3,4,5-tetrahydrobenzo[b][1,4]thiazepine

The title compound (425 mg, 2.2 mmol) was prepared as a yellow oil according to procedures described in Example 1, Step B, by substituting 3,4-dihydro-2H-benzo[b][1,4]thiazine with 2,3,4,5-tetrahydrobenzo[b][1,4]thiazepine (495 mg, 3.0 mmol). MS (ES) 195.1 (M+H).

Step B. Preparation of 3,4-dihydrobenzo[b][1,4]thiazepin-5(2H)-amine

The title compound (261 mg, 1.45 mmol) was prepared as a light yellow oil according to procedures described in Example 1, Step C, using 5-nitroso-2,3,4,5-tetrahydrobenzo[b][1,4]thiazepine (425 mg, 2.2 mmol). MS (ES) 181.1 (M+H).

Step C. Preparation of 7-(3-ethoxy-3-oxopropyl)-3,4-dihydro-2H-[1,4]thiazepino[2,3,4-hi]indole-6-carboxylic acid The title compound was prepared as an off-white solid according to procedures described in Example 1, Step D, using 3,4-dihydrobenzo[b][1,4]thiazepin-5(2H)-amine (261 mg, 1.45 mmol) and substituting 2-oxopentanedioic acid with 2-oxohexanedioic acid (301 mg, 1.88 mmol). MS (ES) 334.1 (M+H).

Step D. Preparation of methyl 7-(3-ethoxy-3-oxopropyl)-3,4-dihydro-2H-[1,4]thiazepino[2,3,4-hi]indole-6-carboxylate The title compound was prepared according to procedures described in Example 1, Step E, using 7-(3-ethoxy-3-oxopropyl)-3,4-dihydro-2H-[1,4]thiazepino[2,3,4-hi]indole-6-carboxylic acid. It was used in the subsequent reaction without further purification.

Step E. Preparation of 7-(3-hydroxypropyl)-3,4-dihydro-2H-[1,4]thiazepino[2,3,4-hi]indole-6-carboxylic acid The title compound (211 mg, 0.72 mmol) was prepared as a light yellow oil according to procedures described in Example 1, Step F, using crude methyl 7-(3-ethoxy-3-oxopropyl)-3,4-dihydro-2H-[1,4]thiazepino[2,3,4-hi]indole-6-carboxylate (1.45 mmol). MS (ES) 292.1 (M+H).

Step F. Example 18

The title compound (49 mg, 0.12 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 7-(3-hydroxypropyl)-3,4-dihydro-2H-[1,4]thiazepino[2,3,4-hi]indole-6-carboxylic acid (50 mg, 0.16 mmol). MS (ES) 418.1 (M+H); $^1$H NMR (400 MHz, DMSO-$d_6$) δ 8.21-8.15 (m, 1H), 7.88-7.83 (m, 1H), 7.55-7.42 (m, 4H), 7.38 (t, J=7.9 Hz, 1H), 7.12 (d, J=7.2 Hz, 1H), 6.91-6.82 (m, 2H), 4.86 (dd, J=6.9, 4.6 Hz, 2H), 4.21-4.14 (m, 2H), 3.36-3.33 (m, 2H), 3.24 (dd, J=8.4, 6.5 Hz, 2H), 2.32-2.11 (m, 4H).

Example 19

Preparation of N-(methylsulfonyl)-7-(3-(naphthalen-1-yloxy)propyl)-3,4-dihydro-2H-[1,4]thiazepino[2,3,4-hi]indole-6-carboxamide, I-19

The title compound (4.0 mg, 0.0081 mmol) was prepared according to procedures described in Example 2 by substituting 6-(2-(naphthalen-1-yloxy)ethyl)-2,3-dihydro-[1,4]thiazino[2,3,4-hi]indole-5-carboxylic acid with 7-(3-(naphthalen-1-yloxy)propyl)-3,4-dihydro-2H-[1,4]thiazepino[2,3,4-hi]indole-6-carboxylic acid (13 mg, 0.030 mmol). MS (ES) 495.1 (M+H).

Example 20

Preparation of 7-(3-(naphthalen-1-yloxy)propyl)-3,4-dihydro-2H-[1,4]thiazepino[2,3,4-hi]indole-6-carboxylic acid 1-oxide, I-20

To a solution of 7-(3-(naphthalen-1-yloxy)propyl)-3,4-dihydro-2H-[1,4]thiazepino[2,3,4-hi]indole-6-carboxylic acid (18 mg, 0.043 mmol) in $CH_2Cl_2$ (1.0 mL) and THF (1.0 mL) was added mCPBA (10 mg (77% pure), 0.43 mmol) at rt. The reaction was monitored by LCMS and showed that all starting sulfide was converted to 1:1 mixture of sulfoxide and sulfone oxidation states after 1 h. The reaction was quenched by addition of $H_2O$, extracted with $CH_2Cl_2$ and concentrated in vacuo. The residue was purified by reverse-phase preparative HPLC (Phenomenex Gemini C18, $H_2O$/$CH_3CN$ gradient to 25-95% $CH_3CN$ 0.1% TFA) to give the title compound (6.0 mg, 0.014 mmol) as an off-white solid. MS (ES) 434.1 (M+H).

Example 21

Preparation of 7-(3-(naphthalen-1-yloxy)propyl)-3,4-dihydro-2H-[1,4]thiazepino[2,3,4-hi]indole-6-carboxylic acid 1,1-dioxide, I-21

The title compound (7.0 mg, 0.016 mmol) was prepared as a white solid along with Example 20 according to procedures described in Example 20. MS (ES) 450.1 (M+H).

Example 22

Preparation of 6-(3-(naphthalen-1-yloxy)propyl)-2,3-dihydro-[1,4]thiazino[2,3,4-hi]indole-5-carboxylic acid 1,1-dioxide, I-22

To a solution of 6-(3-(naphthalen-1-yloxy)propyl)-2,3-dihydro-[1,4]thiazino[2,3,4-hi]indole-5-carboxylic acid (20 mg, 0.05 mmol) in $CH_2Cl_2$ (1.0 mL) and THF (1.0 mL) was added mCPBA (17 mg (77% pure), 0.99 mmol) at rt. The reaction mixture was stirred for 1 h at rt then quenched by addition of $H_2O$, extracted with $CH_2Cl_2$ and concentrated in vacuo. The residue was purified by reverse-phase preparative HPLC (Phenomenex Gemini C18, $H_2O$/$CH_3CN$ gradient to 25-95% $CH_3CN$ 0.1% TFA) to give the title compound (12 mg, 0.028 mmol) as a white solid. MS (ES) 436.1 (M+H).

Example 23

Preparation of 7-(3-(4-chloro-3,5-dimethylphenoxy)propyl)-3,4-dihydro-2H-[1,4]thiazepino[2,3,4-hi]indole-6-carboxylic acid, I-23

The title compound (54 mg, 0.13 mmol) was prepared as a white solid according to procedures described in Example 1, Step E, by substituting methyl 6-(2-hydroxyethyl)-2,3-dihydro-[1,4]thiazino[2,3,4-hi]indole-5-carboxylate with methyl 7-(3-hydroxypropyl)-3,4-dihydro-2H-[1,4]thiazepino[2,3,4-hi]indole-6-carboxylic acid (50 mg, 0.16 mmol) and naphthalen-1-ol with 4-chloro-3,5-dimethylphenol (39 mg, 0.25 mmol). MS (ES) 430.1 (M+H); $^1$H NMR (400 MHz, DMSO-$d_6$) δ 7.46 (d, J=8.0 Hz, 1H), 7.13 (d, J=7.2 Hz, 1H), 6.91 (t, J=7.6 Hz, 1H), 6.75 (s, 2H), 4.90-4.81 (m, 2H), 3.94 (t, J=6.3 Hz, 2H), 3.39-3.34 (m, 2H), 3.13-3.07 (m, 2H), 2.34-2.22 (m, 8H), 2.04-1.95 (m, 2H).

Example 24

Preparation of 7-(3-(4-chloro-3,5-dimethylphenoxy)propyl)-N-(phenylsulfonyl)-3,4-dihydro-2H-[1,4]thiazepino[2,3,4-hi]indole-6-carboxamide, I-24

The title compound was prepared (9 mg, 0.016 mmol) as an off-white solid according to procedures described in Example 6 by substituting 6-(2-(naphthalen-1-yloxy)ethyl)-2,3-dihydro-[1,4]oxazino[2,3,4-hi]indole-5-carboxylic acid with 7-(3-(4-chloro-3,5-dimethylphenoxy)propyl)-3,4-dihydro-2H-[1,4]thiazepino[2,3,4-hi]indole-6-carboxylic acid (12 mg, 0.028 mmol). MS (ES) 569.1 (M+H). $^1$H NMR (400 MHz, $CDCl_3$): 9.84 (s, 1H), 7.95 (d, J=7.5 Hz, 2H), 7.63 (t, J=7.5 Hz, 1H), 7.51 (t, J=8.0 Hz, 2H), 7.39 (d, J=8.0 Hz, 1H), 7.23 (d, J=7.3 Hz, 1H), 6.99 (t, J=7.8 Hz, 1H), 6.77 (s, 2H), 4.61 (t, J=5.3 Hz, 2H), 3.89 (t, J=5.3 Hz, 2H), 3.35 (t, J=6.9 Hz, 2H), 3.27 (t, J=6.9 Hz, 2H), 2.34 (m, 10H).

Example 25

Preparation of 6-(3-(naphthalen-1-yloxy)propyl)-2,3-dihydro-[1,4]oxazino[2,3,4-hi]indole-5-carboxylic acid, I-25

Step A. Preparation of 6-(3-ethoxy-3-oxopropyl)-2,3-dihydro-[1,4]oxazino[2,3,4-hi]indole-5-carboxylic acid The title compound was prepared according to procedures described in Example 1, Step D, using 2,3-dihydro-4H- benzo[b][1,4]oxazin-4-amine (430 mg, 2.9 mmol) and substituting 2-oxopentanedioic acid with 2-oxohexanedioic acid (595 mg, 3.7 mmol). MS (ES) 304.1 (M+H).

Step B. Preparation of methyl 6-(3-ethoxy-3-oxopropyl)-2,3-dihydro-[1,4]oxazino[2,3,4-hi]indole-5-carboxylate To a solution of 6-(3-ethoxy-3-oxopropyl)-2,3-dihydro-[1,4]oxazino[2,3,4-hi]indole-5-carboxylic acid (2.9 mmol) in acetone (10 mL) was added $K_2CO_3$ (301 mg, 5.8 mmol) at rt. The reaction mixture was stirred for 10 min then MeI (1.8 mL, 29 mmol) was added at rt. The reaction mixture was stirred for 24 h at rt then filtered. The filtrate was concentrated in vacuo, and the residue was purified by flash chromatography (Combi-flash Rf Hexane/EtOAc gradient 0-100%) to give the title compound (465 mg, 1.5 mmol) as a colorless oil. MS (ES) 318.1 (M+H).

Step C. Preparation of methyl 6-(3-hydroxypropyl)-2,3-dihydro-[1,4]oxazino[2,3,4-hi]indole-5-carboxylate The title compound (375 mg, 1.4 mmol) was prepared as a light yellow oil according to procedures described in Example 1, Step F, using methyl 6-(3-ethoxy-3-oxopropyl)-2,3-dihydro-[1,4]oxazino[2,3,4-hi]indole-5-carboxylate (465 mg, 1.5 mmol). MS (ES) 276.1 (M+H).

Step D. Example 25

The title compound (55 mg, 0.15 mmol) was prepared as an off-white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]oxazino[2,3,4-hi]indole-5-carboxylate (75 mg, 0.27 mmol). MS (ES) 388.1 (M+H).

Example 26

Preparation of 6-(3-(4-chloro-3,5-dimethylphenoxy)propyl)-2,3-dihydro-[1,4]oxazino[2,3,4-hi]indole-5-carboxylic acid, I-26

The title compound (64 mg, 0.16 mmol) was prepared as a white solid according to procedures described in Example 1, Step E, by substituting methyl 6-(2-hydroxyethyl)-2,3-dihydro-[1,4]thiazino[2,3,4-hi]indole-5-carboxylate with methyl 6-(3-hydroxypropyl)-2,3-dihydro-[1,4]oxazino[2,3,4-hi]indole-5-carboxylate (75 mg, 0.27 mmol) and naphthalen-1-ol with 4-chloro-3,5-dimethylphenol (68 mg, 0.43 mmol). MS (ES) 400.1 (M+H).

Example 27

Preparation of 9-chloro-6-(3-(4-chloro-3,5-dimethylphenoxy)propyl)-2,3-dihydro-[1,4]oxazino[2,3,4-hi]indole-5-carboxylic acid, I-27

Step A. Preparation of 5-(2-(2-bromo-3-chlorophenyl)hydrazono)-6-ethoxy-6-oxohexanoic acid To a stirring mixture of 2-bromo-3-chloroaniline (4.1 g, 20 mmol) in 1M HCl (25 mL) and water (5 mL) at 0° C. was added $NaNO_2$ (1.38 g, 20 mmol) in water (20 mL), $NaCH_3COOH$ (9.23 g, 112 mmol) in water (25 mL) and ethyl 2-oxocyclopentane carboxylate (3.0 mL, 20 mmol) in sequence. The reaction mixture was stirred for 15 min at 0° C. then warmed to 20° C. over 2 h and extracted with $CH_2Cl_2$, dried over $MgSO_4$, filtered and concentrated in vacuo to give the title compound as a red oil in 7.0 g (90% crude).

Step B. Preparation of ethyl 7-bromo-6-chloro-3-(3-ethoxy-3-oxopropyl)-1H-indole-2-carboxylate To a solution of 5-(2-(2-bromo-3-chlorophenyl)hydrazono)-6-ethoxy-6-oxohexanoic acid (7.0 g, 18 mmol) in EtOH (30 mL) was added conc. $H_2SO_4$ (7.5 mL), slowly. The reaction mixture was refluxed for 1.5 h. The reaction was quenched by pouring into ice then extracted with $CH_2Cl_2$. The combined organic layer was washed with sat. $NaHCO_3$, water, brine, dried over $MgSO_4$, filtered and concentrated in vacuo. The residue was purified by flash chromatography (Combi-flash Rf Hex/EtOAc 0-25% gradient) to give the title compound (4.8 g, 12 mmol) as an off-white solid. MS (ES) 402.0 (M+H).

Step C. Preparation ethyl 7-bromo-6-chloro-3-(3-hydroxypropyl)-1H-indole-2-carboxylate To a solution of ethyl 7-bromo-6-chloro-3-(3-ethoxy-3-oxopropyl)-1H-indole-2-carboxylate (2.0 g, 4.8 mmol) in THF (20 mmol) was added $BH_3$ in THF (20 mL, 20 mmol) at 20° C. The reaction mixture was stirred for 15 h at 20° C. and quenched by addition of MeOH then concentrated in vacuo. The residue was purified by flash chromatography (Combi-flash Rf Hexane/EtOAc gradient 0-50%) to give the title compound (1.44 g, 4.0 mmol) as a white solid. MS (ES) 360.0 (M+H).

Step D. Preparation of ethyl 7-bromo-6-chloro-3-(3-(4-chloro-3,5-dimethylphenoxy)propyl)-1H-indole-2-carboxylate To a solution of ethyl 7-bromo-6-chloro-3-(3-hydroxypropyl)-1H-indole-2-carboxylate (1.0 g, 0.28 mmol), $PPh_3$ (1.1 g, 5.1 mmol) and 3,5-diMe-4-Cl-phenol (810 g, 5.2 mmol) in THF (35 mL) was added Dt-BuAD (990 mg, 5.1 mmol) at 20° C. The reaction mixture was stirred for 15 h at 20° C. then concentrated in vacuo. The residue was purified by flash chromatography (Combi-flash Rf Hexane/EtOAc gradient 0-10%) to give the title compound (1.15 g, 2.3 mmol) as a white solid. MS (ES) 498.0 (M+H).

Step E. Preparation of ethyl 6-chloro-3-(3-(4-chloro-3,5-dimethylphenoxy)propyl)-7-(4,4,5,5-tetramethyl-1,3,2-dioxaborolan-2-yl)-1H-indole-2-carboxylate A mixture of ethyl 7-bromo-6-chloro-3-(3-(4-chloro-3,5-dimethylphenoxy)propyl)-1H-indole-2-carboxylate (250 mg, 0.50 mmol), bis(pinacolato)diboron (153 mg, 0.60 mmol), potassium acetate (226 mg, 2.3 mmol) and 1,1'-bis(diphenylphosphino)ferrocenedichloro palladium(ii) dichloromethane complex (18.32 mg, 0.025 mmol) in DMF (2.5 mL) was stirred at 90° C. for 20 h then cooled to rt. The reaction mixture was diluted with $Et_2O$ (100 mL). The combined organics were washed with $H_2O$ (4×10 mL), sat NaCl (10 mL), dried ($MgSO_4$), filtered and concentrated in vacuo. The residue was purified by flash chromatography (Combi-flash Rf Hexane/EtOAc gradient 0-15%) to give the title compound (1.15 g, 2.3 mmol) as a white solid. MS (ES) 546.0 (M+H).

Step F. Preparation of ethyl 6-chloro-3-(3-(4-chloro-3,5-dimethylphenoxy)propyl)-7-hydroxy-1H-indole-2-carboxylate To a solution of ethyl 6-chloro-3-(3-(4-chloro-3,5-dimethylphenoxy)propyl)-7-(4,4,5,5-tetramethyl-1,3,2-dioxaborolan-2-yl)-1H-indole-2-carboxylate (63 mg, 0.12 mmol) and sodium hydroxide (1.2 mL, 0.58 mmol) in THF (1.2 mL) at rt was added hydrogen peroxide (118 µL, 1.2 mmol). After 15 h at rt, the mixture was quenched with sat NH$_4$Cl/NH$_4$OH buffer solution. The mixture was extracted with EtOAc, dried (MgSO$_4$), filtered and concentrated in vacuo. The residue was purified via reverse-phase preparative HPLC (Phenomenex Gemini C18, H$_2$O/CH$_3$CN gradient to 5-65% CH$_3$CN 0.1% TFA) to give the title compound (15 mg, 0.034). MS (ES) 436.0 (M+H).

Step G. Example 27

A mixture of ethyl 6-chloro-3-(3-(4-chloro-3,5-dimethylphenoxy)propyl)-7-hydroxy-1H-indole-2-carboxylate (10 mg, 0.023 mmol), cesium carbonate (37 mg, 0.12 mmol) and dibromoethane (4.0 µL, 0.046 mmol) in DMF (458 µL) was stirred at 100° C. for 15 h. The mixture was cooled to rt and filtered through a hydrophobic frit and concentrated in vacuo. The residue was dissolved in THF (230 µL) and 2N aq. lithium hydroxide (115 µL, 0.23 mmol) was added. The reaction mixture was stirred at rt for 15 h, the mixture was acidified with TFA and concentrated in vacuo. The residue was purified via reverse-phase preparative HPLC (Phenomenex Gemini C18, H$_2$O/CH$_3$CN gradient to 50-95% CH$_3$CN 0.1% TFA) to give the title compound (7.5 mg, 0.017 mmol) as a white solid. MS (ES)=434.0 (M+H); $^1$H NMR (400 MHz, d$^6$-DMSO): 7.23 (d, J=8.6 Hz, 1H), 6.98 (d, J=8.6 Hz, 1H), 6.71 (s, 2H), 4.57 (m, 4H), 3.93 (t, J=6.2 Hz, 2H), 3.31 (s, 3H), 3.15 (t, J=7.6 Hz, 2H), 2.25 (s, 6H), 2.00 (t, J=7.1 Hz, 2H).

Example 28

Preparation of 7-chloro-1-(3-(4-chloro-3,5-dimethylphenoxy)propyl)-5,6-dihydro-4H-pyrrolo[3,2,1-ij]quinoline-2-carboxylic acid, I-28

Step A. Preparation of ethyl 1-allyl-7-bromo-6-chloro-3-(3-(4-chloro-3,5-dimethylphenoxy)propyl)-1H-indole-2-carboxylate A solution of ethyl 7-bromo-6-chloro-3-(3-(4-chloro-3,5-dimethylphenoxy)propyl)-1H-indole-2-carboxylate (100 mg, 0.20 mmol), 3-bromoprop-1-ene (0.026 mL, 0.30 mmol), Cs$_2$CO$_3$ (196 mg, 0.60 mmol) in DMF (1.5 mL) was stirred at 80 C.° for 3 h. The reaction mixture was concentrated and the residue was purified by flash chromatography (Combi-flash Rf Hexane/EtOAc gradient 0-70%) to give the title compound (105 mg 0.19 mmol) as a yellow oil. MS (ES) 538.1 (M+H).

Step B. Example 28

A solution of ethyl 1-allyl-7-bromo-6-chloro-3-(3-(4-chloro-3,5-dimethylphenoxy)propyl)-1H-indole-2-carboxylate (105 mg, 0.19 mmol), AIBN (1.6 mg, 9.7 gmol), Bu$_3$SnH (0.105 ml, 0.39 mmol) in toluene (1.0 mL) was stirred at 100° C. for 90 min. The reaction mixture was concentrated, and the residue was dissolved in THF (1 mL) and LiOH (0.5 mL, 2N) and stirred at 40° C. for 24 h. The reaction mixture was concentrated, and the residue was purified by reverse-phase preparative HPLC (Phenomenex Gemini C18, H$_2$O/CH$_3$CN gradient to 60-95% CH$_3$CN 0.1% TFA) to give the title compound (41 mg, 0.095 mmol) as a white solid. MS (ES) 432.1 (M+H).

Example 29

Assays for Bcl-2 Family Proteins Activity

The in vitro modulation of Bcl-2 family proteins was determined as follows.
Bak Peptide Binding Assay
General Provided compounds of the present invention can be demonstrated to compete for binding with fluorescently labeled peptides derived from relevant BH3 domains. In some embodiments, a provided compound exhibit selectivity for Mcl-1 over Bcl-xL and Bcl-2.
Assay Compound affinity was measured using a fluorescence polarization anisotropy competition assay. Anisotropy measurements were carried out in 384-well, black, flat-bottom plates (Greiner Bio-one, Monroe, N.C., USA). The assay was run using a fluorescein isothiocyanate-labeled BH3 peptide derived from Bak (FITC-AHx-GQVGRQLAI IGD-DINRN H$_2$) (SEQ ID NO: 1) that was purchased from GenScript (Piscataway, N.J.) at >95% purity and used without further purification. 10 nM FITC-Bak peptide and 14 nM recombinant Mcl-1 (residues 172-327) were added to assay buffer (3 mM dithiothreitol, 50 mM NaCl, 20 mM Tris, pH 7.5). For selectivity assays, 40 nM Bcl-2 (residues 1-207$^{A96T,G110R}$, Δ35-91, replaced with Bcl-xL$_{35-50}$) or 4 nM Bcl-xL (residues 1-209, loop 45-86 deleted) were incubated with 10 nM FITC-Bak in assay buffer.

Compounds are diluted in DMSO in a 10-point, 3-fold serial dilution scheme. 2.5 uL compound is added to 47.5 uL of assay buffer containing FITC-Bak and protein, for a final DMSO concentration of 5% and a top concentration of 20 uM. A FITC-Bak peptide alone (100% inhibition) and peptide plus protein (0% inhibition) control is included on each assay plate. The plate was mixed and incubated for 90 minutes at room temperature. Anisotropy is measured at excitation wavelength 480 nm and emission wavelength 535 nm using an EnVision Multi-label plate reader (PerkinElmer, Wellesley, Mass., USA). Fluorescence anisotropy is plotted against compound concentration to generate an IC$_{50}$ (inhibitor concentration at which 50% of bound peptide is displaced) by fitting the data to a 4-parameter logistic model using XLFit software (Guildford, Surrey, UK). IC$_{50}$ is converted to a binding dissociation constant (Ki value) according to the formula of Wang Z. FEBS Lett (1996) 3, 245:

$$K_i = [I]_{50}/([L]_{50}/K_d + [P]_0/K_d + 1)$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, K$_d$ represents the dissociation constant of the FITC peptide probe. The results for representative compounds are shown in Tables 2 and 3, below.

These data demonstrate the utility of representative compounds having general formula I as inhibitors of the activity of Mcl-1 and Bcl-xL proteins to bind peptides from relevant BH3 domains.

TABLE 2

Ki For Representative Compounds Having General Formula I For Inhibition of Mcl-I Protein

| Examples | $K_i$ |
|---|---|
| 1, 2, 3, 4, 5, 8, 15 | 1 μM-9.99 μM |
| 6, 19 | 501 nM-999 nM |
| 11, 14, 17, | 301 nM-500 nM |

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Synthetic

<400> SEQUENCE: 1

```
Gly Gln Val Gly Arg Gln Leu Ala Ile Ile Gly Asp Asp Ile Asn Arg
1               5                   10                  15
```

TABLE 2-continued

Ki For Representative Compounds Having General Formula I For Inhibition of Mcl-I Protein

| Examples | $K_i$ |
|---|---|
| 7, 9, 10, 12, 16, 18, 24, 25 | 101 nM-299 nM |
| 13, 20, 21, 22, 23, 26, 27, 28 | ≤100 nM |

TABLE 3

$K_i$ (μM) For Representative Compounds Having General Formula I For Inhibitory selectivity of Mcl-I Protein over Bcl-xL protein.

| Example | Mcl-1 | Bcl-xL |
|---|---|---|
| 7 | 0.107 | >20 |
| 10 | 0.201 | 4.7 |
| 13 | 0.071 | >20 |
| 20 | 0074 | >20 |
| 23 | 0.040 | >20 |
| 27 | 0.009 | >20 |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The invention claimed is:

1. A compound of formula I:

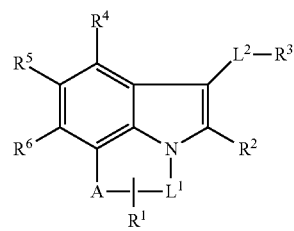

I or a pharmaceutically acceptable salt thereof, wherein:

$L^1$ is selected from a covalent bond or an optionally substituted bivalent straight or branched $C_{1-6}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

A is —O—, —S—, —S(O)—, —S(O)$_2$—, —N(R')—, or optionally substituted —CH$_2$—;

$R^1$ is hydrogen, —R, —OR, —SR, —S(O)R, —S(O)$_2$R, —S(O)$_2$N(R)$_2$, —N(R)$_2$, —C(O)N(R)$_2$, —C(O)R, —C(O)OR, —NRC(O)R, —NRC(O)OR, —NRC(O)N(R)$_2$, —NRS(O)$_2$R, —NRS(O)$_2$N(R)$_2$, —C(O)OH, —C(O)R$^x$, —S(O)$_2$OH, or —S(O)$_2$R$^y$, or is selected from

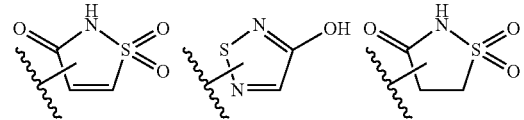

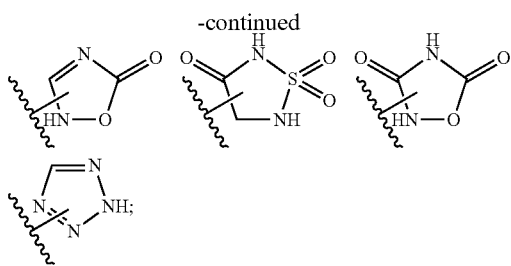

$R^2$ is selected from —C(O)N(R)-L$^3$-R$^z$ and —C(O)O-L-R$^z$;

L$^3$ is selected from a covalent bond and an optionally substituted bivalent straight or branched C$_{1-8}$ hydrocarbon chain wherein one or more methylene units are optionally and independently replaced with -Cy-, —O—, —S—, —N(R)—, —N(R)C(O)—, —N(R)S(O)$_2$—, —C(O)—, —C(O)N(R)—, —S(O)—, —S(O)$_2$—, or —S(O)$_2$N(R)—;

-Cy- is an optionally substituted bivalent ring independently selected from phenylene, 3-8 membered saturated or partially unsaturated carbocyclylene, 5-6 membered heteroarylene having 1-4 heteroatoms independently selected from nitrogen, oxygen, or sulfur, or 3-8 membered saturated or partially unsaturated heterocyclylene having 1-4 heteroatoms independently selected from nitrogen, oxygen, or sulfur;

R$^z$ is hydrogen, R, —OR, —SR, —S(O)R, —S(O)$_2$R, —S(O)$_2$N(R)$_2$, —N(R)$_2$, —C(O)N(R)$_2$, —C(O)R, —C(O)OR, —N(R)C(O)R, —N(R)C(O)OR, —N(R)C(O)N(R)$_2$, —N(R)S(O)$_2$R, —N(R)S(O)$_2$N(R)$_2$, —C(O)OH, —C(O)R$^x$, —S(O)$_2$OH, or —S(O)$_2$R$^3$, or is selected from:

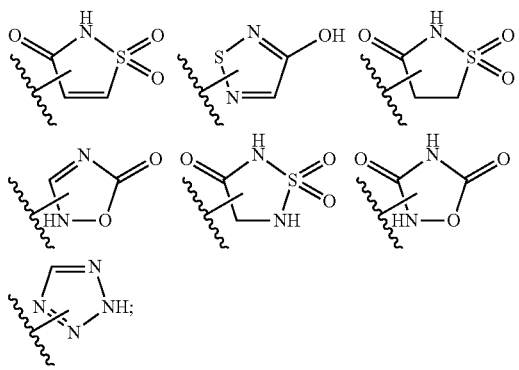

R$^x$ is selected from —C(O)OR, —N(R)S(O)$_2$CF$_3$, —N(R)C(O)R, —N(R)C(O)OR, —N(R)C(O)N(R)$_2$, and —N(R)S(O)$_2$R;

R$^y$ is selected from —N(R)C(O)CF$_3$, —N(R)C(O)R, and —N(R)C(O)N(R)$_2$;

each R is independently selected from hydrogen or an optionally substituted group selected from C$_{1-12}$ aliphatic or a ring selected from a 3-10 membered saturated or partially unsaturated carbocyclic ring, phenyl, a 6-10 membered bicyclic saturated, partially unsaturated or aryl ring, a 3-8 membered saturated or partially unsaturated heterocyclic ring having 1-2 heteroatoms independently selected from nitrogen, oxygen, and sulfur, a 5-6 membered heteroaryl ring having 1-4 heteroatoms independently selected from nitrogen, oxygen, and sulfur, a 7-10 membered bicyclic saturated or partially unsaturated heterocyclic ring having 1-5 heteroatoms independently selected from nitrogen, oxygen and sulfur, and an 8-10 membered bicyclic heteroaryl ring having 1-5 heteroatoms independently selected from nitrogen, oxygen and sulfur;

L$^2$ is an optionally substituted bivalent straight or branched C$_{3-6}$ hydrocarbon chain wherein one or two methylene units of L$^2$ are optionally and independently replaced with —O—, —S—, or —N(R')—, and wherein two substituents of L$^2$ are optionally taken together to form an optionally substituted bivalent ring selected from 3-8 membered saturated or partially unsaturated carbocyclylene and 3-8 membered saturated or partially unsaturated heterocyclylene having 1-4 heteroatoms independently selected from nitrogen, oxygen, and sulfur;

each R' is independently hydrogen or optionally substituted C$_{1-4}$ alkyl;

R$^3$ is an optionally substituted ring selected from a 3-8 membered saturated or partially unsaturated monocyclic carbocyclic ring, phenyl, an 8-10 membered bicyclic aromatic carbocyclic ring, a 3-8 membered saturated or partially unsaturated monocyclic heterocyclic ring having 1-2 heteroatoms independently selected from nitrogen, oxygen, and sulfur, a 5-6 membered monocyclic heteroaromatic ring having 1-4 heteroatoms independently selected from nitrogen, oxygen, and sulfur, and an 8-10 membered bicyclic heteroaromatic ring having 1-5 heteroatoms independently selected from nitrogen, oxygen, and sulfur;

each of R$^4$, R$^5$, and R$^6$ is independently selected from R, halogen, —CN, —NO$_2$, —CF$_3$, —C(O)OR', —OR', —SR', —C(O)N(R')$_2$—N(R')$_2$, —S(O)$_2$N(R)$_2$, —N(R')S(O)$_2$CF$_3$, —C(O)R', —N(R')C(O)R', —S(O)R', —S(O)$_2$R', —N(R')C(O)OR', and —N(R')S(O)$_2$R'; and optionally R$^4$ and R$^5$, R$^5$ and R$^6$ and/or R$^6$ and -A-L$^1$- are independently taken together with their intervening atoms to form an optionally substituted ring selected from a 4-8 membered saturated or partially unsaturated carbocyclic ring, phenyl, a 4-8 membered saturated or partially unsaturated heterocyclic ring having 1-4 heteroatoms independently selected from nitrogen, oxygen, and sulfur, and a 5-6 membered heteroaryl ring having 1-4 heteroatoms independently selected from nitrogen, oxygen, and sulfur.

2. The compound of claim 1, wherein A is —S—, —S(O)— or —S(O)$_2$—.

3. The compound of claim 1, wherein L$^1$ is an optionally substituted bivalent straight or branched C$_{2-3}$ hydrocarbon chain.

4. The compound of claim 1 of the formula Ia, Ib, Ic or Id:

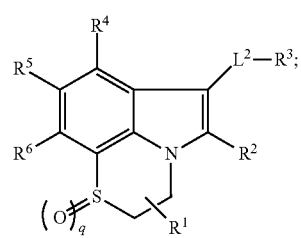

Ia

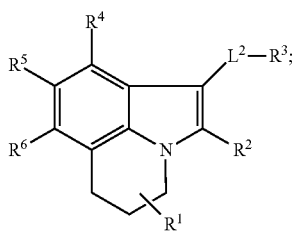

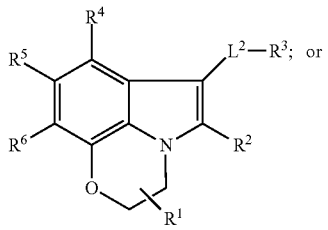

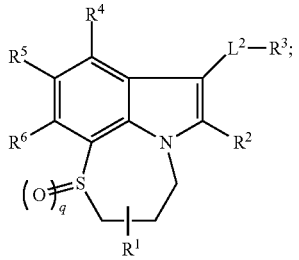

or a pharmaceutically acceptable salt thereof, wherein q is 0, 1 or 2.

5. The compound of claim 1, wherein $R^1$ is hydrogen.

6. The compound of claim 1, wherein $R^2$ is —$CO_2H$, —C(O)NHSO$_2$CH$_3$ or —C(O)NHSO$_2$C$_6$H$_5$.

7. The compound of claim 1, wherein $L^2$ is an optionally substituted bivalent straight or branched $C_{3-4}$ hydrocarbon chain wherein one methylene unit of $L^2$ is optionally replaced with —O-.

8. The compound of claim 7, wherein $L^2$ is —CH$_2$CH$_2$O— or —CH$_2$CH$_2$CH$_2$O—.

9. The compound of claim 1, wherein $R^3$ is optionally substituted phenyl or an optionally substituted 6-10 membered bicyclic saturated, partially unsaturated or aryl ring.

10. The compound of claim 9, wherein $R^3$ is

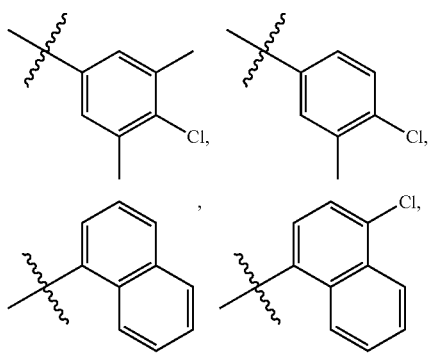

11. The compound of claim 1, wherein $R^4$ is hydrogen.
12. The compound of claim 1, wherein $R^5$ is hydrogen.
13. The compound of claim 1, wherein $R^6$ is hydrogen or halogen.
14. The compound of claim 13, wherein $R^6$ is hydrogen.
15. The compound of claim 13, wherein $R^6$ is —Cl.
16. The compound of claim 1, selected from the group consisting of:
6-(2-(naphthalen-1-yloxy)ethyl)-2,3-dihydro-[1,4]thiazino[2,3,4-hi]indole-5-carboxylic acid;
N-(methylsulfonyl)-6-(2-(naphthalen-1-yloxy)ethyl)-2,3-dihydro-[1,4]thiazino[2,3,4-hi]indole-5-carboxamide;
6-(2-(4-chloro-3,5-dimethylphenoxy)ethyl)-2,3-dihydro-[1,4]thiazino[2,3,4-hi]indole-5-carboxylic acid;
1-(2-(naphthalen-1-yloxy)ethyl)-5,6-dihydro-4H-pyrrolo[3,2,1-ij]quinoline-2-carboxylic acid;
6-(2-(naphthalen-1-yloxy)ethyl)-2,3-dihydro-[1,4]oxazino[2,3,4-hi]indole-5-carboxylic acid;
6-(2-(naphthalen-1-yloxy)ethyl)-N-(phenylsulfonyl)-2,3-dihydro-[1,4]oxazino[2,3,4-hi]indole-5-carboxamide;
6-(3-(naphthalen-1-yloxy)propyl)-2,3-dihydro-[1,4]thiazino[2,3,4-hi]indole-5-carboxylic acid;
N-(methylsulfonyl)-6-(3-(naphthalen-1-yloxy)propyl)-2,3-dihydro-[1,4]thiazino[2,3,4-hi]indole-5-carboxamide;
6-(3-((5,6,7,8-tetrahydronaphthalen-1-yl)oxy)propyl)-2,3-dihydro-[1,4]thiazino[2,3,4-hi]indole-5-carboxylic acid;
6-(3-((4-chloronaphthalen-1-yl)oxy)propyl)-2,3-dihydro-[1,4]thiazino[2,3,4-hi]indole-5-carboxylic acid;
6-(3-((5,6,7,8-tetrahydronaphthalen-2-yl)oxy)propyl)-2,3-dihydro-[1,4]thiazino[2,3,4-hi]indole-5-carboxylic acid;
6-(3-(4-chloro-3-methylphenoxy)propyl)-2,3-dihydro-[1,4]thiazino[2,3,4-hi]indole-5-carboxylic acid;
6-(3-(4-chloro-3,5-dimethylphenoxy)propyl)-2,3-dihydro-[1,4]thiazino[2,3,4-hi]indole-5-carboxylic acid;
1-(3-(naphthalen-1-yloxy)propyl)-5,6-dihydro-4H-pyrrolo[3,2,1-ij]quinoline-2-carboxylic acid;
N-(methylsulfonyl)-1-(3-(naphthalen-1-yloxy)propyl)-5,6-dihydro-4H-pyrrolo[3,2,1-ij]quinoline-2-carboxamide;
1-(3-(4-chloro-3,5-dimethylphenoxy)propyl)-5,6-dihydro-4H-pyrrolo[3,2,1-ij]quinoline-2-carboxylic acid;
1-(3-(4-chloro-3,5-dimethylphenoxy)propyl)-N-(phenylsulfonyl)-5,6-dihydro-4H-pyrrolo[3,2,1-]quinoline-2-carboxamide;
7-(3-(naphthalen-1-yloxy)propyl)-3,4-dihydro-2H-[1,4]thiazepino[2,3,4-hi]indole-6-carboxylic acid;
N-(methylsulfonyl)-7-(3-(naphthalen-1-yloxy)propyl)-3,4-dihydro-2H-[1,4]thiazepino[2,3,4-hi]indole-6-carboxamide;
7-(3-(naphthalen-1-yloxy)propyl)-3,4-dihydro-2H-[1,4]thiazepino[2,3,4-hi]indole-6-carboxylic acid 1-oxide;

7-(3-(naphthalen-1-yloxy)propyl)-3,4-dihydro-2H-[1,4] thiazepino[2,3,4-hi]indole-6-carboxylic acid 1,1-dioxide;

6-(3-(naphthalen-1-yloxy)propyl)-2,3-dihydro-[1,4]thiazino[2,3,4-hi]indole-5-carboxylic acid 1,1-dioxide;

7-(3-(4-chloro-3,5-dimethylphenoxy)propyl)-3,4-dihydro-2H-[1,4]thiazepino[2,3,4-hi]indole-6-carboxylic acid;

7-(3-(4-chloro-3,5-dimethylphenoxy)propyl)-N-(phenylsulfonyl)-3,4-dihydro-2H-[1,4]thiazepino[2,3,4-hi]indole-6-carboxamide;

6-(3-(naphthalen-1-yloxy)propyl)-2,3-dihydro-[1,4]oxazino[2,3,4-hi]indole-5-carboxylic acid;

6-(3-(4-chloro-3,5-dimethylphenoxy)propyl)-2,3-dihydro-[1,4]oxazino[2,3,4-hi]indole-5-carboxylic acid;

9-chloro-6-(3-(4-chloro-3,5-dimethylphenoxy)propyl)-2,3-dihydro-[1,4]oxazino[2,3,4-hi]indole-5-carboxylic acid; and 7-chloro-1-(3-(4-chloro-3,5-dimethylphenoxy)propyl)-5,6-dihydro-4H-pyrrolo[3,2,1-ij]quinoline-2-carboxylic acid;

or a pharmaceutically acceptable salt thereof.

17. The compound of claim 1, wherein the compound has a Ki value less than about 1 μM for inhibition of Mcl-1.

18. A pharmaceutical composition comprising a therapeutically effective amount of a compound of claim 1, and a pharmaceutically acceptable carrier.

19. The pharmaceutical composition of claim 18, further comprising one or more other therapeutically active agents selected from the group consisting of anti-cancer agents consisting of alkylating agents, angiogenesis inhibitors, antibodies, antimetabolites, antimitotics, antiproliferatives, aurora kinase inhibitors, Bcl-2 family protein inhibitors, Bcr-Abl kinase inhibitors, biologic response modifies, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, inhibitors of apoptosis protein (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids, deltoids, plant alkaloids, and topoisomerase inhibitors.

\* \* \* \* \*